(12) United States Patent
Foulon et al.

(10) Patent No.: US 6,673,790 B1
(45) Date of Patent: Jan. 6, 2004

(54) INDOLIN-2-ONE DERIVATIVES, PREPARATION AND THEIR USE AS OCYTOCIN RECEPTOR LIGANDS

(75) Inventors: Loïc Foulon, Portet sur Garonne (FR); Georges Garcia, Frontignan (FR); Claudine Serradeil-Le Gal, Escalquens (FR); Gérard Valette, Lacroix-Falgarde (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/240,483

(22) PCT Filed: Apr. 2, 2001

(86) PCT No.: PCT/FR01/00980

§ 371 (c)(1), (2), (4) Date: Oct. 2, 2002

(87) PCT Pub. No.: WO01/74775

PCT Pub. Date: Oct. 11, 2001

(51) Int. Cl.[7] .......................... A61P 5/10; C17D 209/34; A61K 31/404
(52) U.S. Cl. .................. 514/217.08; 544/144; 544/373; 514/339; 514/417; 514/414; 514/254.09; 514/323; 514/217.03; 514/235.2; 546/277.7; 546/201; 548/486; 548/467; 540/602
(58) Field of Search ................................. 514/339, 417, 514/414, 235.2, 254.09, 323, 217.13, 217.08; 546/277.7, 201; 548/486, 487, 467; 544/144, 373; 540/602

(56) References Cited

U.S. PATENT DOCUMENTS 5,594,023 A    1/1997  Wagnon et al.
5,726,322 A    3/1998  DiMalta et al.

FOREIGN PATENT DOCUMENTS

EP    0636608        2/1995
WO    WO 95/18105    7/1995

Primary Examiner—Joseph K. McKane
Assistant Examiner—Andrea D. Small
(74) Attorney, Agent, or Firm—Michael D. Alexander; Paul E. Dupont

(57) ABSTRACT

The present invention relates to novel indolin-2-one derivatives of formula:

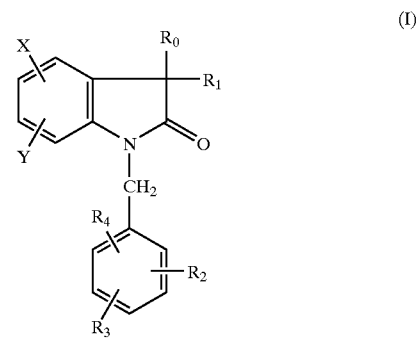

(I)

to the preparation and to the pharmaceutical compositions comprising them.

These compounds have an affinity for oxytocin receptors.

29 Claims, No Drawings

INDOLIN-2-ONE DERIVATIVES, PREPARATION AND THEIR USE AS OCYTOCIN RECEPTOR LIGANDS

This application is a 371 of PCT/FR01/00980 Apr. 2, 2001.

A subject-matter of the present invention is novel indolin-2-one derivatives, a process for their preparation and the pharmaceutical compositions comprising them. These novel derivatives are powerful and selective ligands of the oxytocin receptors and can thus be used as an active principle in pharmaceutical compositions, in particular in the obstetric or gynaecological field. Oxytocin (OT) is a hormone excreted by the neurohypophysis with a cyclic nonapeptide structure similar to that of arginine vasopressin (AVP). The oxytocin receptors are essentially found on the smooth muscle of the uterus and on the myoedithelial cells of the mammary glands. Thus, oxytocin plays an important role in parturition since it is involved in the contraction of the uterine muscle and in lactation. Furthermore, oxytocin receptors are also located in other peripheral tissues and in the central nervous system; oxytocin can thus have effects in the cardiovascular, renal, endocrinal or behavioural fields.

Indolin-2-one derivatives have been disclosed in some patent applications as ligands of the vasopressin receptors and possibly of the oxytocin receptors; mention may be made of Patent Applications WO 93/15051, EP 636 608, EP 636 609, WO 95/18105, WO 97/15556 and WO 98/25901. To date, no indolin-2-one derivative has been disclosed as a powerful and selective ligand of oxytocin receptors.

It has now been found that certain indolin-2-one derivatives are powerful and selective ligands of oxytocin receptors.

Thus, according to one of its aspects, the present invention relates to novel indolin-2-one derivatives in the form of a pure enantiomer or a mixture of enantiomers of formula:

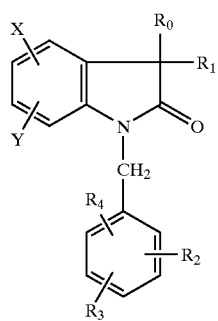

(I)

in which:

$R_0$ represents a group chosen from:

(i):

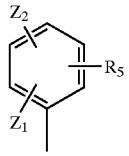

in which:

$Z_1$ represents a chlorine, bromine, iodine or fluorine atom or a $(C_1-C_4)$alkyl, $(C_1-C_4)$alkoxy or trifluoromethyl group;

$Z_2$ represents a hydrogen, chlorine, bromine, iodine or fluorine atom or a $(C_1-C_4)$alkyl, $(C_3-C_5)$cycloalkyl, $(C_1-C_4)$alkoxy, $(C_3-C_5)$ cycloalkoxy or $(C_1-C_4)$ polyfluoroalkyl group;

$R_5$ represents $T_1W$ in which $T_1$ represents $—(CH_2)_m$, it being possible for m to be equal to 0 or 1, and W represents a hydrogen atom or a hydroxycarbonyl (or carboxyl), $(C_1-C_4)$alkoxycarbonyl, 1,3-dioxolan-2-yl or 1,3-dioxan-2-yl group, or else W represents an $—NR_6R_7$ group in which $R_6$ and $R_7$ represent, independently of one another, a hydrogen atom, a $(C_1-C_4)$alkyl group, a $(C_1-C_4)$alkylsulphonyl group or a phenylsulphonyl group in which the phenyl group can be mono-, di- or trisubstituted by $Z_5$; or else $R_6$ and $R_7$ form, with the nitrogen atom to which they are bonded, a morpholinyl group optionally substituted by a $(C_1-C_4)$alkyl group or an oxo; or else $R_6$ and $R_7$ form, with the nitrogen atom to which they are bonded, a piperazinyl group optionally substituted in the 4-position by a $Z_3$ substituent; or else $R_6$ and $R_7$ form, with the nitrogen atom to which they are bonded, a pyrrolidinyl or piperidyl group, the said pyrrolidinyl and piperidyl groups optionally being substituted by $Z_4$;

or else W represents an $—NR_8COR_9$ group in which $R_8$ represents a hydrogen atom or a $(C_1-C_4)$alkyl group and $R_9$ represents a hydrogen atom or a $(C_1-C_4)$alkyl, benzyl, pyridyl or phenyl group, it being possible for the said phenyl group to be mono-, di- or trisubstituted by $Z_5$; or else $R_9$ represents an $—NR_{10}R_{11}$ group in which $R_{10}$ and $R_{11}$ represent, independently of one another, a hydrogen atom or a $(C_1-C_4)$alkyl [lacuna] or else $R_{10}$ and $R_{11}$ form, with the nitrogen atom to which they are bonded, a pyrrolidinyl, piperidyl or morpholinyl group optionally substituted by a $(C_1-C_4)$ alkyl group; or else $R_9$ represents a pyrrolidin-2-yl or -3-yl or piperid-2-yl, -3,-yl or -4-yl group, the said pyrrolidinyl and piperidyl groups optionally being substituted by $Z_7$; or else $R_9$ represents a $—T_2—R_{12}$ or $—T_2—COR_{12}$ group in which $T_2$ represents $—(CH_2)_n—$, it being possible for n to be equal to 1, 2, 3 and 4, and $R_{12}$ represents a $(C_1-C_4)$alkoxy or $—NR_{10}R_{11}$ group, $R_{10}$ and $R_{11}$ being as defined above;

or else W represents a $—CONR_{13}R_{14}$ group in which $R_{13}$ represents a hydrogen atom or a $(C_1-C_4)$ alkyl, $(C_3-C_7)$ cycloalkyl, monofluoro$(C_1-C_4)$ alkyl or polyfluoro$(C_1-C_4)$alkyl group and $R_{14}$ represents a hydrogen atom, a $(C_1-C_4)$alkyl group, a phenyl group optionally substituted by $Z_5$, a $—T_4—R_{15}$ group in which $T_4$ represents $—(CH_2)_q$, with q equal to 1, 2, 3 or 4, and $R_{15}$ represents a hydroxyl group, a $(C_1-C_4)$alkoxy group, a $(C_1-C_4)$alkoxycarbonyl group, a $(C_1-C_4)$ alkoxycarbonylamino group, a phenyl group optionally mono- or disubstituted by $Z_5$, a pyrid-2-yl, -3-yl or -4-yl, or an $—NR_{16}R_{17}$ group in which $R_{16}$ and $R_{17}$ represent, independently of one another, a hydrogen atom or a $(C_1-C_4)$alkyl [lacuna] or else $R_{16}$ and $R_{17}$ form, with the nitrogen atom to which they are bonded, a morpholinyl group optionally mono- or disubstituted by a ($C_1$–$C_4$)alkyl group or else $R_{16}$ and $R_{17}$ form, with the nitrogen atom to which they are bonded, a piperazinyl group optionally substituted in the 4-position by a $Z_3$ substituent or else $R_{16}$ and $R_{17}$ form, with the nitrogen atom to which they are bonded, a pyrrolidinyl or piperidyl group, the said pyrrolidinyl and piperidyl groups optionally being substituted by $Z_5$, it being understood that, when q=1, $R_{15}$ is other than hydroxyl, ($C_1$–$C_4$)alkoxy, ($C_1$–$C_4$)alkoxycarbonylamino or —$NR_{16}R_{17}$; or else $R_{13}$ and $R_{14}$ form, with the nitrogen atom to which they are bonded, a morpholinyl group optionally mono- or disubstituted by a ($C_1$–$C_4$) alkyl group or a piperazinyl group optionally substituted in the 4-position by a $Z_3$ substituent; or else $R_{13}$ and $R_{14}$ form, with the nitrogen atom to which they are bonded, an azetidinyl, pyrrolidinyl, piperidyl or hexahydroazepinyl group, the said pyrrolidinyl, piperidyl and hexahydroazepinyl groups optionally being mono- or disubstituted by $Z_8$;

or else W represents an $OR_{18}$ group in which $R_{18}$ represents a hydrogen atom or a ($C_1$–$C_4$)alkyl, ($C_1$–$C_4$)alkoxy($C_1$–$C_4$)alkyl or —$T_3$—$R_{19}$ group in which $T_3$ represents —$(CH_2)_p$—, it being possible for p to be equal to 2 or 3, and $R_{19}$ is chosen from the hydroxyl, triphenylmethoxy or —$NR_{20}R_{21}$ groups in which $R_{20}$ represents a hydrogen atom or a ($C_1$–$C_4$)alkyl group and $R_{21}$ represents a hydrogen atom or a ($C_1$–$C_4$)alkyl, tetrahydrofuranylmethyl or tetrahydropyranylmethyl group, or else $R_{20}$ and $R_{21}$ form,,with the nitrogen atom to which they are bonded, a morpholinyl group optionally mono- or disubstituted by a ($C_1$–$C_4$)alkyl group or a piperazinyl group optionally substituted in the 4-position by a $Z_3$ substituent, or else $R_{20}$ and $R_{21}$ form, with the nitrogen atom to which they are bonded, a pyrrolidinyl or piperidyl group, the said pyrrolidinyl and piperidyl groups optionally being substituted by $Z_5$;

$Z_3$ represents a ($C_1$–$C_4$)alkyl, pyridyl, phenyl, ($C_1$–$C_4$) alkylcarbonyl or ($C_1$–$C_4$)alkoxycarbonyl group;

$Z_4$ represents an oxo, a fluorine atom, a hydroxyl, a ($C_1$–$C_4$)alkyl, a benzyl, an amino, a ($C_1$–$C_4$) alkylamino, a di($C_1$–$C_4$)alkylamino, a ($C_1$–$C_4$) alkoxy, a ($C_1$–$C_4$)alkoxycarbonyl or a ($C_1$–$C_4$) alkoxycarbonylamino;

$Z_5$ represents a chlorine, bromine, iodine or fluorine atom, a hydroxyl group, a ($C_1$–$C_4$)alkyl group or a ($C_1$–$C_4$)alkoxy group;

Z7 represents a fluorine atom, a hydroxyl group, a hydroxy($C_1$–$C_4$)alkyl group, a ($C_1$–$C_4$)alkyl [lacuna], a ($C_1$–$C_4$)alkoxy [lacuna] or a ($C_1$–$C_4$) alkylcarbonyl [lacuna];

$Z_8$ represents a fluorine atom or a hydroxyl, ($C_1$–$C_4$) alkyl, ($C_3$–$C_6$)cycloalkyl, benzyl, amino, ($C_1$–$C_4$) alkylamino, di($C_1$–$C_4$)alkylamino, ($C_1$–$C_4$) alkoxycarbonyl, ($C_1$–$C_4$)alkoxycarbonylamino, ($C_3$–$C_6$)cycloalkoxy, hydroxycarbonyl, hydroxy ($C_1$–$C_4$)alkyl, ($C_1$–$C_4$)alkoxy($C_1$–$C_4$)alkyl, ($C_1$–$C_4$) alkoxy or —$CONR_{23}R_{24}$ group in which $R_{23}$ and $R_{24}$ represent, independently of one another, a hydrogen atom, a ($C_1$–$C_4$)alkyl, a monofluoro ($C_1$–$C_4$)alkyl or a polyfluoro($C_1$–$C_4$)alkyl, or else $R_{23}$ and $R_{24}$ form, with the nitrogen atom to which they are bonded, a pyrrolidinyl or piperidyl group, the said pyrrolidinyl or piperidyl groups optionally being substituted by $Z_3$ or a difluoromethylidene;

(ii):

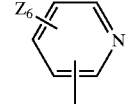

$Z_6$ represents a chlorine atom or a ($C_1$–$C_4$)alkyl or ($C_1$–$C_4$) alkoxy group;

$R_1$ represents a ($C_1$–$C_4$)alkyl group optionally comprising a double or a triple bond, a ($C_1$–$C_4$)alkoxycarbonyl group, a phenyloxycarbonyl group or a $T_1$—$R_{22}$ group in which $T_1$ is as defined above and $R_{22}$ represents a hydroxyl or ($C_1$–$C_4$)alkoxy group;

$R_2$ and $R_4$ represent, independently of one another, a hydrogen, chlorine or fluorine atom or a ($C_1$–$C_4$)alkyl or ($C_1$–$C_4$)alkoxy group;

$R_3$ represents a chlorine or fluorine atom or a ($C_1$–$C_4$) alkyl, ($C_1$–$C_4$)alkoxy, hydroxyl, ($C_1$–$C_4$)carbamoyl, ($C_1$–$C_4$)alkylcarbonylamino, nitro, cyano, trifluoromethyl, amino, ($C_3$–$C_6$)cycloalkylamino, ($C_1$–$C_4$)alkylamino, di($C_1$–$C_4$) alkylamino, tri($C_1$–$C_4$) alkylammonium $A^-$, $A^-$ being an anion, pyrrolidin-1-yl, piperid-1-yl, piperazin-1-yl, morpholin-4-yl or hexahydroazepin-1-yl group;

X and Y represent, independently of one another, a hydrogen, chlorine, bromine, iodine or fluorine atom or a ($C_1$–$C_4$)alkoxy or trifluoromethoxy group; and to their pharmaceutically acceptable salts, their solvates and their hydrates.

The term "alkyl" is understood to mean a saturated, linear or branched, monovalent hydrocarbonaceous radical.

The term "($C_1$–$C_4$)alkyl" is understood to mean an alkyl radical comprising from 1 to 4 carbon atoms, such as methyl, ethyl, n-propyl, isopropyl, n-butyl, isobutyl, sec-butyl and tert-butyl.

The term "alkylene" is understood to mean a saturated, linear or branched, bivalent hydrocarbonaceous radical.

The term "alkoxy" is understood to mean an O-alkyl radical.

The term "anion $A^-$" is understood to mean, for example, a $Cl^-$, $Br^-$, $I^-$ or $CH_3SO_4^-$.

The term "di($C_1$–$C_4$)alkylamino" is understood to mean an amino radical substituted by two alkyl radicals which can be identical or different. In the same way, for tri($C_1$–$C_4$) ammoniums, the alkyl radicals can be identical or different.

The salts of the compounds according to the invention are prepared according to techniques which are well known to a person skilled in the art. The salts of the compounds of formula (I) according to the present invention comprise those with inorganic or organic acids, which make possible suitable separation or crystallization of the compounds of formula (I), and pharmaceutically acceptable salts. Mention may be made, as appropriate acid, of: picric acid, oxalic acid or an optically active acid, for example a tartaric acid, a dibenzoyltartaric acid, a mandelic acid or a camphorsulphonic acid, and those which form physiologically acceptable salts, such as the hydrochloride, the hydrobromide, the sulphate, the hydrogensulphate, the dihydrogenphosphate, the maleate, the fumarate, the 2-naphthalenesulphonate or the para-toluenesulphonate, the hydrochloride being preferred.

When a compound according to the invention exhibits one or more asymmetric carbons, the optical isomers of this compound form an Integral part of the invention. When a compound according to the invention exhibits stereoisomerism, for example of axial-equatorial or Z-E type, the invention comprises all the stereoisomers of this compound.

The present invention comprises the compounds of formula (I) in the form of pure isomers but also in the form of a mixture of isomers in any proportion.

The compounds (I) are isolated in the form of pure isomers by conventional separating techniques: use may be made, for example, of fractional recrystallizations of a salt of the racemate with an optionally active acid or base, the principle of which is well known, or conventional chromatography techniques on a chiral or nonchiral phase.

The compounds of formula (I) above also comprise those in which one or more hydrogen, carbon or halogen, in particular iodine, chlorine or fluorine, atoms have been replaced by their radioactive isotope, for example tritium or carbon-14. Such labelled compounds are of use in research, metabolic or pharmacokinetic studies or in biochemical assays as receptor ligand.

The functional groups possibly present in the molecule of the compounds of formula (I) and in the reaction intermediates can be protected, either in permanent form or in temporary form, by protective groups which ensure unequivocal synthesis of the expected compounds. The protection and deprotection reactions are carried out according to techniques well known to persons skilled in the art. The term "temporary protective group for amines or alcohols" is understood to mean protective groups such as those described in Protective Groups in organic Synthesis, Greene T. W. and Wuts P. G. M., published by Wiley Intersciences, 1999, and in Protecting Groups, Kocienski P. J., 1994, Georg Thieme Verlag.

Mention may be made, for example, of temporary protective groups for amines: benzyls, carbamates (such as tert-butyloxycarbonyl, which can be cleaved in acidic medium, or benzyloxycarbonyl, which can be cleaved by hydrogenolysis); for carboxylic acids: alkyl esters (such as methyl, ethyl or tert-butyl esters, which can hydrolyse in basic or acidic medium) and benzyl esters, which can be hydrogenolysed; for alcohols or for phenols, such as tetrahydropyranyl, methyloxymethyl, methylethoxymethyl, tert-butyl and benzyl ethers; or for carbonyl derivatives, such as linear or cyclic acetals, like, for example, 1,3-dioxane-2-yl or 1,3-dioxolan-2-yl; and reference may be made to the well known general methods described in the abovementioned Protective Groups.

A person skilled in the art will be in a position to choose the appropriate protective groups. The compounds of formula (I) can comprise precursor groups of other functional groups which are subsequently generated in one or more other stages.

One family of compounds according to the invention is composed of indolin-2-one derivatives in the form of a pure enantiomer or of a mixture of enantiomers of formula:

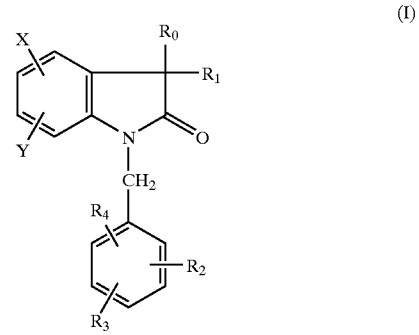

(I)

in which:

$R_0$ represents (i):

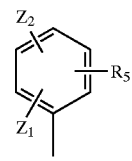

$Z_1$, $Z_2$, $R_1$, $R_2$, $R_3$, $R_4$, $R_5$, Y and X are as defined for (I), and their pharmaceutically acceptable salts, their solvates and their hydrates.

According to another of its aspects, the invention relates to the compounds of formula:

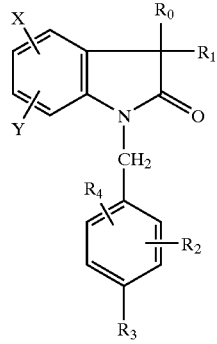

(Ia)

in which $R_1$ represents a methyl or hydroxyl group and $R_0$, $R_2$, $R_3$, $R_4$, X and Y are as defined for (I); in the form of a pure enantiomer or of a mixture of enantiomers, and their pharmaceutically acceptable salts, their solvates and their hydrates.

A subfamily of the compounds according to the invention is composed of the compounds of formula:

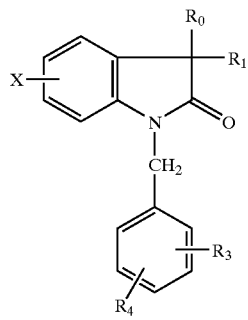

(Ib)

in which $R_1$ represents a methyl or hydroxyl group and $R_0$, $R_3$, $R_4$ and X are as defined for (I); in the form of a pure enantiomer or of a mixture of enantiomers, and their pharmaceutically acceptable salts, their solvates and their hydrates.

Another subfamily of the compounds according to the invention is composed of the compounds of formula:

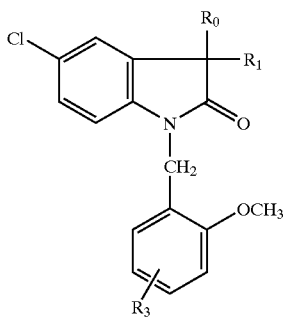

(Ic)

in which $R_1$ represents a methyl or hydroxyl group and $R_0$ and $R_3$ are as defined for (I); in the form of a pure enantiomer or of a mixture of enantiomers, and their pharmaceutically acceptable salts, their solvates and their hydrates.

Another subfamily of the compounds according to the invention is composed of the compounds of formula:

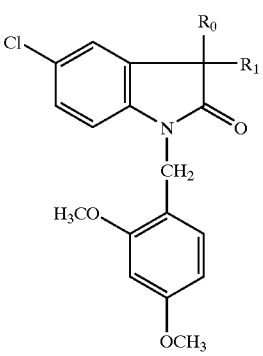

(Id)

in which $R_1$ represents a methyl or hydroxyl group and $R_0$ is as defined for (I); in the form of a pure enantiomer or of a mixture of enantiomers, and their pharmaceutically acceptable salts, their solvates and their hydrates.

Among these compounds of formula (I), (Ia), (Ib), (Ic) and (Id), those in which $R_0$ represents the group:

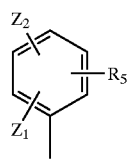

in particular the group:

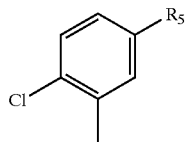

in which $R_5$ is as defined for (I), constitute another aspect of the invention.

Among the latter compounds, those in which $R_1$ represents a methyl group constitute another aspect of the invention.

According to another of its aspects, the invention relates to the compounds chosen from: 5-Chloro-3-(2-chlorophenyl)-1-(2,4-dimethoxybenzyl)-3-methylindolin-2-one (Example 1);

5-Chloro-3-(2-chlorophenyl)-1-[4-(isopropylamino)-2-methoxybenzyl]-3-methylindolin-2-one (Example 56);

N-{4-Chloro-3-[5-chloro-1-(2,4-dimethoxybenzyl)-3-methyl-2-oxoindolin-3-yl]phenyl}acetamide (Example 70);

N-{4-Chloro-3-[5-chloro-1-(2,4-dimethoxybenzyl)-3-methyl-2-oxoindolin-3-yl]phenyl}-3-methylbutanamide (Example 73);

N-{4-Chloro-3-[5-chloro-1-(2,4-dimethoxybenzyl)-3-methyl-2-oxoindolin-3-yl]phenyl}benzamide (Example 74);

N-{4-Chloro-3-[5-chloro-1-(2,4-dimethoxybenzyl)-3-methyl-2-oxoindolin-3-yl]phenyl}nicotinamide (Example 76);

N-{4-Chloro-3-[5-chloro-1-(2,4-dimethoxybenzyl)-3-methyl-2-oxoindolin-3-yl]phenyl}-2-methoxyacetamide (Example 77);

Methyl 3-{4-chloro-3-[5-chloro-1-(2,4-dimethoxybenzyl)-3-methyl-2-oxoindolin-3-yl]anilino}-3-oxopropanoate (Example 78);

N-{4-Chloro-3-[5-chloro-1-(2,4-dimethoxybenzyl)-3-methyl-2-oxoindolin-3-yl]phenyl}-3-methoxypropanamide (Example 81);

N-{4-Chloro-3-[5-chloro-1-(2,4-dimethoxybenzyl)-3-methyl-2-oxoindolin-3-yl]phenyl}-N-methylacetamide (Example 87);

N-{4-Chloro-3-[5-chloro-1-(2,4-dimethoxybenzyl)-3-methyl-2-oxoindolin-3-yl]phenyl}-N-methylmethanesulphonamide (Example 97);

4-Chloro-3-[5-chloro-1-(2,4-dimethoxybenzyl)-3-methyl-2-oxoindolin-3-yl]-N,N-diethylbenzamide (Example 102);

4-Chloro-3-[5-chloro-1-(2,4-dimethoxybenzyl)-3-methyl-2-oxoindolin-3-yl]-N,N-dimethylbenzamide (Example 109);

5-Chloro-3-[2-chloro-5-(1-piperidylcarbonyl)phenyl]-1-(2,4-dimethoxybenzyl)-3-methylindolin-2-one (Example 112);

4-Chloro-3-[5-chloro-1-(2,4-dimethoxybenzyl)-3-methyl-2-oxoindolin-3-yl]-N-ethylbenzamide (Example 114);

5-Chloro-3-(2-chloro-5-{[2-(methoxymethyl)-1-pyrrolidinyl]carbonyl}phenyl)-1-(2,4-dimethoxybenzyl)-3-methylindolin-2-one (Example 119);

5-Chloro-3-{2-chloro-5-[(2-methyl-1-piperidyl)-carbonyl]phenyl}-1-(2,4-dimethoxybenzyl)-3-methylindolin-2-one (Example 122);

4-Chloro-3-[5-chloro-1-(2,4-dimethoxybenzyl)-3-methyl-2-oxoindolin-3-yl]-N-ethyl-N-methylbenzamide (Example 124);

Methyl 1-{4-chloro-3-[5-chloro-1-(2,4-dimethoxybenzyl)-3-methyl-2-oxoindolin-3-yl]benzoyl}-2-piperidine-carboxylate (Example 131);

5-Chloro-3-{2-chloro-5-[(4-hydroxy-1-piperidyl)-carbonyl]phenyl}-1-(2,4-dimethoxybenzyl)-3-methyl-indolin-2-one (Example 134);

5-Chloro-3-{2-chloro-5-[(2-methoxyethoxy)methyl]-phenyl}-1-(2,4-dimethoxybenzyl)-3-methylindolin-2-one (Example 142);

5-Chloro-3-[2-chloro-5-(4-morpholinylmethyl)phenyl]-1-(2,4-dimethoxybenzyl)-3-methylindolin-2-one (Example 148);

5-Chloro-3-(2-chloro-5-{[2-(4-morpholinyl)ethoxy]-ethyl}phenyl)-1-(2,4-dimethoxybenzyl)-3-methylindolin-2-one (Example 152);

1-[4-Chloro-3-[5-chloro-1-(2,4-dimethoxybenzyl)-3-methyl-2-oxoindolin-3-yl]benzoyl]-3-hydroxypiperidine (Example 194);

1-[4-Chloro-3-[5-chloro-1-(2,4-dimethoxybenzyl)-3-methyl-2-oxoindolin-3-yl]benzoyl]-(R)-3-hydroxypiperidine (Example 195);

1-[4-Chloro-3-[5-chloro-1-(2,4-dimethoxybenzyl)-3-methyl-2-oxoindolin-3-yl]benzoyl]-4-methoxypiperidine (Example 166);

1-[4-Chloro-3-[5-chloro-1-(2,4-dimethoxybenzyl)-3-methyl-2-oxoindolin-3-yl]benzoyl]-4-ethoxypiperidine (Example 167);

1-[4-Chloro-3-[5-chloro-1-(2,4-dimethoxybenzyl)-3-methyl-2-oxoindolin-3-yl]benzoyl]-(R,S)-2,6-dimethylpiperidine (Example 189);

1-[4-Chloro-3-[5-chloro-1-(2,4-dimethoxybenzyl)-3-methyl-2-oxoindolin-3-yl]benzoyl]-(R)-2-ethoxycarbonylpiperidine (Example 175);

1-[4-Chloro-3-[5-chloro-1-(2,4-dimethoxybenzyl)-3-methyl-2-oxoindolin-3-yl]benzoyl]-(R)-2-N,N-dimethyl-aminocarbonylpiperidine (Example 169);

1-[4-Chloro-3-[5-chloro-1-(2,4-dimethoxybenzyl)-3-methyl-2-oxoindolin-3-yl]benzoyl]-(R)-2-(N-methyl-N-2,2,2-trifluoroethylaminocarbonyl)piperidine (Example 170);

1-[4-Chloro-3-[5-chloro-1-(2,4-dimethoxybenzyl)-3-methyl-2-oxoindolin-3-yl]benzoyl]-(R)-2-pyrrolidinocarbonylpiperidine (Example 168);

1-[4-Chloro-3-[5-chloro-1-(2,4-dimethoxybenzyl)-3-methyl-2-oxoindolin-3-yl]benzoyl]-(S)-2-methylpiperidine (Example 174);

4-Chloro-3-[5-chloro-1-(2,4-dimethoxybenzyl)-3-methyl-2-oxoindolin-3-yl]-N-ethyl-N-(2-phenylethyl)benzamide (Example 185);

4-Chloro-3-[5-chloro-1-(2,4-dimethoxybenzyl)-3-methyl-2-oxoindolin-3-yl]-N-ethyl-N-(4-pyridylmethyl)benzamide hydrochloride (Example 188);

4-Chloro-3-[5-chloro-1-(2,4-dimethoxybenzyl)-3-methyl-2-oxoindolin-3-yl]-N-ethyl-N-(3-pyridylmethyl)benzamide (Example 201);

4-Chloro-3-[5-chloro-1-(2,4-dimethoxybenzyl)-3-methyl-2-oxoindolin-3-yl]-N-ethyl-N-(2-pyridylmethyl)benzamide (Example 200);

4-Chloro-3-[5-chloro-1-(2,4-dimethoxybenzyl)-3-methyl-2-oxoindolin-3-yl]-N-ethyl-N-(2-methoxyethyl)benzamide (Example 184);

4-Chloro-3-[5-chloro-1-(2,4-dimethoxybenzyl)-3-methyl-2-oxoindolin-3-yl]-N-ethyl-N-(2-dimethylaminoethyl)-benzamide hydrochloride (Example 177);

4-Chloro-3-[5-chloro-1-(2,4-dimethoxybenzyl)-3-methyl-2-oxoindolin-3-yl]-N-ethyl-N-(2-morpholinoethyl)-benzamide (Example 178);

4-Chloro-3-[5-chloro-1-(2,4-dimethoxybenzyl)-3-methyl-2-oxoindolin-3-yl]-N-ethyl-N-(2-pyrrolidinoethyl)-benzamide hydrochloride (Example 182);

4-Chloro-3-[5-chloro-1-(2,4-dimethoxybenzyl)-3-methyl-2-oxoindolin-3-yl]-N-ethyl-N-(2-piperidinoethyl)-benzamide hydrochloride (Example 183);

4-Chloro-3-[5-chloro-1-(2,4-dimethoxybenzyl)-3-methyl-2-oxoindolin-3-yl]-N-ethyl-N-(2-hydroxyethyl)benzamide (Example 198);

4-Chloro-3-[5-chloro-1-(2,4-dimethoxybenzyl)-3-methyl-2-oxoindolin-3-yl]-N-ethyl-N-[2-(pyrid-4-yl)ethyl]-benzamide hydrochloride (Example 179);

4-Chloro-3-[5-chloro-1-(2,4-dimethoxybenzyl)-3-methyl-2-oxoindolin-3-yl]-N-ethyl-N-(2,2,2-trifluoroethyl)-benzamide (Example 180);

4-Chloro-3-[5-chloro-1-(2,4-dimethoxybenzyl)-3-methyl-2-oxoindolin-3-yl]-N-methyl-N-(2,2,2-trifluoroethyl)-benzamide (Example 171);

4-Chloro-3-[5-chloro-1-(2,4-dimethoxybenzyl)-3-methyl-2-oxoindolin-3-yl]-N-ethyl-N-isopropylbenzamide (Example 187);

4-Chloro-3-[5-chloro-1-(2,4-dimethoxybenzyl)-3-methyl-2-oxoindolin-3-yl]-N-(2-dimethylaminoethyl)-N-(2,2,2-trifluoroethyl)benzamide hydrochloride (Example 202);

4-Chloro-3-[5-chloro-1-(2,4-dimethoxybenzyl)-3-methyl-2-oxoindolin-3-yl]-N-cyclohexylbenzamide (Example 192);

4-Chloro-3-[5-chloro-1-(2,4-dimethoxybenzyl)-3-methyl-2-oxoindolin-3-yl]-N-ethyl-N-[3-(pyrid-4-yl)propyl]-benzamide (Example 204);

in the form of a pure enantiomer or of a mixture of enantiomers, and to their pharmaceutically acceptable salts, their solvates and their hydrates.

The compound of formula (I) can be prepared according to the following Scheme 1:

SCHEME 1

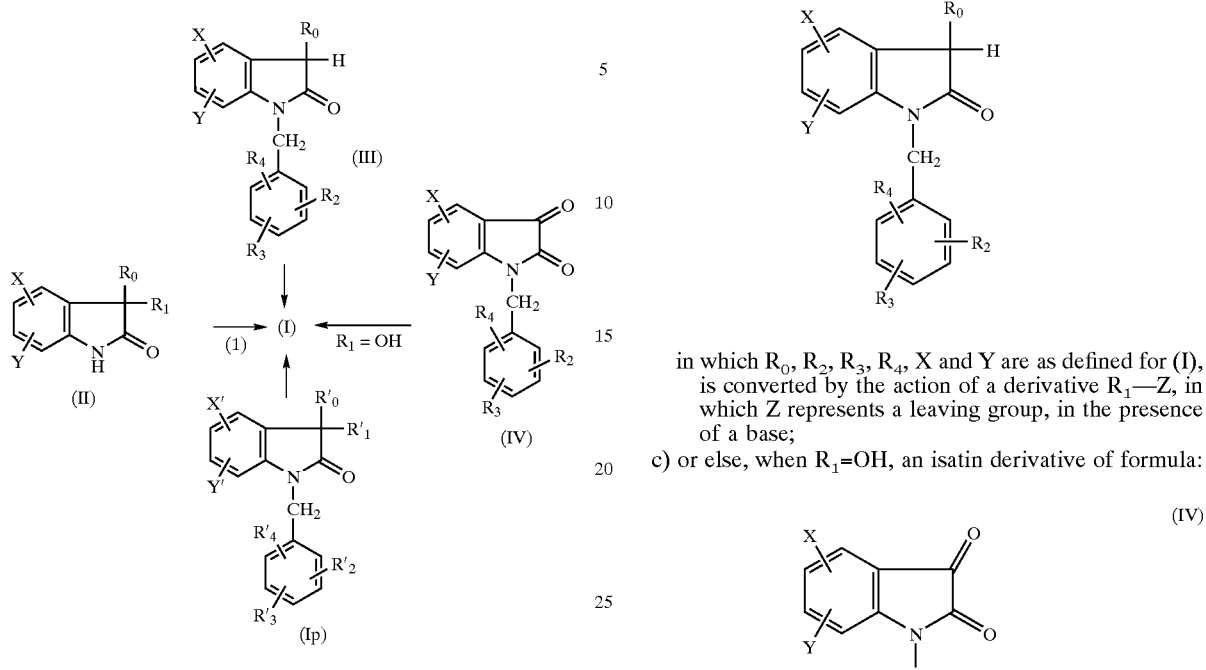

In this scheme, $R_0$, $R_1$, $R_2$, $R_3$, $R_4$, X and Y are as defined for (I) and, for (Ip), $R'_0$, $R'_1$, $R'_2$, $R'_3$, $R'_4$, X' and Y' respectively represent either $R_0$, $R_1$, $R_2$, $R_3$, $R_4$, X and Y as defined for (I) or a precursor group for $R_0$, $R_1$, $R_2$, $R_3$, $R_4$, X and Y, it being understood that $R'_1$ is other than hydrogen.

Another subject-matter of the present invention is a preparation process for the compounds of formula (I), characterized in that:

a) a compound of formula:

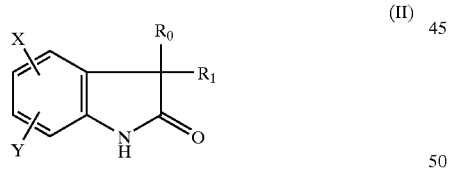

in which X, Y, $R_0$ and $R_1$ are as defined for (I), is reacted in the presence of a base with a halide of formula:

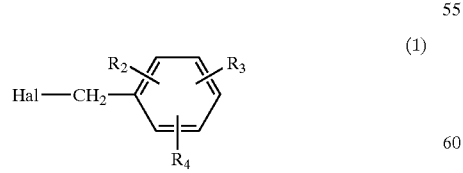

in which Hal represents a halogen atom and $R_2$, $R_3$ and $R_4$ are as defined for (I);

b) or else, when $R_1$ represents an electrophilic group, the compound of formula:

(III)

in which $R_0$, $R_2$, $R_3$, $R_4$, X and Y are as defined for (I), is converted by the action of a derivative $R_1$—Z, in which Z represents a leaving group, in the presence of a base;

c) or else, when $R_1$=OH, an isatin derivative of formula:

(IV)

in which $R_2$, $R_3$, $R_4$, X and Y are as defined for (I), is reacted with an organometallic derivative $R_0$—M or $R_0$MgHal, $R_0$ being as defined for (I), M being a metal atom and Hal being a bromine or iodine atom;

d) or else the compound of formula:

(Ip)

in which $R'_0$, $R'_1$, $R'_2$, $R'_3$, $R'_4$, X' and Y' respectively represent either $R_0$, $R_1$, $R_2$, $R_3$, $R_4$, X and Y as defined for (I) or a precursor group for $R_0$, $R_1$, $R_2$, $R_3$, $R_4$, X and Y, is subjected to a subsequent treatment to convert any one of the $R'_0$, $R'_1$, $R'_2$, $R'_3$, $R'_4$, X' and Y' groups to respectively $R_0$, $R_1$, $R_2$, $R_3$, $R_4$, X or Y as defined for (I), according to reactions well known to a person skilled in the art.

The reaction described in a) is preferably carried out with a compound (1) in which Hal=Cl or Br using, as base, a metal hydride, such as sodium hydride, or an alkali metal alkoxide, such as potassium tert-butoxide, in an anhydrous solvent, such as dimethylformamide or tetrahydrofuran.

In the reaction described in b), the term "leaving group" is understood to mean, for example, a halogen atom, such as chlorine, bromine or iodine, or alternatively a sulphonic ester group, such as para-toluenesulphonate. The compound (III) is preferably reacted with a halide $R_1$-Hal, $R_1$ being as defined for (I) and Hal being a halogen atom, preferably an iodine atom, in the presence of a base; the reaction will be carried out, for example, in the presence of a base, such as an alkali metal alkoxide, for instance potassium tert-butoxide, in an ethereal solvent, such as tetrahydrofuran, or alternatively in the presence of a carbonate, such as sodium, potassium or caesium carbonate, in a solvent such as dimethylformamide or acetonitrile.

Advantageously, in the reaction described in c), the compound of formula (IV) is reacted with a magnesium derivative $R_0$Mg-Hal, $R_0$ being as defined for (I) or (Ip) and Hal being a bromine or preferably iodine atom, or alternatively the compound (IV) is reacted with a derivative $R_0$M in which M is preferably a lithium atom. This derivative $R_0$Li is obtained either by direct lithiation, for example by the action of butyllithium or lithium diisopropylamide according to Heterocycles, 1993, 35(1), 151–169, or by a halogen-lithium exchange reaction according to Organolithium Methods, Pergamon Press, New York, 1988 or J. Am. Chem. Soc., 1956, 2217. These reactions are preferably carried out in an anhydrous solvent, such as diethyl ether or tetrahydrofuran.

The conversion of the compound (Ip), the precursor of the compound (I), described in d) is carried out according to conventional techniques.

Furthermore, the compounds (I) can be obtained from another compound,(I) by conversion of one of the $R_0$, $R_1$, $R_2$, $R_3$, $R_4$, X or Y substituents, in particular $R_0$, $R_1$ or $R_3$ substituents. For example:

the compounds (I) in which $R_3$=—$NH_2$ can be obtained by reduction of the corresponding compounds (I) in which $R_3$=—$NO_2$, for example by the action of hydrochloric acid in the presence of tin in an alcohol, such as ethanol;

the compounds (I) in which $R_3$ represents a ($C_1$–$C_4$) alkylamino or di($C_1$–$C_4$)alkylamino group can be obtained from the corresponding compounds (I) in which $R_3$=—$NH_2$ by a reductive amination reaction. Reference may be made to J. Org. Chem., 1996, 61, 3849–3862 and the reaction can be carried out by the action of a ($C_1$–$C_4$)alkyl aldehyde in the presence of sodium triacetoxyborohydride or alternatively reference may be made to J. Am. Chem. Soc., 1974, 96(25), 7812 and the reaction can be carried out by the action of a ($C_1$–$C_4$)alkyl acid in the presence of sodium borohydride. Use may also be made of conventional N-alkylation reactions, for example by reacting the amino group with a ($C_1$–$C_4$)alkyl halide in the presence of dimethylformamide and potassium carbonate;

the compounds (I) in which $R_3$ represents a ($C_1$–$C_4$) alkoxy can be obtained from the corresponding compounds (Ip) in which $R'_3$=OH by a conventional O-alkylation reaction, for example by the action of a ($C_1$–$C_4$)alkyl halide in the presence of dimethylformamide and of caesium or potassium carbonate;

the compounds (I) in which $R_3$ represents a ($C_1$–$C_4$) alkylcarbonylamino group can be obtained from the corresponding compounds (I) in which $R_3$=—$NH_2$ by a conventional acylation, such as the action of a ($C_1$–$C_4$) alkyl acid chloride in the presence of a base, such as triethylamine, in a solvent, such as dichloromethane;

the compounds (I) in which $R_3$ represents a cyclic amine or a morpholin-4-yl can be obtained from the corresponding compounds (I) in which $R_3$=—$NH_2$ according to the method described in Tetrahedron, 1989, 45(3), 629–636.

the compounds of formula (I) in which $R_0$ represents a group:

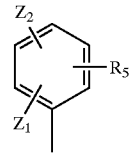

can be obtained from the corresponding compounds of formula (I) by conversion of the $R_5$ group according to conventional reactions, for example alkylation, acylation, oxidation, reduction or amination reactions, well known to a person skilled in the art.

The compounds (III) are prepared by dehalogenation of the compounds of formula:

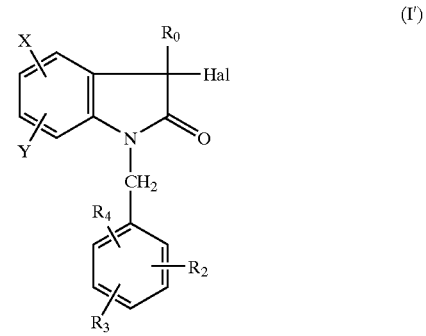

(I')

in which $R_0$, $R_2$, $R_3$, $R_4$, X and Y are as defined for (I) and Hal represents a chlorine, bromine or iodine atom, for example by the action of a hindered lithium dialkylamide, such as lithium diisopropylamide (LDA), by analogy with the method described by N. Newcom et al. in J. Am. Chem. Soc., 1990, 5186–5193.

The compound (I') is, for example, obtained by conversion of the corresponding compound (I) in which $R_1$=OH by the action of a halogenated derivative, for example of acid halide type. Mention may be made, as chlorinated derivative, of $SOCl_2$.

The compound (IV) is generally obtained by reaction of the compound (l) with the isatin derivative of formula:

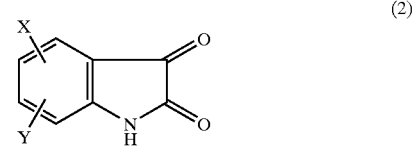

(2)

in which X and Y are as defined for (I), under the same conditions as those described above for the preparation of the compound (I) from the compound (II). The isatin derivatives (2) are commercially available compounds or are prepared according to the methods described in Tetrahedron Letters, 1998, 39, 7679–7682; Tetrahedron Letters, 1994, 35, 7303–7306; J. Org. Chem., 1977, 42, 1344–1348 and Advances in Heterocyclic Chemistry, A. R. Katritzky and A. J. Boulton, Academic Press, New York, 1975, 18, 2–58.

The compounds (II) can be synthesized according to various methods disclosed in particular in Patent Applications EP 526 348 and WO 95/18105.

Some routes for the production of the compounds (II) are illustrated in Scheme 2:

SCHEME 2

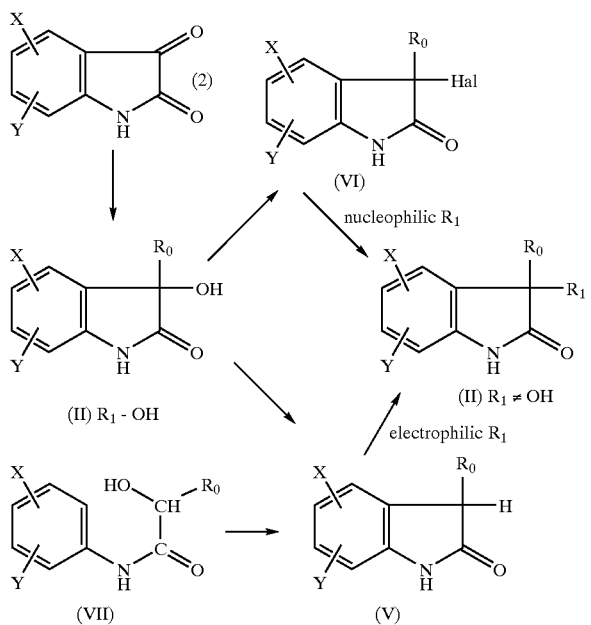

(II) $R_1$ - OH (II) $R_1 \neq$ OH

The term "nucleophilic $R_1$" is understood to mean a $(C_1-C_4)$ alkoxy group.

The compound (II) in which $R_1$ represents an electrophilic group, for example a $(C_1-C_4)$alkyl group, can be prepared from the compounds of formula:

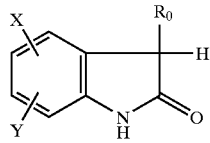
(V)

in which $R_0$, X and Y are as definded for (I), by reaction with a derivative $R_1$—Z in which Z represents a leaving group, under the same conditions as those described above for the transformation of the compound (III) to the compound (I).

The compound (V) is generally synthesized:
either by dehydroxylation of the corresponding compound (II) in which $R_1$=OH by the action of tin chloride in acidic medium, according to the method described in Tetrahedron, 1996, 52(20), 7003–7012, or by the action of triethylsilane, according to Bioorganic and Medicinal Letters, 1997, 7(10), 1255–1260;
or by a cyclization reaction in a strong acid medium, such as, for example, sulphuric acid, of the compound of formula:

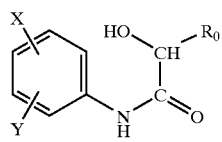
(VII)

in which $R_0$, X and Y are as defined for (I), this compound (VII) itself being obtained by a condensation reaction between an α-hydroxyacetic acid derivative of formula:

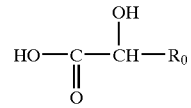
(VIII)

$R_0$ being as defined for (I), with an aminobenzene of formula:

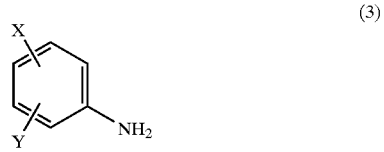
(3)

in which X and Y are as defined for (I).

The compounds (3) are commercially available or are conventionally synthesized.

The compounds of formula (VIII) are commercially available or are synthesized according to methods well known to a person skilled in the art. Reference may in particular be made to J. Med. Chem., 1987, 30(8), 1447.

Other reactions can also lead to the compounds (V). Mention may be made of:

the Brunner reaction described in Tetrahedron, 1986, 42(15), 4267–4272:

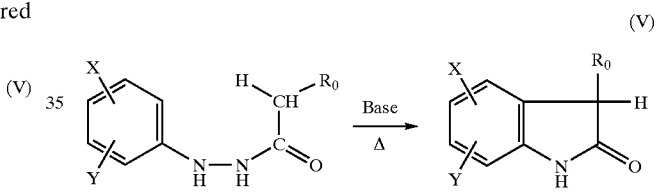
(V)

the cyclization reaction in the presence of formic acid described in J. Chem. Soc. Perkin Trans., 1986, 1, 349–360:

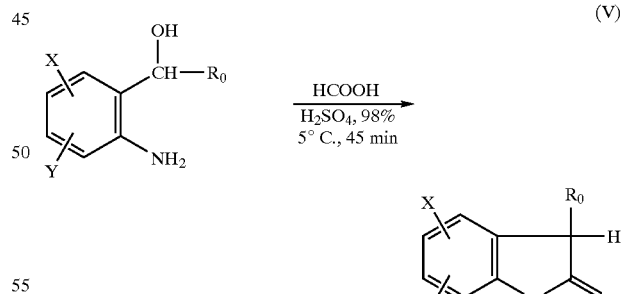
(V)

(V)

the following cyclization reactions:

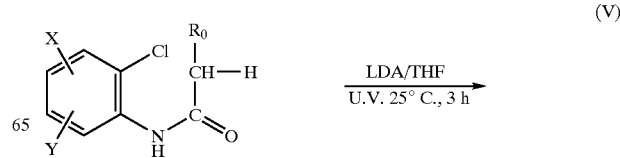
(V)

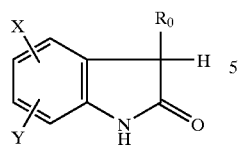

according to J. Am. Chem. Soc., 1985, 107(2), 435–443:

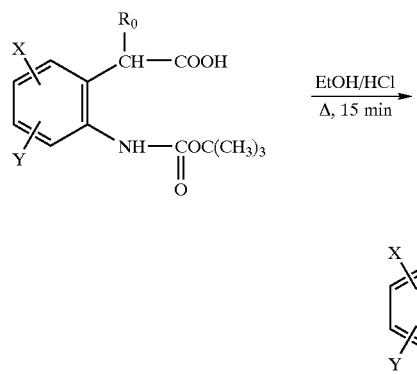

according to Tetrahedron, 1996, 52(20), 7003–7012.

The compounds (II) in which $R_1$ represents a ($C_1$–$C_4$) alkoxy group are obtained from the compounds of formula:

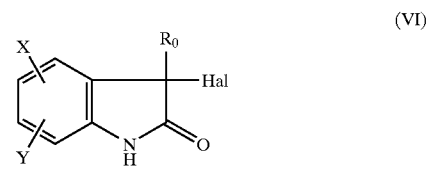

in which $R_0$, X and Y are as defined for (I) and Hal represents a halogen atom, for example a chlorine atom, by the action of the corresponding alcohol $R_1H$.

The compound (VI) is prepared from the corresponding compound (II) in which $R_1$=OH by reaction with thionyl chloride in the presence of pyridine in dichloromethane.

The compounds (II) in which $R_1$=OH are generally prepared from the corresponding isatin of formula:

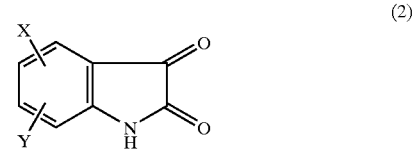

in which X and Y are as defined for (I), according to the method described above for the preparation of the compounds (I) in which $R_1$=OH from the compounds (IV).

When $R_1$ does not represent a hydroxyl group, the compounds (II) can also be prepared according to Scheme 3 below:

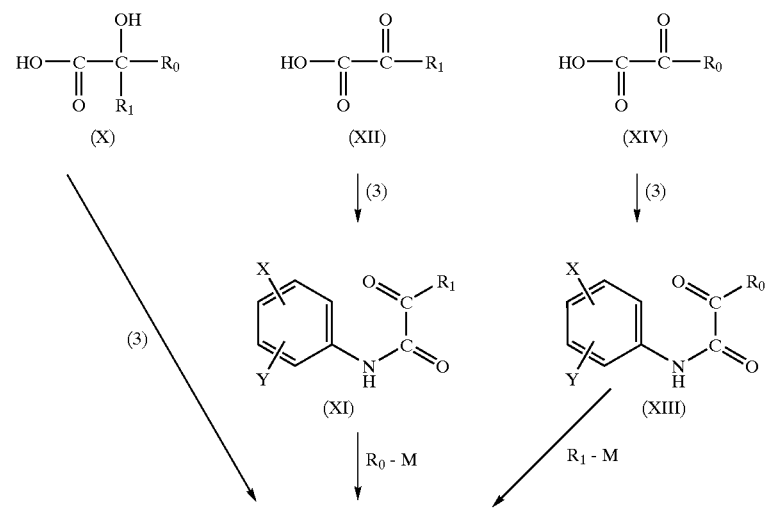

-continued

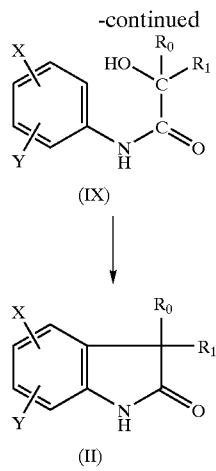

(IX)

↓

(II)

In this Scheme 3, $R_0$, $R_1$, X and Y are as defined for (I), $R_1$ does not represent a hydroxyl group and M represents, for example, a lithium atom or MgHal, Hal being a halogen atom.

The transformation of the compound (X) to the compound (IX) to give the compound (II) is carried out in particular according to the method described in J. Chem. Soc., 1957, 1928.

The benzyl halides (1) are known or are prepared according to known methods. Mention may be made, for example, of J. V. Rajanbabu, J. Org. Chem., 1986, 51, 1704–1712 and the publications cited in EP 636 609.

Generally, the halomethylbenzene derivatives (1) can be prepared by the action of N-halosuccinimides on the corresponding methylbenzene derivatives and according to EP 229 566. The reaction is carried out in a solvent, such as carbon tetrachloride, in the presence of dibenzoyl peroxide. A halomethylbenzene derivative can also be prepared from a corresponding hydroxymethylbenzene derivative by reaction with phosphorus tribromide in diethyl ether or by reaction with thionyl chloride.

At any stage in the process, an intermediate compound of (IIp), (IIIp) or (IVp) type, in which at least one of the substituents is replaced by one of its precursor groups, can be formed intermediately. These compounds (IIp), (IIIp) and (IVp) will be converted by conventional reactions into (II), (III) and (IV) respectively. A person skilled in the art will be in a position to adapt the abovementioned reactions to the compounds (IIp), (IIIp) and (IVp).

The compounds according to the invention have formed the subject of biochemical and pharmacological studies. The affinity of the compounds according to the invention for oxytocin receptors was determined in an in vitro binding test using the method described by J. Elands et al. in Eur. Pharmacol., 1987, 147, 192–207. This method consists in studying in vitro the displacement of a radioiodinated oxytocin analogue at the oxytocin receptors in a membrane preparation of human uterine oxytocin receptors. The $IC_{50}$ values (concentration which inhibits 50% of the binding of the radioiodinated oxytocin analogue to its receptors) are low and vary from $10^{-10}$ to $10^{-6}$ M in the latter test.

The affinity of the compounds according to the invention for human vasopressin $V_{1a}$ receptors (method described by M. Thibonnier et al. in J. Biol. Chem., 1994, 269, 3304–3310), $V_{1b}$ receptors (method described by T. Sugimoto et al. in J. Biol. Chem., 1994, 269, 27088–27092) and $V_2$ receptors (method described by M. Birnbaumer et al. in Nature (Lond.), 1992, 357, 333–335) has also been studied.

The compounds studied have little or no affinity for the $V_{1a}$, $V_{1b}$ and $V_2$ receptors. By way of indication, the compound of Example 1 exhibits an $IC_{50}$ of less than 50 nM, the $IC_{50}$ values with respect to the $V_{1a}$, $V_{1b}$ and $V_2$ receptors being greater than 1 μM.

The agonist or antagonist nature of the compounds is determined in vitro in a test for the measurement of intracellular calcium with respect to cells expressing human oxytocin receptors according to the general technique described in Am. J. Physiol., 268 (Heart Circ. Physiol., 37), 1995, H404–H410.

When the compounds according to the invention behave as antagonists, their $IC_{50}$ is advantageously between 0.5 μM and 0.5 nM. By way of example, the dextrorotatory enantiomer of Example 1 is an antagonist with an $IC_{50}$ of 3.2±1.9 nM.

The compounds according to the invention, powerful and selective ligands of oxytocin receptors, are particularly advantageous in the prevention and/or treatment of oxytocin-dependent disorders. The compounds according to the present invention can either mimic or inhibit the effects of oxytocin.

They will be particularly advantageous in cicatrization, in analgesia and anxiolysis (prevention of pain and anxiety), depression, schizophrenia, autism, obsessive compulsive syndrome, in maternal behaviour (facilitation of mother-child recognition and acceptance) and social behaviour, memory, regulation of food and drink intake, dependence on drugs, weaning and sexual motivation. They can be advantageously used in disorders of the urogenital sphere, in particular in the obstetric and gynaecological fields, in particular as uterine relaxant or tocolytic agent or for controlling contractions of the uterus before pregnancy has arrived at term, for controlling prenatal labour or for controlling preparatory labour for the purpose of a caesarean delivery, for solving problems of sterility or fertility, controlling births (in particular veterinary use), controlling oestrus, the halting of breast feeding, weaning, or embryo transfer and implantation; treating endometriosis, dysmenorrhoea and urinary stress or urgency incontinence, benign prostate hypertrophy and erectile dysfunctions, hypertension, hyponatraemia, cardiac insufficiency, atherosclerosis or angiogenesis, and regulating the storage of fat by the adipocyte.

Furthermore, given the role of oxytocin in controlling luteinizing hormone (J. J. Evans, J. Endocrin., 1996, 151, 169–174), the compounds of the invention can be used to induce contraception.

Furthermore, the compounds according to the invention can be used for their antitumour effects in oxytocin-secreting tumours, in particular breast and prostate cancers.

The use of the compounds according to invention for the prevention and/or the treatment of the abovementioned conditions and for the preparation of medicaments intended to treat these conditions forms an integral part of the invention.

Another subject-matter of the present invention is thus pharmaceutical compositions comprising a compound according to the invention or a pharmaceutically acceptable salt, solvate or hydrate of the latter and suitable excipients. The said excipients are chosen according to the pharmaceutical form and the method of administration desired: oral, sublingual, subcutaneous, intramuscular, intravenous, topical, intratracheal, intranasal, transdermal, rectal or intraocular. The pharmaceutical compositions are prepared according to techniques known to a person skilled in the art.

In order to obtain, the desired prophylactic or therapeutic effect, each unit dose can comprise from 0.5 to 1 000 mg, preferably from 1 to 500 mg, of active ingredients in combination with a pharmaceutical vehicle. This unit dose can be administered 1 to 5 times daily, so as to administer a daily dosage of 0.5 to 5 000 mg, preferably from 1 to 2 500 mg.

The compounds according to the invention can also be used for the preparation of compositions for veterinary use intended to regulate births.

The compounds according to the invention can also be used for the preparation of cosmetic compositions. These formulations can be provided in the form of a cream for topical use and will be intended to control lipolysis.

The compositions of the present invention can comprise, in addition to the products of formula (I) above or their pharmaceutically salts, solvates and hydrates, [lacuna] and for example active principles which may be of use in the treatment of the disorders or conditions indicated above. Thus, another subject-matter of the present invention is pharmaceutical compositions comprising several active principles in combination, one of which is a compound according to the invention. In particular, the present invention relates to pharmaceutical compositions comprising a compound according to the invention, an antagonist of oxytocin receptors, with a $V_{1a}$ antagonist compound. This type of composition will be of particular use in the treatment of dysmenorrhoea or endometriosis or the control of premature labour and for controlling preparatory labour for the purpose of a caesarean delivery.

Another subject-matter of the invention is products comprising an antagonist of oxytocin receptors as defined above and an antagonist of vasopressin $V_{1a}$ receptors for simultaneous or separate use or use spread out over time in the treatment of dysmenorrhoea or endometriosis or the control of premature labour and for controlling preparatory labour for the purpose of a caesarean delivery.

The following PREPARATIONS and EXAMPLES illustrate the invention without, however, limiting it.

The nuclear magnetic resonance spectra were recorded in deuterated chloroform, unless otherwise mentioned, at 200 MHz and the chemical shifts are expressed in ppm. The abbreviations used below are as follows: s=singlet; m=multiplet; d=doublet, t=triplet; q=quintet.

All the compounds according to the invention have formed the object of organic elemental analysis carried out by combustion at 1 000° C. in the presence of oxygen using a balance of Supermicro S4 Sartorius type and an elemental analyser of EA 1108 type. The percentage analyses of the elements carbon, hydrogen, nitrogen and sulphur obtained are in agreement with the theoretical results expected.

PREPARATIONS

Preparation 1

N-(4-Chlorophenyl)-2-oxopropionamide, Compound XI.1

26.3 g of 4-chlorophenylamine in 150 ml of dichloromethane and 35 ml of triethylamine are added, at −60° C., to 22 g of 2-oxopropionyl chloride (prepared according to Synthesis, 1975, 163–164 from 2-oxopropionic acid and 1,1-dichlorodimethyl ether) in 350 ml of dichloromethane. The reaction mixture is stirred at −60° C. for 2 hours and then 200 ml of a 0.15N aqueous hydrochloric acid solution and 500 ml of dichloromethane are added at −30° C. The organic phase is extracted, washed with a 0.25N aqueous hydrochloric acid solution and dried over sodium sulphate. The solvents are evaporated under reduced pressure and the residue obtained is crystallized from dichloromethane;

M.p.=151° C.

Preparation 2

2-(2-Chloro-4-fluorophenyl)-N-(4-chlorophenyl)-2-hydroxypropionamide, Compound IX.1

0.18 g of magnesium and 2.57 g of 2-chloro-4-fluoro-1-iodobenzene are stirred at reflux in 30 ml of diethyl ether. The mixture thus obtained is added at −60° C. to 0.99 g of compound XI.1 in 9 ml of tetrahydrofuran. The reaction mixture is stirred at 20° C. for 2 hours and then a saturated aqueous $NH_4Cl$ solution is added. Extraction is carried out with ethyl acetate, the organic phase is dried over $Na_2SO_4$ and the solvents are evaporated under reduced pressure. The residue obtained is purified by chromatography on a column of silica gel, elution being carried out with a 1/1 (v/v) cyclohexane/dichloromethane mixture and then a 99/1 (v/v) dichloromethane/methanol mixture. The solid thus isolated is crystallized from diisopropyl ether; M.p. 167° C.

The following compounds are prepared in the same way:

N-(4-Chlorophenyl)-2-(2,5-dimethoxyphenyl)-2-hydroxypropionamide, compound IX.2; M.p. 145° C.

N-(4-Chlorophenyl)-2-(2-chloro-4-methylphenyl)-2-hydroxypropionamide, compound IX.3; M.p. 116° C.

N-(4-Chlorophenyl)-2-(2-chloro-5-methylphenyl)-2-hydroxypropionamide, compound IX.4; M.p. 147° C.

N-(4-Chlorophenyl)-2-(2-chloro-5-fluorophenyl)-2-hydroxypropionamide, compound IX.5; M.p. 171° C.

Preparation 3

(2-Chlorophenyl)-N-(4-chlorophenyl) hydroxyacetamide, Compound VII.1

A mixture of 60 g of (2-chlorophenyl)hydroxyacetic acid and 41 g of 4-chlorophenylamine in 300 ml of 1,2-dichlorobenzene is heated to 200° C. The setup comprises a Dean and Stark apparatus and thus the water formed is removed during the reaction. Approximately 150 ml of solvent are distilled off and the expected compound is crystallized at 20° C. The solid obtained is rinsed with diisopropyl ether; M.p.=120° C.

In the same way, (2-chlorophenyl)-N-(4-methoxyphenyl) hydroxyacetamide, compound VII.2, is prepared from 4-methoxyphenylamine; M.p.=130° C.

In the same way, (2-chloro-4-fluorophenyl)-N-(4-chlorophenyl)hydroxyacetamide, compound VII.3, is prepared from (2-chloro-4-fluorophenyl)hydroxyacetic acid (synthesized according to J. Med. Chem., 1987, 30 (8), 1447, from 2-chloro-4-fluorobenzaldehyde and bromoform); M.p.=136° C.

Preparation 4

5-Chloro-3-(2-chlorophenyl)indolin-2-one, Compound V.1

(V.1):

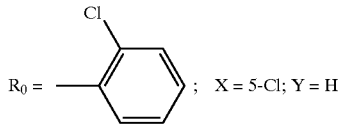
$R_0 =$ ; $X = 5\text{-Cl}; Y = H$

A solution of 263 ml of 95% sulphuric acid and 100 ml of 20% oleum is prepared at 10° C. This solution is stirred with 74 g of compound VII.1 for 2 hours at 40° C. The reaction mixture is subsequently cooled and then poured onto ice-cold water. The precipitate obtained is filtered off and then washed with 1 000 ml of water. The solid is dissolved in dichlorormethane and the solution thus obtained is washed successively with a saturated aqueous sodium hydrogencarbonate solution and with water and then dried over $Na_2SO_4$. The solvents are evaporated under reduced pressure and then the solid obtained is washed with diethyl ether; M.p.=201° C.

Compound V.2 below is prepared in the same way:

5-Chloro-3-(2-chloro-4-fluorophenyl)indolin-2-one, compound V.2.

(V.2):

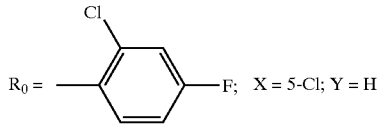
$R_0 =$ ——F; $X = 5\text{-Cl}; Y = H$

M.p.=221° C.

Preparation 5

5-Methoxy-3-(2-chlorophenyl)indolin-2-one, Compound V.3

20.1 g of 2-(2-chlorophenyl)-N-(4-methoxyphenyl)-2-hydroxyacetamide, compound VII.2, are added to a mixture of polyphosphoric acid, obtained from 65 ml of 85% phosphoric acid and 130 g of phosphorus pentoxide, at a temperature of 50° C. and then the reaction mixture is maintained at this temperature for 6 hours. After cooling, treatment is carried out with an aqueous sodium hydrogencarbonate solution until a pH of 5 is obtained. Extraction is carried out with ethyl acetate. The organic phase is washed with water and then dried over anhydrous sodium sulphate. The solvent is partially evaporated under reduced pressure and the expected product is filtered off; M.p.=179° C.

Preparation 6

5-Chloro-3-(2-chlorophenyl)-3-methylindolin-2-one, Compound II.1

(II.1):

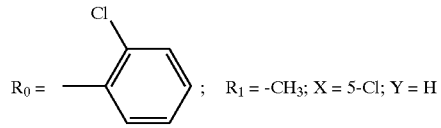
$R_0 =$ ; $R_1 = \text{-CH}_3; X = 5\text{-Cl}; Y = H$ 18.2 g of potassium tert-butoxide are added at −40° C. to a solution of 15 g of compound V.1 in 240 ml of tetrahydrofuran. The reaction mixture is stirred at 0° C. for 5 minutes and then a solution of 3.7 ml of methyl iodide in 80 ml of tetrahydrofuran is added at −60° C. Once the temperature of the reaction mixture has returned to 0° C., 100 ml of a saturated aqueous ammonium chloride solution are added and extraction is carried out with ethyl acetate. The organic phase is washed with water and then dried over anhydrous sodium sulphate. The solvents are evaporated under reduced pressure. The solid obtained is purified by chromotagraphy on a column of silica gel, elution being carried out with a 1/9 (v/v) ethyl acetate/cyclohexane mixture. The solid obtained is crystallized from n-pentane; M.p.=185° C.

Compounds II.2 to II.6 below are prepared in the same way.

(II)

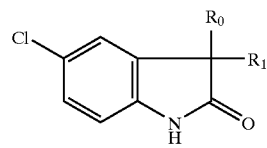

TABLE 1

| Compound | $R_0$ | $R_1$ | M.p.; ° C. |
|---|---|---|---|
| II.2 | ![Cl-phenyl] | $-CH_2-C\equiv CH$ | 219 |
| II.3 | ![Cl-phenyl] | $-CH_2-CH=CH_2$ | 218 |
| II.4 | ![Cl-phenyl] | $-CH_2CH_3$ | 198 |

TABLE 1-continued

| Compound | R₀ | R₁ | M.p.; °C. |
|---|---|---|---|
| II.5 | 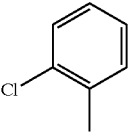 | —CH₂CH₂CH₃ | 218 |
| II.6 | 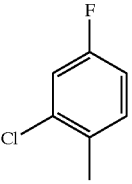 | —CH₃ | 189 |

5-Methoxy-3-(2-chlorophenyl)-3-methylindolin-2-one, compound II.7, is prepared according to the same procedure from 5-methoxy-3-(2-chlorophenyl)indolin-2-one; M.p.= 176° C.

Preparation 7

5-Chloro-3-(2-chloro-4-fluorophenyl)-3-methylindolin-2-one, Compound II.6

(II.6):

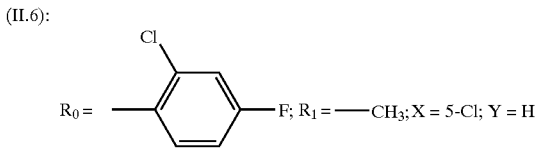

$R_0 =$ ...... —F; $R_1 =$ —CH₃; X = 5-Cl; Y = H

Compound II.6, described above, can also be prepared as follows:

0.3 g of compound IX.1 and a solution, prepared beforehand, of 5.3 g of phosphorus pentoxide in 3 ml of an 85% aqueous phosphoric acid solution are heated to 150° C. for 5 hours. The reaction mixture is poured onto ice, a saturated aqueous potassium carbonate solution is added and extraction is carried out with ethyl acetate. The organic phase thus obtained is dried over anhydrous sodium sulphate. The solvents are evaporated under reduced pressure. The solid obtained is crystallized from n-pentane; M.p.= 189° C.

The compound 5-chloro-3-(2,5-dimethoxyphenyl)-3-methylindolin-2-one, compound II.8;

(II.8):

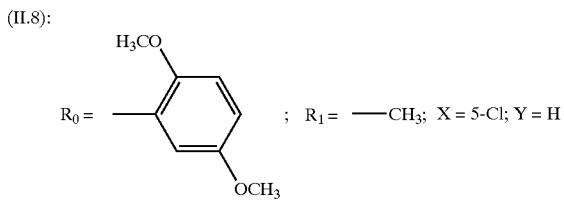

$R_0 =$ ...... ; $R_1 =$ —CH₃; X = 5-Cl; Y = H is prepared in the same way.
M.p.=163° C.

Preparation 8

5-Chloro-3-[2-chloro-5-(4-methyl-1-piperazinyl)phenyl]-3-methylindol-2-one, Compound II.9

(II.9):

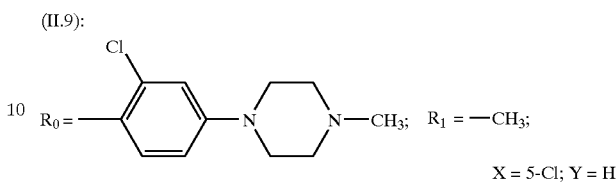

$R_0 =$ ...... —N⌒N—CH₃; $R_1 =$ —CH₃;

X = 5-Cl; Y = H

The mixture composed of 0.5 g of compound II.6, 2.5 ml of dimethyl sulphoxide, 3.6 ml of N-methylpiperazine, 1 g of sodium carbonate and 0.1 g of cuprous iodide is heated at 120° C. for 24 hours. After returning to room temperature, the salts are filtered off through talc and the precipitate is rinsed with dimethyl sulphoxide and then with 60 ml of ethyl acetate. The filtrate is washed with 40 ml of water and the organic phase is dried over anhydrous sodium sulphate. The solvents are evaporated under reduced pressure and the residue is purified by chromatography on a column of silica gel, elution being carried out with dichloromethane. The expected product is isolated after taking up the solid residue in diisopropyl ether and then filtering; M.p.=155° C.

Preparation 9

5-Chloro-3-(2-chloro-4-fluorophenyl)-3-hydroxyindolin-2-one, Compound II.10

(II.10):

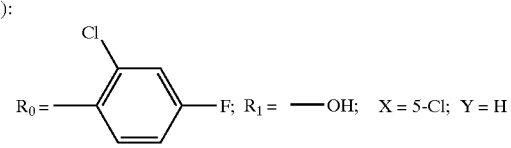

$R_0 =$ ...... —F; $R_1 =$ —OH; X = 5-Cl; Y = H 0.44 g of a 60% dispersion of sodium hydride in oil is added at −40° C. to a cooled suspension of 2 g of 5-chloroindolin-2,3-dione in 60 ml of tetrahydrofuran and the reaction mixture is stirred at 0° C. for 15 minutes. 0.45 g of magnesium and 4.23 g of 2-chloro-4-fluoro-1-iodobenzene in 18 ml of diethyl ether are stirred at reflux for 3 hours. The solution thus obtained is slowly added at −60° C. to the reaction mixture. The reaction mixture is stirred for 30 minutes at 20° C. and a saturated aqueous ammonium chloride solution is added. Extraction is carried out with ethyl acetate, the organic phase is dried over anhydrous sodium sulphate and the solvents are evaporated under reduced pressure. The residue obtained is purified by chromatography on a column of silica gel, elution being carried out with dichloromethane and then with a 95/5 (v/v) dichloromethane/methanol mixture. The solid obtained is crystallized from n-pentane; M.p.=239° C.

In the same way, 5-chloro-3-(2,5-dimethoxyphenyl)-3-hydroxyindolin-2-one, compound II,11;

(II.11):

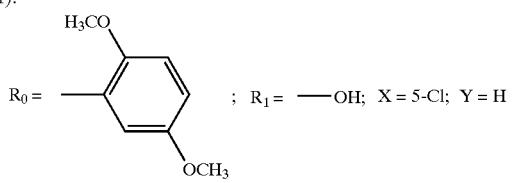

is prepared from 1-bromo-2,5-dimethoxybenzene.

M.p.=221° C.

Preparation 10

3,5-Dichloro-3-(2,5-dimethoxyphenyl)indolin-2-one, Compound VI.1

(VI.1)

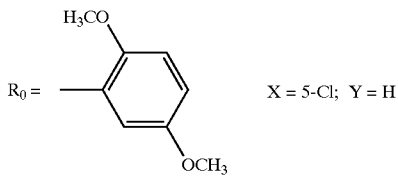

0.8 ml of thionyl chloride is added, at a temperature of less than 20° C., to 3 g of compound II.11 in the presence of 1.2 ml of pyridine in 50 ml of dichloromethane and then the reaction mixture is stirred for one hour. The reaction mixture is washed with water and dried over anhydrous sodium sulphate. The solvents are evaporated under reduced pressure and then the residue is chromatographed on a column of silica gel, elution being carried out with dichloromethane. M.p.=157° C.

The following compounds are prepared in the same way:

3,5-Dichloro-3-(2-chlorophenyl)indolin-2-one, compound VI.2.

(VI.2)

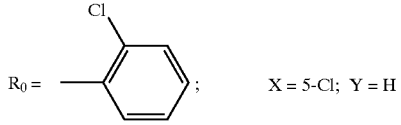

M.p.=190° C.

3,5-Dichloro-3-(2-chloro-4-fluorophenyl)indolin-2-one, compound VI.3.

(VI.3):

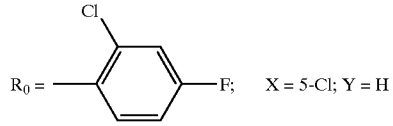

M.p.=87° C.

Preparation 11

5-Chloro-3-(2,5-dimethoxyphenyl)-3-methoxyindolin-2-one, Compound II.11

(II.11):

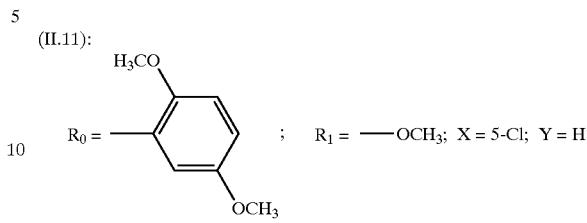

0.4 g of compound VI.1 in the presence of 25 ml of methanol in 50 ml of tetrahydrofuran is maintained at reflux for 3 hours. The solvents are evaporated under reduced pressure. M.p.=180° C.

The following compounds are prepared in the same way:

5-Chloro-3-(2-chlorophenyl)-3-methoxyindolin-2-one, compound II.12.

(II.12):

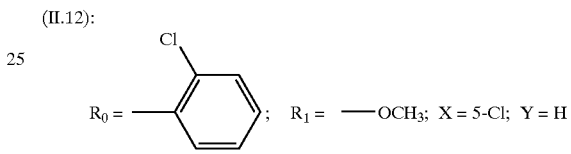

M.p.=179° C.

5-Chloro-3-(2-chloro-4-fluorophenyl)-3-methoxyindolin-2-one, compound II.13.

(II.13):

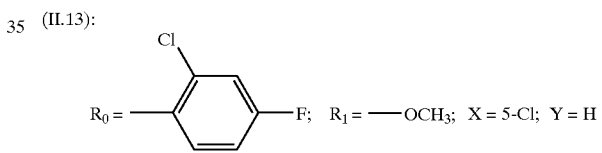

M.p.=82° C.

Preparation 12

5-Chloro-1-(2,4-dimethoxybenzyl)indolin-2,3-dione, Compound IV.1

(IV.1.):$R_2$=H; $R_3$=4-OCH$_3$; $R_4$=2-OCH$_3$; X=5-Cl; Y=H a) 0.25 ml of phosphorus tribromide is added at −50° C. to a suspension of 1.45 g of 2,4-dimethoxyphenylmethanol in 25 ml of diethyl ether. The solution thus obtained is allowed to return to a temperature of 0° C.

b) 2 g of potassium tert-butoxide are added at −60° C. to a suspension of 1.3 g of 5-chloroindolin-2,3-dione in 50 ml of tetrahydrofuran. The reaction mixture is stirred at 0° C. for 5 minutes and then the solution prepared in a) is added at −60° C. The reaction mixture is stirred at room temperature for 16 hours and then the solvents are evaporated under reduced pressure. The residue obtained is purified by chromatography on a column of silica gel, elution being carried out with a cyclohexane/dichloromethane mixture varying from 8/2 to 2/8 (v/v). The solid obtained is crystallized from toluene; M.p.=175° C.

The following compounds are prepared in the same way:

5-Chloro-1-(4-chloro-2-methoxybenzyl)indolin-2,3-dione, Compound IV.2.

M.p.=136° C.

5,7-Dichloro-1-(2,4-dimethoxybenzyl)indolin-2,3-dione, Compound IV.3.

M.p.=171° C.

5-Fluoro-1-(2,4-dimethoxybenzyl)indolin-2,3-dione, Compound IV.4.

M.p.=163° C.

1-(2,4-Dimethoxybenzyl)indolin-2,3-dione, Compound IV.5.

M.p.=142° C.

Example 1

5-Chloro-3-(2-chlorophenyl)-1-(2,4-dimethoxybenzyl)-3-methylindolin-2-one (I):

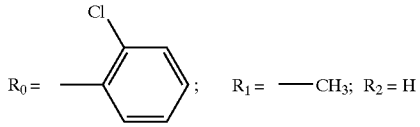

a) 0.48 ml of phosphorus tribromide is added at −50° C. to a suspension of 2.6 g of 2,4-dimethoxyphenylmethanol in 45 ml of diethyl ether. The solution thus obtained is allowed to return to a temperature of 0° C.

b) 1.2 g of potassium tert-butoxide are added at −40° C. to 3 g of compound II.1 in solution in 90 ml of tetrahydrofuran and then the reaction mixture is stirred until the temperature has returned to 0° C. The reaction mixture is subsequently cooled to −60° C. and the solution prepared in a) is added. The reaction mixture is stirred at 20° C. for 2 hours, 50 ml of water are added and extraction is carried out with ethyl acetate. The organic phases are dried over sodium sulphate and the solvents are evaporated under reduced pressure. The solid obtained is crystallized from diisopropyl ether; M.p.=179° C.

This compound, in the racemic form, is then separated by chromatography on a Chiralpak® AD column from Daicel, elution being carried out with a 98/2 (v/v) 2-methylpentane/ethanol mixture.

The dextrorotatory enantiomer: M.p.=92° C.; $[\alpha]_D^{23.5}$=+39° (c=1, CH$_3$OH), and its antipode are thus isolated.

Example 2

5-Methoxy-3-(2-chlorophenyl)-1-(2,4-dimethoxybenzyl)-3-methylindolin-2-one (I):

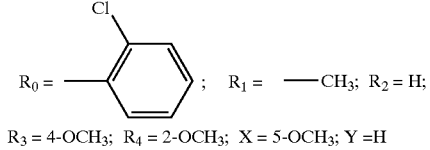

The compound of Example 2 is prepared according to the same procedure from 5-methoxy-3-(2-chlorophenyl)indolin-2-one, compound II.7;

M.p.=133° C.

Example 3

5-Chloro-3-(2-chlorophenyl)-1-[4-(1,1-dimethylethoxy)-2-methoxybenzyl]-3-methylindolin-2-one (I):

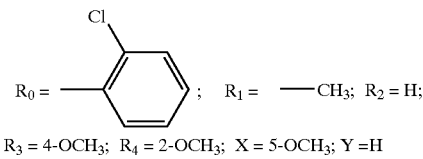

a) Preparation of [4-(1,1-dimethylethoxy)-2-methoxy]phenylmethanol

Preparation of methyl [4-(1,1-dimethylethoxy)-2-methoxy]benzoate according to J. Org. Chem., 1986, 51, 111–113.

0.25 ml of trifluoromethanesulphonic acid is added at −70° C. to 6.2 g of methyl 4-hydroxy-2-methoxybenzoate (according to J. Med. Chem., 1985, 28, 717–727, from commercial methyl 2,4-dihydroxybenzoate) in 60 ml of dichloromethane and then 25 ml of 2-methylpropene, condensed beforehand at −20° C. and degassed by natural rewarming, are added by means of a dip pipe. After stirring for 24 hours at a temperature of between −30 and −70° C., 0.5 ml of triethylamine is added to the reaction mixture. The solvents are evaporated under reduced pressure and the residue is taken up in ethyl acetate and washed with a dilute sodium bicarbonate solution. The separated organic phase is dried over anhydrous sodium sulphate and the solvents are evaporated under reduced pressure. The expected product is isolated, purification being carried out by chromatography on a column of silica gel, elution being carried out with cyclohexane.

$^1$H NMR: 7.75 (d, 1H), 6.62–653 (m, 2H), 3.85 (s, 3H), 3.84 (s, 3H), 1.40 (s, 9H).

According to J. Chem. Soc. Perkin Trans., 1991, 3291–3294.

15.90 ml of a 2M solution of LiBH$_4$ in tetrahydrofuran are added to 2.5 g of the preceding compound obtained in a) in 25 ml of toluene. The reaction mixture is heated at 100° C. for 45 minutes. At approximately 20° C., the reaction mixture is poured onto a water/ice mixture and the aqueous phase is extracted with ethyl acetate. After separating by settling, the aqueous phase is extracted with ethyl acetate. The organic phases are combined and dried over anhydrous sodium sulphate and then the solvents are evaporated under reduced pressure.

$^1$H NMR: 7.10 (d, 1H), 6.59–6.50 (m, 2H), 4.61 (d, 2H), 3.81 (s, 3H), 2.20 (t, 1H), 1.34 (s, 9H).

b) The compound of Example 3 is prepared according to the same procedure as for Example 1; M.p.=131° C.

Example 4

5-Chloro-3-p(2-chorophenyl)-1-[4-(-methylethoxy)-2-methoxybenzyl]-3-methylindolin-2-one (I):

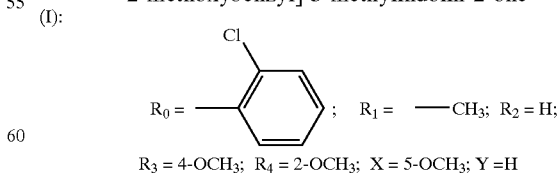

a) Preparation of [4-(1-methylethoxy)-2-methoxy]phenylmethanol.

Preparation of methyl [4-(1-methylethoxy)-2-methoxy]benzoate according to Synthesis, 1988, 712.

2.86 g of caesium carbonate and then 1.28 ml of 2-iodopropane are added at 0° C. to 0.8 g of methyl 4-hydroxy-2-methoxybenzoate in 20 ml of dimethylformamide. The reaction mixture is stirred at 20° C. for 2 hours, 50 ml of water are then added and extraction is carried out with ethyl acetate. The organic phase is washed with water and then dried over anhydrous sodium sulphate. The solvents are evaporated under reduced pressure.

$^1$H NMR: 7.81 (d, 1H), 6.47–6.42 (m, 2H), 4.69–4.51 (m, 1H), 3.85 (s, 3H), 3.83 (s, 3H), 1.33 (d, 6H).

[4-(1-Methylethoxy)-2-methoxyphenyl]methanol is prepared according to the method described above in Example 3 for the transformation of methyl [4-(1,1-dimethylethoxy)-2-methoxy]benzoate into [4-(1,1-dimethylethoxy)-2-methoxy]phenylmethanol.

b) The compound of Example 4 is prepared according to the procedure described for Example 1;
M.p.=158° C.

Examples 5 to 17 below are prepared according to the procedure described for Example 1.

Example 5

5-Chloro-3-(2-chlorophenyl)-1-(2-methoxy-4-nitrobenzyl)-3-methylindolin-2-one (I):

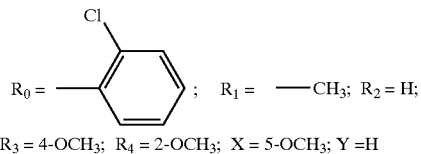

$R_0 = $ (2-chlorophenyl); $R_1 = $ —CH$_3$; $R_2 = $ H;
$R_3 = $ 4-OCH$_3$; $R_4 = $ 2-OCH$_3$; X = 5-OCH$_3$; Y = H M.p.=179° C.

Example 6

5-Chloro-1-(2,4-dimethoxybenzyl)-3-(2,5-dimethoxyphenyl)-3-methylindolin-2-one (I):

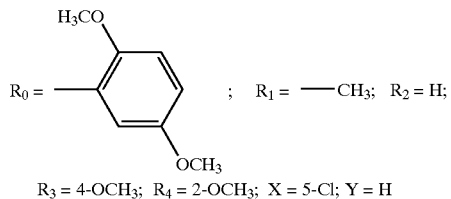

$R_0 = $ ; $R_1 = $ —CH$_3$; $R_2 = $ H;
$R_3 = $ 4-OCH$_3$; $R_4 = $ 2-OCH$_3$; X = 5-Cl; Y = H

M.p.=140° C. (0.3 H$_2$O)

TABLE 2

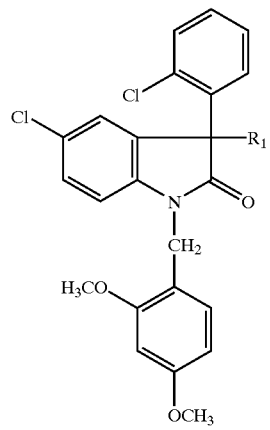

(I)

| EXAMPLE | $R_1$ | M.p.; ° C.; salt, hydrate |
|---|---|---|
| 7 | —CH$_2$—C≡CH | 135 |
| 8 | —CH$_2$—CH=CH$_2$ | 117 |
| 9 | —CH$_2$CH$_3$ | 102 |
| 10 | —CH$_2$CH$_2$CH$_3$ | 119 |

TABLE 3

(I)

| EXAMPLE | $R_0$ | $R_4$ | M.p.; ° C. |
|---|---|---|---|
| 11 | 2-chlorophenyl | 2-OCH$_3$ | 155 |
| 12 | 2-chlorophenyl | 3-OCH$_3$ | 150 |
| 13 | 2-methoxyphenyl | 2-OCH$_3$ | 121 |

TABLE 3-continued

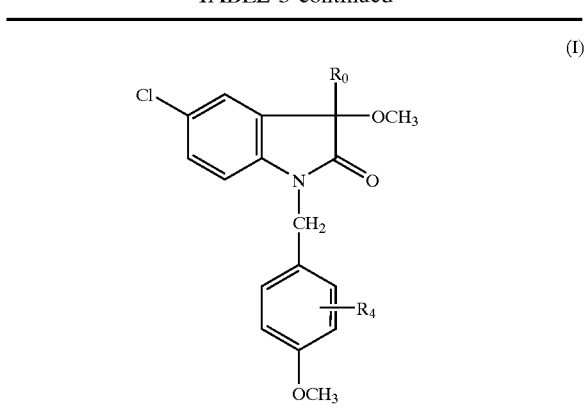

| EXAMPLE | R₀ | R₄ | M.p.; °C. |
|---|---|---|---|
| 14 | (2-chloro-4-fluorophenyl) | 2-OCH₃ | wax |

TABLE 4

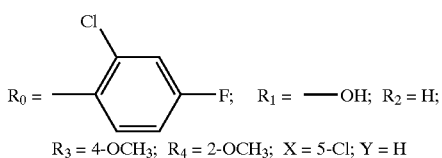

| EXAMPLE | R₀ | M.p.; °C. |
|---|---|---|
| 15 | (2-chloro-4-methylphenyl) | 112 |
| 16 | (2-chloro-5-methylphenyl) | 168 |
| 17 | (2-chloro-5-fluorophenyl) | 113 |

Example 18

5-Chloro-3-(2-chloro-4-fluorophenyl)-1-(2,4-dimethoxybenzyl)-3-hydroxyindolin-2-one (I):

$R_0 =$ (2-chloro-4-fluorophenyl); $R_1 =$ —OH; $R_2 = H$;

$R_3 = 4$-OCH₃; $R_4 = 2$-OCH₃; $X = 5$-Cl; $Y = H$

This compound can be prepared from compound II.10 according to the same procedure as for Example 1 or else according to the method below:

0.87 ml of 2-chloro-4-fluoro-1-iodobenzene and 0.09 g of magnesium in 15 ml of diethyl ether are stirred at reflux for 1 hour. 0.75 g of compound IV.1, in partial solution in 15 ml of tetrahydrofuran, is added at −40° C. The reaction mixture is stirred for 2 hours at 20° C. and then a saturated aqueous ammonium chloride solution is added. Extraction is carried out with ethyl acetate, the organic phase is dried over anhydrous sodium sulphate and then the solvents are evaporated under reduced pressure. The residue obtained is purified by chromatography on a column of silica gel, elution being carried out with a 1/1 (v/v) cyclohexane/dichloromethane mixture. The solid obtained is crystallized from cyclohexane; M.p.=177° C.

This compound, in the racemic form, is separated by chromatography on a Chiralpak® AD column from Daicel, elution being carried out with a 9/1 (v/v) 2-methylpentane/ethanol mixture.

The dextrorotatory enantiomer:

$[\alpha]_D^{20.5} = +63°$ ($c = 1$, CH₃OH), and its antipode are thus isolated.

Example 19

5-Chloro-3-(2-chloro-5-methoxymethoxymethylphenyl)-1-(2,4-dimethoxybenzyl)-3-hydroxyindolin-2-one (I):

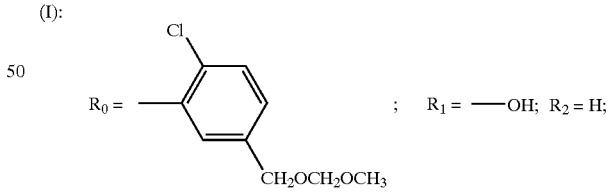

; $R_1 =$ —OH; $R_2 = H$;

$R_3 = 4$-OCH₃; $R_4 = 2$-OCH₃; $X = 5$-Cl; $Y = H$ a) Preparation of 2-chloro-1-iodo-5-hydroxymethylbenzene according to J. Org. Chem., 1991, 56, 5964–5965, from the corresponding commercial benzoic acid.

5.02 g of sodium borohydride are added portionwise and then 14.6 g of iodine, in solution in 50 ml of tetrahydrofuran, are added very slowly to 25 g of 4-chloro-3-iodobenzoic acid in solution in 200 ml of tetrahydrofuran at 0° C. The reaction mixture is stirred for 2 hours at room temperature and then at 35° C. for 30 minutes. Hydrolysis is carried out at 10° C. with a 0.5N hydrochloric acid solution and extraction is carried out with ethyl acetate. The organic phase is separated by settling and then treated with an aqueous sodium bisulphite solution and then with water. The organic phase is dried over anhydrous sodium sulphate and the solvents are evaporated under reduced pressure. The expected compound is obtained by distillation;

B.p.=109° C. under 3 Pa.

b) Preparation of 2-chloro-1-iodo-5-methoxymethyleneoxymethylbenzene according to Synthesis, 1985, 74.

1.5 ml of para-toluenesulphonic acid monohydrate and 1.4 g of lithium bromide are added to 24.45 g of the preceding compound in 100 ml of dimethoxymethane. The reaction mixture is stirred at 35° C. for 4 hours and then for 2 hours at reflux. Hydrolysis is carried out at room temperature with a dilute aqueous sodium bicarbonate solution and extraction is carried out with diethyl ether. The organic phase is washed with water and dried over anhydrous sodium sulphate and the solvents are evaporated under reduced pressure. The expected product is obtained by distillation; B.p.=108° C. under 1.9 Pa.

c) The compound of Example 19 is prepared according to the procedure described for Example 18;

M.p.=142° C.

Example 20

Methyl 4-Chloro-3-[5-chloro-1-(2,4-dimethoxybenzyl)-3-hydroxy-2-oxoindolin-3-yl]benzoate (I):

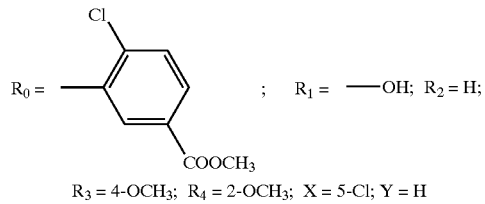

$R_3 = 4\text{-OCH}_3$; $R_4 = 2\text{-OCH}_3$; $X = 5\text{-Cl}$; $Y = H$ 45.2 ml of a 1.6M solution of n-butyllithium in hexane, diluted in 200 ml of tetrahydrofuran and cooled to −90° C., are slowly added to 10.72 g of methyl 4-chloro-3-iodobenzoate (prepared by esterification of the corresponding commercial acid; M.p.=56° C.) in 200 ml of tetrahydrofuran cooled to −100° C. The reaction mixture is stirred at −95° C. for 20 minutes and then the solution, cooled to −70° C., of 10 g of compound IV.1 in 600 ml of tetrahydrofuran is added. After returning to room temperature, hydrolysis is carried out with 200 ml of a saturated ammonium chloride solution, the solvents are partially evaporated under reduced pressure, extraction is carried out with ethyl acetate, the organic phase is dried over anhydrous sodium sulphate and then the solvents are evaporated under reduced pressure. The residue obtained is washed with diethyl ether, filtered off and then dried at 5° C. under reduced pressure; M.p.=236° C.

Example 21

3-(5-Amino-2-chlorophenyl)-5-chloro-1-(2,4-dimethoxybenzyl)-3-hydroxyindolin-2-one (I):

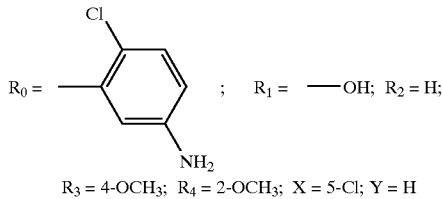

$R_3 = 4\text{-OCH}_3$; $R_4 = 2\text{-OCH}_3$; $X = 5\text{-Cl}$; $Y = H$ a) Preparation of 4-chloro-3-bromo-N,N-(tetramethylethylene)disilylaniline A mixture composed of 3.3 g of 3-bromo-4-chloroaniline, 3.72 g of bis(dimethylaminodimethyl-silyl)ethylene, obtained according to Tetrahedron Letters, 1984, 25 (12), 1253–1254, and 0.03 g of zinc iodide is heated at 140° C. for 5 hours under an argon stream. The expected product is distilled; B.p.=105° C. under 37 Pa.

b) The compound of Example 21 is prepared according to the same procedure described for Example 20, purification being carried out by chromatography on a column of silica gel, elution being carried out with a 99/1 (v/v) dichloromethane/methanol mixture;

M.p.=133° C.

The compounds of Examples 22 to 31 below are prepared in the same way as for Example 18:

TABLE 5

(I)

| EXAMPLE | R₀ | M.p; ° C.; salt, hydrate |
|---|---|---|
| 22 | ![structure with Cl and F on benzene] | 156 |
| 23 | ![structure with Cl and F on benzene] | 185 |

TABLE 5-continued (I) [Structure: 5-chloro-3-hydroxy-1-(2-methoxy-4-methoxybenzyl)indolin-2-one with R₀ at 3-position]

| EXAMPLE | R₀ | M.p; °C.; salt, hydrate |
|---|---|---|
| 24 | 4-Cl, 3-CH₃-phenyl | 190; 0.7 H₂O |
| 25 | 3-Cl, 4-CH₃-phenyl | 207 |
| 26 | 2,6-diCl, 3-CH₃(?)-phenyl | 198 |
| 27 | 2,3-diCl-phenyl | 186 |
| 28 | 2,4-diCl, 3-CH₃-phenyl (?) | 196 |
| 29 | 3,4-diCl-phenyl | 199 |
| 30 | 2-Cl-phenyl | 161 |
| 31 | 2-CH₃-phenyl | 148 |

Example 32

5,5-Chloro-1-(2,4-dimethoxybenzyl)-3-[5-(1,3-dioxolan-2-yl)-2-methoxyphenyl]-3-hydroxyindolin-2-one (I): R₀ = [3-(1,3-dioxolan-2-yl)-4-methoxyphenyl]; R₁ = —OH; R₂ = H; R₃ = 4-OCH₃; R₄ = 2-OCH₃; X = 5-Cl; Y = H a) Preparation of 2-(3-bromo-4-methoxyphenyl)-1,3-dioxolane according to J. Med. Chem., 1990, 33(3), 972.

A mixture composed of 5 g of 3-bromo-para-anisaldehyde, 5 ml of ethylene glycol, 0.088 g of para-toluenesulphonic acid and 125 ml of toluene is heated at reflux for 1 hour 30 minutes in a reactor equipped with a Dean and Stark apparatus. The reaction mixture is poured at room temperature onto 50 ml of water, extraction is carried out with diethyl ether and the organic phase is dried over anhydrous sodium sulphate. The solvents are evaporated under reduced pressure. The oil obtained is purified by chromatography on a column of silica gel, elution being carried out with an 8/2 (v/v) cyclohexane/ethyl acetate mixture. The expected product is obtained after distillation under reduced pressure; B.p.=128° C. under 5 Pa.

b) The compound of Example 32 is prepared from the preceding compound according to the procedure described for Example 18; M.p.=140° C.

Example 33

5-Chloro-1-(2,4-dimethoxybenzyl)-3-{5-[(dimethylamino)-methyl]-2-methoxyphenyl}-3-hydroxyindolin-2-one (I):

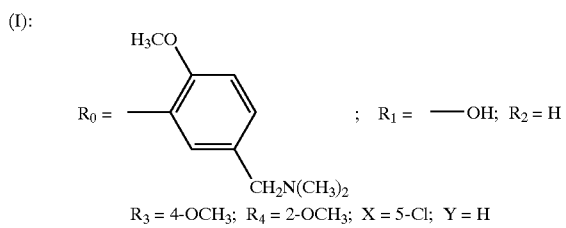

$R_3 = 4\text{-OCH}_3$; $R_4 = 2\text{-OCH}_3$; $X = 5\text{-Cl}$; $Y = H$ a) 3-[5-Chloro-1-(2,4-dimethoxybenzyl)-3-hydroxy-2-oxoindolin-3-yl]-4-methoxybenzaldehyde, obtained by deprotection of the compound of Example 32 in acidic medium according to J. Chem. Soc. Chem. Commun., 1987, 1351.

The mixture composed of 0.55 g of the compound of Example 32, 5 ml of acetone, 2.5 ml of water and 0.22 ml of 1N hydrochloric acid is brought to 30° C. for 2 hours with stirring. The reaction mixture is neutralized at room temperature with an aqueous sodium bicarbonate solution and extraction is carried out with ethyl acetate. The organic phase is dried over anhydrous sodium sulphate, the solvents are evaporated under reduced pressure and the desired compound is obtained by filtration of the evaporation residue taken up in diethyl ether; M.p.=189° C.

b) Reductive amination according to J. Org. Chem., 1996, 61(11), 3849–3862.

0.015 g of dimethylamine, in solution in 1 ml of 1,2-dichloroethane, and then 0.072 g of sodium triacetoxyborohydride are added to 0.113 g of the preceding compound obtained in a) in suspension in 3 ml of 1,2-dichloroethane. After stirring for 15 hours at room temperature, hydrolysis is carried out with 10 ml of water and extraction is carried out with ethyl acetate. The organic phase is dried over sodium sulphate, the solvents are evaporated under reduced pressure and the residue obtained is purified by chromatography on a column of silica gel, elution being carried out with a 95/5 (v/v) dichloromethane/methanol mixture. The expected product is obtained after crystallization from isopropyl ether; M.p.=162° C. (0.4H$_2$O).

Example 34

5-Chloro-3-(3-chloropyridin-4-yl)-1-(2,4-dimethoxy-benzyl)-3-hydroxyindolin-2-one

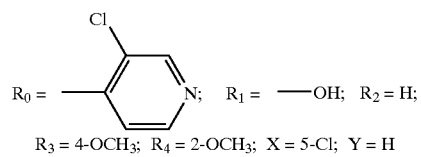

$R_3 = 4\text{-OCH}_3$; $R_4 = 2\text{-OCH}_3$; $X = 5\text{-Cl}$; $Y = H$

A solution of 0.414 ml of 3-chloropyridine in 5 ml of tetrahydrofuran is added dropwise to a solution, diluted in 7 ml of tetrahydrofuran and cooled to −75° C., of 2.88 ml of 1.5 M lithium diisopropylamide in cyclohexane. After the addition, the reaction mixture is stirred at −75° C. for 20 minutes and then 1.2 g of compound IV.1 in 15 ml of tetrahydrofuran are added. The temperature of the reaction mixture is allowed to slowly rise to 0° C. and then hydrolysis is carried out with 30 ml of an aqueous ammonium chloride solution. Extraction is carried out with ethyl acetate and the organic phase is dried over sodium sulphate. The solvents are evaporated under reduced pressure and the residue obtained is purified by chromatography on a column of silica gel, elution being carried out with a 75/25 (v/v) cyclohexane/ethyl acetate mixture. The solid obtained is subsequently crystallized from ethyl acetate; M.p.=215° C.

The compounds of Examples 35 and 36 below are prepared in the same way:

TABLE 6

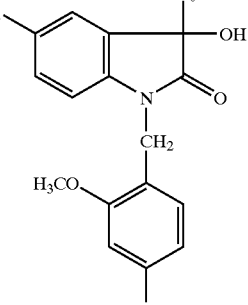

(I)

| EXAMPLE | R$_0$ | M.p.; ° C.; salt, hydrate |
|---|---|---|
| 35 | 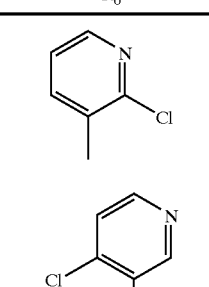 | 210 |
| 36 | 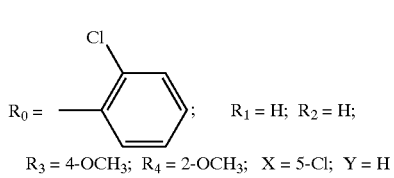 | 215 |

Preparation 13

5-Chloro-3-(2-chlorophenyl)-1-(2,4-dimethoxybenzyl)indolin-2-one, Compound III.1

(III.1):

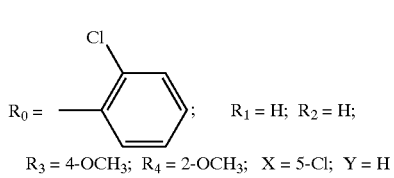

$R_0 =$ ; $R_1 = H$; $R_2 = H$;

$R_3 = 4\text{-OCH}_3$; $R_4 = 2\text{-OCH}_3$; $X = 5\text{-Cl}$; $Y = H$ a) 3,5-Dichloro-3-(2-chlorophenyl)-1-(2,4-dimethoxybenzyl)indolin-2-one, compound I'.1.

0.98 ml of thionyl chloride is added at −20° C. to a solution of 2 g of the compound of Example 30 and 1.4 ml of pyridine in 24 ml of dichloromethane. The reaction mixture is stirred for 1 hour 30 min at room temperature and is cooled to 0° C. and then 50 ml of water and 50 ml of dichloromethane are added. Separation is carried out by settling, the organic phase is washed with an aqueous $NaHCO_3$ solution and dried over anhydrous sodium sulphate, and the solvent is evaporated under reduced pressure. The residue obtained is dried under reduced pressure for 2 hours and compound I'.1 is isolated in the form of a resin which is used directly in the following stage.

b) Compound III.1

6.53 ml of a 1.5M solution of lithium diisopropylamide in cyclohexane, rediluted with 15 ml of tetrahydrofuran, are added at −68° C. to the solution of compound I'.1 obtained above in 24 ml of tetrahydrofuran. The reaction mixture is stirred for 45 minutes at −68° C. and then 5 ml of methanol are slowly added. At approximately 0° C., water is added and extraction is carried out with ethyl acetate. The organic phase is washed with an aqueous sodium chloride solution and dried over sodium sulphate and the solvent is evaporated under reduced pressure. The residue obtained is purified by chromatography on a column of silica gel, elution being carried out with an 85/15 (v/v) cyclohexane/ethyl acetate mixture. The expected product is isolated after crystallization from isopropyl ether; M.p.=151° C. ($0.2H_2O$).

Compounds III.2 to III.8 below are prepared in the same way:

TABLE 7

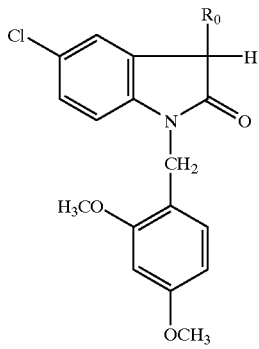

(I')

| Compound | $R_0$ | M.p.; ° C.; (solvate) |
|---|---|---|
| III.2 | 2-methoxyphenyl (H₃CO, ortho-methyl) | 142 |
| III.3 | 2,4-dichloro-substituted phenyl with methyl | 175; 0.7 $H_2O$ |
| III.4 | 4-fluoro-2-chloro-substituted phenyl with methyl | 156 |
| III.5 | 4-chloro-phenyl with $CH_2OCH_2OCH_3$ and methyl | 136 |
| III.6 | 4-chloro-phenyl with $COOCH_3$ and methyl | 165 |
| III.7 | 4-chloro-phenyl with $NH_2$ and methyl | 128 |
| III.8 | 2-methylphenyl ($H_3C$, ortho-methyl) | 151 |

Example 37

5-Chloro-3-(2-chloro-4-fluorophenyl)-1-(2,4-dimethoxybenzyl)-3-methylindolin-2-one

(I):

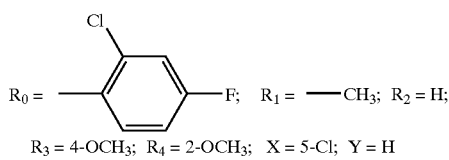

$R_3$ = 4-OCH$_3$; $R_4$ = 2-OCH$_3$; X = 5-Cl; Y = H 0.34 g of potassium tert-butoxide is added at −40° C. to a solution of 1.14 g of compound III.4 in 20 ml of tetrahydrofuran. The reaction mixture is stirred at 0° C. for 5 minutes and then 0.32 ml of methyl iodide is added at −40° C. The reaction mixture is stirred for 2 hours at room temperature, then 10 ml of a saturated aqueous ammonium chloride solution are added and extraction is carried out with ethyl acetate. The organic phase is dried over anhydrous sodium sulphate and then the solvents are evaporated under reduced pressure. The residue obtained is crystallized from diisopropyl ether; M.p.=166° C.

The compounds of Examples 38 to 44 below are prepared in the same way, optionally purified by silica chromatography:

TABLE 8

(I)

[Structure: 5-chloro-3-methyl-1-(2,4-dimethoxybenzyl)indolin-2-one core with $R_0$ at position 3]

| EXAMPLE | $R_0$ | M.p.; ° C.; salt, (solvate) |
|---|---|---|
| 38 | [2-methoxyphenyl-methyl-] | 139, 0.2 H$_2$O |
| 39 | [2,4-dichloro-3-methylphenyl-] | 161, 0.4 H$_2$O |
| 40 | [4-chloro-3-methylphenyl-CH$_2$OCH$_2$OCH$_3$] | 81 |
| 41 | [4-chloro-3-methylphenyl-COOCH$_3$] | 155 |
| 42 | [4-chloro-3-methylphenyl-COOC(CH$_3$)$_3$] | 140 |
| 43 | [4-chloro-3-methylphenyl-NH$_2$] | 165 |
| 44 | [2-methylphenyl-] | 145, 0.2 H$_2$O |

The racemic compound of Example 41 is chromatographed on a chiral column under the conditions of Example 1, elution being carried out with a 90/10 2-methylpentane/2-propanol mixture. The dextrorotatory enantiomer: M.p.=120° C., $[\alpha]_D^{20}$=+112° (c=1, ethyl acetate), and its antipode are obtained.

Example 45

Ethyl Ester of [5-Chloro-3-(2-chlorophenyl)-1-(2,4-dimethoxybenzyl)-2-oxoindolin-3-yl]carboxylic Acid

(I)

$R_0$ = [2-chlorophenyl]; $R_1$ = —COOCH$_2$CH$_3$; $R_2$ = H;

$R_3$ = 4-OCH$_3$; $R_4$ = 2-OCH$_3$; X = 5-Cl; Y = H 0.082 g of potassium tert-butoxide is added to 0.26 g of compound III.1 in 7 ml of tetrahydrofuran cooled to −40° C.

The reaction mixture is stirred for 15 minutes at 0° C. and then 0.086 ml of ethyl chloroformate is added slowly at −65° C. After stirring for 30 minutes at 20° C., the reaction is hydrolysed with 20 ml of a 5% ammonium chloride solution and extraction is carried out with ethyl acetate. The organic phase is dried over sodium sulphate and then the solvents are evaporated under reduced pressure. The expected product is isolated after crystallization from isopropanol;

M.p.=112° C. (0.3H$_2$O).

Example 46

Phenyl Ester of [5-Chloro-3-(2-chlorophenyl)-1-(2, 4-dimethoxybenzyl)-2-oxoindolin-3-yl]carboxylic Acid (I):

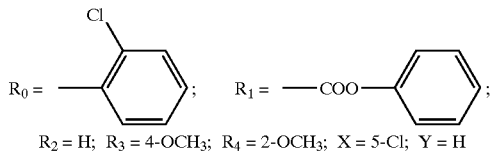

$R_2$ = H; $R_3$ = 4-OCH$_3$; $R_4$ = 2-OCH$_3$; X = 5-Cl; Y = H

The compound of Example 46 is obtained with phenyl chloroformate according to the same procedure as Example 45; M.p.=126° C.

Example 47

5-Chloro-3-(2-chlorophenyl)-1-(2,4-dimethoxybenzyl)-3-hydroxymethylindolin-2-one (I):

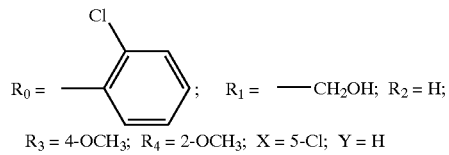

$R_3$ = 4-OCH$_3$; $R_4$ = 2-OCH$_3$; X = 5-Cl; Y = H 0.13 g of potassium tert-butoxide is added at −40° C. to 0.3 g of compound III.1 in 5 ml of tetrahydrofuran. 0.3 g of paraformaldehyde, which is slowly depolymerized by heating, is sparged into the reaction mixture at 0° C. The reaction mixture is stirred for 1 hour at room temperature and then hydrolysed with a 5% aqueous NH$_4$Cl solution. Extraction is carried out with ethyl acetate and the organic phase is dried over sodium sulphate. The solvents are evaporated under reduced pressure and the residue obtained is purified by chromatography on a column of silica gel, elution being carried out with a 90/10 (v/v) cyclohexane/ethyl acetate mixture. The expected product is isolated after crystallization from an n-pentane/ethyl acetate mixture; M.p.=165° C.

Example 48

1-(4-Amino-2-methoxybenzyl)-5-chloro-3-(2-chlorophenyl)-3-methylindolin-2-one (I):

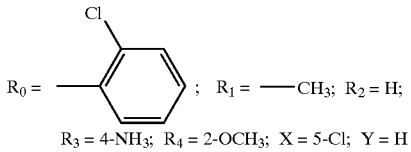

$R_3$ = 4-NH$_3$; $R_4$ = 2-OCH$_3$; X = 5-Cl; Y = H 2.83 g of tin powder and then 5.6 ml of concentrated hydrochloric acid are added to 5.19 g of the compound of Example 5 in 64 ml of ethanol. The reaction mixture is heated at 50° C. for 3 hours. The reaction mixture is filtered at room temperature through celite, the solvent is partially evaporated under reduced pressure, the residue is taken up in ethyl acetate and then the solution is treated with an aqueous sodium bicarbonate solution. The organic phase is dried over anhydrous sodium sulphate and then the solvents are evaporated under reduced pressure. The residue obtained is taken up in diisopropyl ether, filtered off and dried under reduced pressure;

M.p.=232° C.

Example 49

5-Chloro-3-(2-chlorophenyl)-1-(2-methoxy-4-pyrrolidin-1-ylbenzyl)-3-methylindolin-2-one (I):

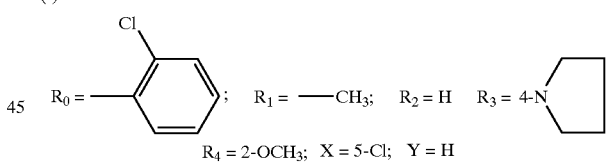

$R_4$ = 2-OCH$_3$; X = 5-Cl; Y = H 0.4 g of sodium bicarbonate powder and 0.14 ml of 1,4-dibromobutane are added to 0.5 g of the compound of Example 48 in 50 ml of hexamethyl-phosphoramide. The reaction mixture is heated at 115° C. for 10 hours. The reaction mixture is hydrolysed at room temperature and extracted with ethyl acetate. The organic phase is washed several times with water and dried over anhydrous sodium sulphate and then the solvents are evaporated under reduced pressure. The residue obtained is purified by chromatography on a column of silica gel, elution being carried out with a 95/5 (v/v) cyclohexane/ethyl acetate mixture. The oil obtained is treated with hydrochloric acid in diethyl ether; M.p.=198° C. (HCl.0.4H$_2$O).

The compounds of Examples 50 to 52 below are prepared in the same way:

TABLE 9

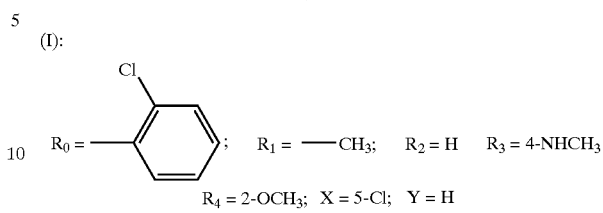

| EXAMPLES | $R_3$ | M.p.; ° C. salt |
|---|---|---|
| 50 | —N(piperidinyl) | 147 |
| 51 | —N(azepanyl) | 197 (1 HCl) |
| 52 | —N(morpholinyl) | 147 |

Example 53

5-Chloro-3-(2-chlorophenyl)-1-[4-dimethylamino-2-methoxybenzyl]-3-methylindolin-2-one (I):

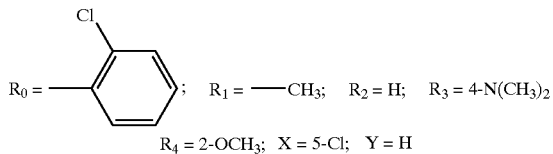

$R_0 =$ 2-chlorophenyl; $R_1 =$ —$CH_3$; $R_2 =$ H; $R_3 =$ 4-N($CH_3$)$_2$ $R_4 =$ 2-$OCH_3$; $X =$ 5-Cl; $Y =$ H 150 ml of methyl iodide are added to 238 mg of the compound of Example 48, in 4 ml of methanol and 1 ml of dimethylformamide, and 100 mg of potassium carbonate and then the reaction mixture is heated at 45° C. for 24 hours. 10 ml of water are added at room temperature and extraction is carried out with ethyl acetate. The organic phase is washed twice with water and dried over anhydrous sodium sulphate, the solvents are evaporated under reduced pressure and the residue is purified by chromatography on a column of silica gel, elution being carried out with a 90/10 (v/v) cyclohexane/ethyl acetate mixture. The residue obtained is crystallized from n-pentane, filtered off and dried under reduced pressure for 4 hours; M.p.=135° C.

Example 54

5-Chloro-3-(2-chlorophenyl)-1-(2-methoxy-4-methylaminobenzyl)-3-methylindolin-2-one (I):

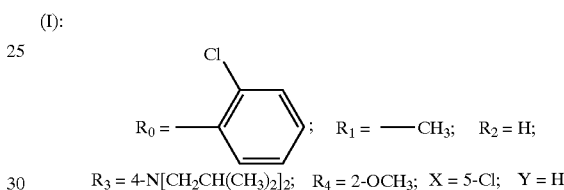

$R_0 =$ 2-chlorophenyl; $R_1 =$ —$CH_3$; $R_2 =$ H; $R_3 =$ 4-NHCH$_3$ $R_4 =$ 2-$OCH_3$; $X =$ 5-Cl; $Y =$ H The compound of Example 54 is prepared according to the procedure described for Example 53;
M.p.=226° C. (H$_2$O).

Example 55

5-Chloro-3-(2-chlorophenyl)-1-(4-diisobutylamino-2-methoxybenzyl)-3-methylindolin-2-one (I):

$R_0 =$ 2-chlorophenyl; $R_1 =$ —$CH_3$; $R_2 =$ H;

$R_3 =$ 4-N[CH$_2$CH(CH$_3$)$_2$]$_2$; $R_4 =$ 2-OCH$_3$; $X =$ 5-Cl; $Y =$ H

Obtained by reductive diamination according to J. Org. Chem., 1996, 61(11), 3849–3862.

347 mg of sodium triacetoxyborohydride are added at 20° C. to 0.25 g of the compound of Example 48 in 6 ml of 1,2-dichloroethane, 167 μl of acetic acid and 106 μl of isobutyraldehyde. After stirring for 1 hour at room temperature, the reaction mixture is hydrolysed with 20 ml of water and extraction is carried out with ethyl acetate. The organic phase is dried over anhydrous sodium sulphate and then the solvents are evaporated under reduced pressure. The residue is chromatographed on a column of silica gel, elution being carried out with a 97/3 (v/v) cyclohexane/ethyl acetate mixture. The oil obtained is taken up in solution of hydrochloric acid in diethyl ether, filtration is carried out and the solvents are evaporated under reduced pressure. The solid obtained is dried at 45° C. under reduced pressure for 5 hours.
M.p.=153° C. (HCl.0.5H$_2$O).

Example 56

5-Chloro-3-(2-chlorophenyl)-1-(4-isopropylamino-2-methoxybenzyl)-3-methylindolin-2-one (I):

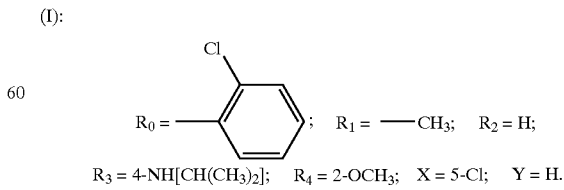

$R_0 =$ 2-chlorophenyl; $R_1 =$ —$CH_3$; $R_2 =$ H;

$R_3 =$ 4-NH[CH(CH$_3$)$_2$]; $R_4 =$ 2-OCH$_3$; $X =$ 5-Cl; $Y =$ H.

Obtained by reductive amination according to J. Org. Chem., 1996, 61(11), 3849–3862.

0.26 ml of acetic acid, 0.14 ml of acetone and then 0.56 g of sodium triacetoxyborohydride are added to 0.40 g of the compound of Example 48 in 10 ml of 1,2-dichloroethane at room temperature. After stirring for 2 hours at room temperature, the reaction mixture is hydrolysed with an aqueous sodium hydrogencarbonate solution and extracted with ethyl acetate. The organic phase is washed with water and dried over anhydrous sodium sulphate and the solvents are evaporated under reduced pressure. The expected product is obtained by filtration of the crystallized evaporation residue taken up in n-pentane;

M.p.=154° C. This compound, in the racemic form, is then separated by chromatography on a chiral column under the same conditions as in Example 1; the dextrorotatory enantiomer: M.p.=137° C.; $[\alpha]_D^{20}=+34.6°$ (c=1, $CH_3OH$), and its antipode are thus isolated.

Example 57

5-Chloro-3-(2-chlorophenyl)-1-[4-(isopropylmethylamino)-2-methoxybenzyl]-3-methylindolin-2-one (I):

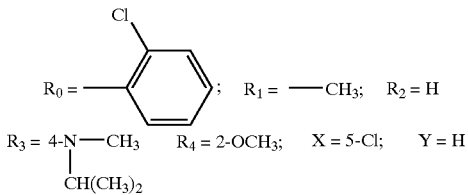

The compound of Example 56 is treated with aqueous formaldehyde and sodium borohydride. The compound obtained is salified with a solution of hydrochloric acid in diethyl ether. The hydrochloride is then isolated after filtration and drying at 45° C. under reduced pressure; M.p.=156° C. ($HCl.1.5H_2O$).

Example 58

{4-[5-Chloro-3-(2-chlorophenyl)-3-methyl-2-oxoindolin-1-ylmethyl]-3-methoxyphenyl}isopropyldimethylammonium Iodide (I):

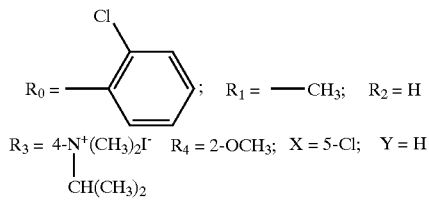

0.56 g of caesium carbonate and then 0.27 ml of methyl iodide are added to 0.4 g of the compound of Example 56 in 10 ml of dimethylformamide. The reaction mixture is heated with stirring at 40° C. for 48 hours. The reaction mixture is treated at room temperature with 40 ml of water and extracted twice with diethyl ether and then 3 times with dichloromethane. The chlorinated solvent organic phases are dried over anhydrous sodium sulphate and evaporated under reduced pressure. The residue thus obtained is taken up in diethyl ether, filtered off and dried at 50° C. under reduced pressure; M.p.=146° C. ($1H_2O$).

Example 59

5-Chloro-3-(2-chlorophenyl)-1-[4-(cyclopropylamino)-2-methoxybenzyl]-3-methylindolin-2-one (I):

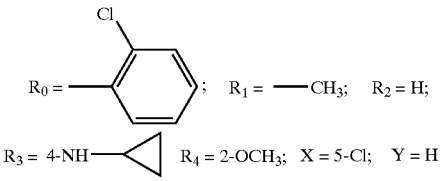

Obtained from the compound of Example 48 according to T.L., 1995, 36(41), 7399–7402.

0.54 ml of acetic acid, 0.4 g of 3 Å molecular sieve and 0.207 ml of (1-ethoxycyclopropyl)oxytrimethylsilane are added to 0.4 g of the compound of Example 48 in solution in 10 ml of methanol. After stirring for 30 minutes at room temperature, 0.265 g of sodium cyanoborohydride is added and then the mixture is heated at reflux for 10 hours. After cooling, hydrolysis is carried out with 20 ml of 2N sodium hydroxide solution, filtration is carried out through celite and the celite is rinsed with ethyl acetate. The organic phase is washed with a 10% aqueous sodium chloride solution and dried over sodium sulphate and the solvents are evaporated under reduced pressure.

The residue is purified by chromatography on a column of silica gel, elution being carried out with a 50/50 (v/v) cyclohexane/dichloromethane mixture and then with pure dichloromethane. The expected product is isolated after crystallization of from n-pentane; M.p.=185° C. ($0.5H_2O$).

Example 60

5-Chloro-3-(2-chlorophenyl)-1-[4-diethylamino-2-methoxybenzyl]-3-methylindolin-2-one (I):

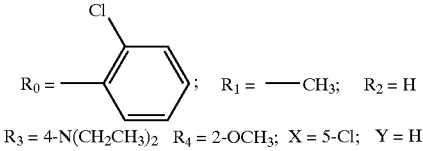

According to Gordon W. Gribble et al., J. Am. Chem. Soc. 1974, 96(25), 7812.

0.45 g of sodium borohydride is added to 0.5 g of the compound of Example 48 in 7 ml of acetic acid. The reaction mixture is heated to 60° C. with stirring for 4 hours, the solvents are partially evaporated, the reaction mixture is hydrolysed with an aqueous sodium bicarbonate solution and extraction is carried out with ethyl acetate. The organic phase is dried over anhydrous sodium sulphate and concentrated under reduced pressure. The oil obtained is treated with a solution of hydrochloric acid in diethyl ether;

M.p.=198° C. (HCl).

Example 61

5-Chloro-3-(2-chlorophenyl)-1-[4-ethylamino-2-methoxybenzyl]-3-methylindolin-2-one (I):

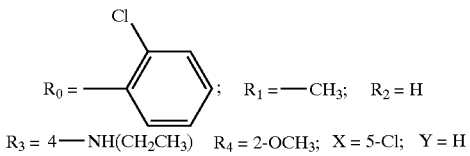

$R_0 =$ (2-chlorophenyl); $R_1 = -CH_3$; $R_2 = H$
$R_3 = 4-NH(CH_2CH_3)$  $R_4 = 2-OCH_3$; $X = 5-Cl$; $Y = H$ The compound of Example 61 is prepared according to the same procedure as for Example 60;
M.p.=167° C.

Example 62

N-{4-[5-Chloro-3-(2-chlorophenyl)-3-methyl-2-oxoindolin-1-yl]-3-methoxyphenyl}acetamide (I):

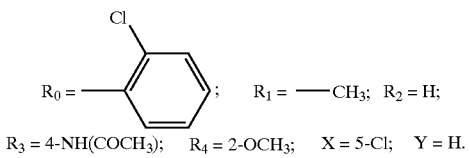

$R_0 =$ ; $R_1 = -CH_3$; $R_2 = H$;
$R_3 = 4-NH(COCH_3)$;  $R_4 = 2-OCH_3$;  $X = 5-Cl$;  $Y = H$.

0.10 ml of acetyl chloride is slowly added at 0° C. to 0.5 g of the compound of Example 48 in 10 ml of dichloromethane and 0.5 ml of triethylamine. The reaction mixture is hydrolysed at room temperature, 20 ml of dichloromethane are added, the organic phase is dried over $Na_2SO_4$ and the solvents are evaporated under reduced pressure. The residue obtained is purified by chromatography on a column of silica gel, elution being carried out with a 50/50 (v/v) cyclo-hexane/ethyl acetate mixture; M.p.=83° C.

Example 63

5-Chloro-3-(2-chlorophenyl)-1-(4-ethoxy-2-methoxybenzyl)-3-methylindolin-2-one (I):

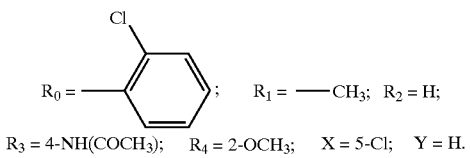

$R_0 =$ ; $R_1 = -CH_3$; $R_2 = H$;
$R_3 = 4-NH(COCH_3)$;  $R_4 = 2-OCH_3$;  $X = 5-Cl$;  $Y = H$.

a) 5-Chloro-3-(2-chlorophenyl)-1-(4-hydroxy-2-methoxybenzyl)-3-methylindolin-2-one 3 ml of trifluoroacetic acid are added at 0° C. to 1.14 g of the compound of Example 3 in 20 ml of dichloromethane and 1 ml of methyl phenyl sulphide. After stirring for 2 hours at room temperature, the reaction mixture is hydrolysed and extraction is carried out with ethyl acetate. The organic phase is washed with an aqueous sodium bicarbonate solution and dried over anhydrous sodium sulphate and then the solvents are evaporated under reduced pressure. The residue obtained is purified by chromatography on a column of silica gel, elution being carried out by an 80/20 (v/v) cyclohexane/ethyl acetate mixture;
M.p.=200° C.

b) 0.23 g of caesium carbonate and then, at 0° C., 0.112 ml of iodoethane are added to 0.2 g of the compound obtained in a) in 5 ml of dimethyl-formamide. After stirring for 1 hour at 28° C., the reaction mixture is hydrolysed and extraction is carried out with ethyl acetate. The organic phase is dried over anhydrous sodium sulphate and the solvents are evaporated under reduced pressure. The oil obtained is taken up in n-pentane and the precipitate obtained is filtered off and dried at 50° C. under reduced pressure for 5 hours; M.p. 124° C.

Example 64

5-Chloro-3-(2-chlorophenyl)-1-(2,4-dimethoxybenzyl)-3-methoxymethylindolin-2-one (I):

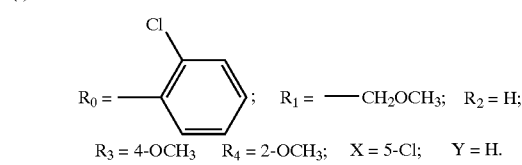

$R_0 =$ ; $R_1 = -CH_2OCH_3$; $R_2 = H$;
$R_3 = 4-OCH_3$   $R_4 = 2-OCH_3$;   $X = 5-Cl$;   $Y = H$.

0.1 ml of methyl trifluoromethanesulphonate and then 0.07 ml of 2,6-di(tert-butyl)pyridine are added at −20° C. to a solution of 70 mg of the compound obtained according to Example 47 in 1 ml of dichloromethane and the reaction mixture is maintained at +5° C. for one week. The solvent is evaporated under reduced pressure, 5 ml of 0.1N hydrochloric acid are added and extraction is carried out with ethyl acetate. The organic phase is dried over anhydrous sodium sulphate and the solvent is evaporated under reduced pressure. The residue obtained is purified by chromatography on a column of silica gel, elution being carried out with a 95/5 (v/v) cyclohexane/ethyl acetate mixture. The resin obtained is taken up in n-pentane.

The solid obtained is filtered off and dried for 5 hours at 50° C.; M.p.=125° C. (0.4H$_2$O).

Example 65

5-Chloro-3-(2-chloro-5-hydroxymethylphenyl)-1-(2,4-dimethoxybenzyl)-3-hydroxyindolin-2-one (I):

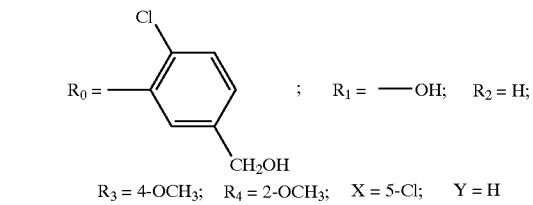

$R_0 =$ ; $R_1 = -OH$; $R_2 = H$;
$R_3 = 4-OCH_3$;  $R_4 = 2-OCH_3$;  $X = 5-Cl$;  $Y = H$

A mixture of 0:307 g of the compound of Example 19, 15 ml of methanol and 1 ml of 10N hydrochloric acid is heated at 50° C. for 2 hours. The solvent is evaporated under reduced pressure and the residue obtained is taken up in dichloromethane and water. The organic phase is washed

Example 66

5-Chloro-3-[2-chloro-5-(dimethylamino)phenyl]-1-(2,4-dimethoxybenzyl)-3-methylindolin-2-one (I):

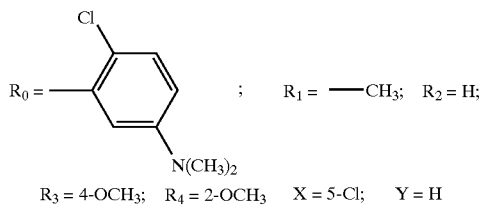

$R_0 =$ ; $R_1 = —CH_3$; $R_2 = H$;
$N(CH_3)_2$
$R_3 = 4\text{-}OCH_3$; $R_4 = 2\text{-}OCH_3$ $X = 5\text{-}Cl$; $Y = H$ Prepared from the compound of Example 43 according to the procedure described for Example 53. The expected product is isolated after crystallization from isopropyl ether; M.p.=149° C. (0.7H$_2$O).

Example 67

4-Chloro-3-[5-chloro-1-(2,4-dimethoxybenzyl)-3-methyl-2-oxoindolin-3-yl]phenylformamide According to T.L., 1982, 23(33), 3315.

(I):

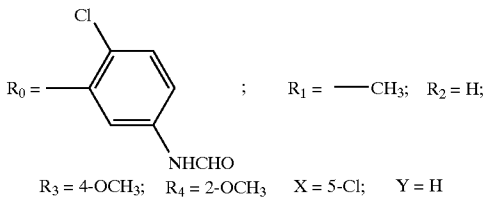

$R_0 =$ ; $R_1 = —CH_3$; $R_2 = H$;
NHCHO
$R_3 = 4\text{-}OCH_3$; $R_4 = 2\text{-}OCH_3$ $X = 5\text{-}Cl$; $Y = H$ 0.216 ml of formic acid is added to 0.44 ml of acetic anhydride cooled to 0° C. and then the reaction mixture is heated at 58° C. for 1 hour 30 minutes. After cooling to 10° C., 0.8 ml of tetrahydrofuran is added, followed by 0.80 g of the compound of Example 43 in solution of 4 ml of tetrahydrofuran. After stirring for 2 hours at 20° C., the solvents are evaporated under reduced pressure. The residue obtained is taken up in n-pentane and the produce is filtered off; M.p.=190° C.

Example 68

5-Chloro-3-[2-chloro-5-(methylamino)phenyl]-1-(2,4-dimethoxybenzyl)-3-methylindolin-2-one (I):

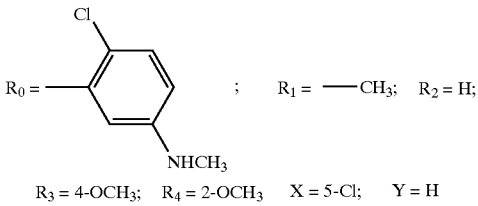

$R_0 =$ ; $R_1 = —CH_3$; $R_2 = H$;
NHCH$_3$
$R_3 = 4\text{-}OCH_3$; $R_4 = 2\text{-}OCH_3$ $X = 5\text{-}Cl$; $Y = H$ Prepared according to T.L. 1982, 23(33), 3315.

0.56 ml of a 2M solution of borane-dimethyl sulphide in tetrahydrofuran is added to a solution, cooled to 0° C., of 0.4 g of the compound of Example 67 in 1 ml of tetrahydrofuran. After 1 hour at 58° C. and then cooling to 0° C., 0.2 ml of 10N hydrochloric acid and 1 ml of methanol are added to the reaction mixture. The mixture is heated at 60° C. for 1 hour and cooled, and the solvents are evaporated under reduced pressure. The solid residue is treated with 1 ml of a saturated potassium carbonate solution and extraction is carried out several times with ethyl acetate. The organic phases are dried over anhydrous sodium sulphate and the solvents are evaporated under reduced pressure. Purification is carried out by chromatography on a column of silica gel, elution being carried out with an 85/15 (v/v) cyclohexane/ethyl acetate mixture. The expected product is isolated in the form of the hydrochloride by treating the residue obtained with diethyl ether comprising hydrogen chloride and then filtration is carried out; M.p.=121° C. (0.5H$_2$O.1HCl).

Example 69

5-Chloro-3-(2-chloro-5-[ethyl(methyl)amino]phenyl}-1-(2,4-dimethoxybenzyl)-3-methylindolin-2-one (I):

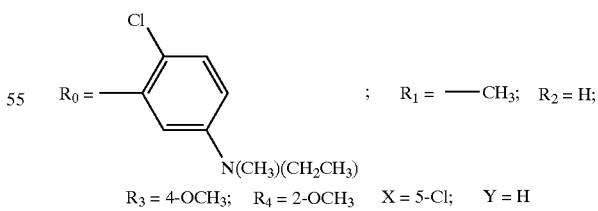

$R_0 =$ ; $R_1 = —CH_3$; $R_2 = H$;
$N(CH_3)(CH_2CH_3)$
$R_3 = 4\text{-}OCH_3$; $R_4 = 2\text{-}OCH_3$ $X = 5\text{-}Cl$; $Y = H$ Obtained from the compound of Example 68 according to the same procedure as for Example 60;

M.p.=145° C.

Example 70

N-{4-Chloro-3-[5-chloro-1-(2,4-dimethoxybenzyl)-3-methyl-2-oxoindolin-3-yl]phenyl}acetamide (I):

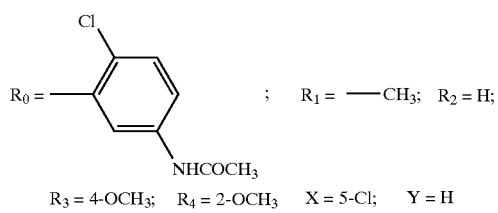

$R_3$ = 4-OCH$_3$;   $R_4$ = 2-OCH$_3$   X = 5-Cl;   Y = H

Obtained according to the same procedure as the compound of Example 62 from the compound of Example 43; M.p.=117° C.

The [lacuna] following Examples 71 to 80 are obtained in the same way:

TABLE 10

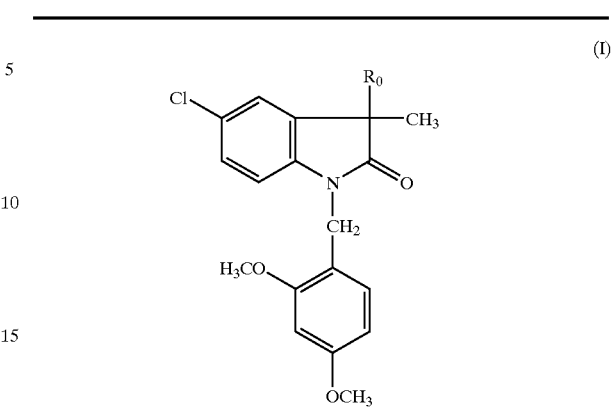

(I)

| EXAMPLES | R$_0$ | M.p.; ° C. |
|---|---|---|
| 71 | Cl—C$_6$H$_3$(CH$_3$)—NHCOCH$_2$CH$_3$ | 238  0.5 H$_2$O |
| 72 | Cl—C$_6$H$_3$(CH$_3$)—NHCOCH(CH$_3$)$_2$ | 258  0.5 H$_2$O |
| 73 | Cl—C$_6$H$_3$(CH$_3$)—NHCOCH$_2$CH(CH$_3$)$_2$ | 203  0.3 H$_2$O |
| 74 | Cl—C$_6$H$_3$(CH$_3$)—NHCOC$_6$H$_5$ | 255  0.5 H$_2$O |
| 75 | Cl—C$_6$H$_3$(CH$_3$)—NHCOCH$_2$C$_6$H$_5$ | 229  0.5 H$_2$O |
| 76 | Cl—C$_6$H$_3$(CH$_3$)—NHCO-(3-pyridyl) | 127  1 H$_2$O |
| 77 | Cl—C$_6$H$_3$(CH$_3$)—NHCOCH$_2$OCH$_3$ | 191 |
| 78 | Cl—C$_6$H$_3$(CH$_3$)—NHCOCH$_2$COOCH$_3$ | 153  0.5 H$_2$O |

TABLE 10-continued (I)

| EXAMPLES | $R_0$ | M.p.; °C. |
|---|---|---|
| 79 | (4-Cl, 3-CH$_3$-phenyl)-NHCO(CH$_2$)$_2$COOCH$_3$ | 203<br>0.5 H$_2$O |
| 80 | (4-Cl, 3-CH$_3$-phenyl)-NH-C(=O)-(3-Cl-phenyl) | 255<br>0.5 H$_2$O |

Example 81

N-{4-Chloro-3-[5-chloro-1-(2,4-dimethoxybenzyl)-3-methyl-2-oxoindolin-3-yl]phenyl}-3-methoxypropanamide (I):

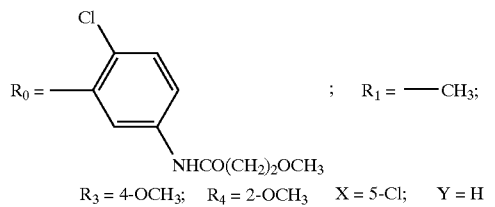

$R_3 = 4\text{-OCH}_3$; $R_4 = 2\text{-OCH}_3$ $X = 5\text{-Cl}$; $Y = H$ 0.068 ml of 3-methoxypropionic acid and 320 mg of benzotriazolyl-N-oxytrisdimethylaminophosphonium hexafluorophosphate are added to 0.3 g of the compound of Example 43 in 10 ml of dimethyl-formamide. After cooling to 0° C., 0.23 ml of triethylamine is added. The reaction mixture is stirred at room temperature for 16 hours. 40 ml of water are added and extraction is carried out with 30 ml of ethyl acetate. The organic phase is treated with 20 ml of an aqueous sodium bicarbonate solution, this phase is separated by settling and is dried over anhydrous sodium sulphate, and the solvents are evaporated under reduced pressure. The residue is purified by chromatography on a column of silica gel, elution being carried out with dichloromethane. The expected product is obtained after crystallization from n-pentane;

M.p.=168° C. (0.3H$_2$O).

The compounds of the following Examples 82 to 86 are obtained in the same way:

TABLE 11

(I)

| EXAMPLES | $R_0$ | M.p.; °C. |
|---|---|---|
| 82 | (4-Cl, 3-CH$_3$-phenyl)-NHCOCH$_2$N(CH$_3$)$_2$ | 145<br>0.3 H$_2$O |
| 83 | (4-Cl, 3-CH$_3$-phenyl)-NHCO(CH$_2$)$_2$N(C$_2$H$_5$)$_2$ | 92 |
| 84 | (4-Cl, 3-CH$_3$-phenyl)-NHCO(CH$_2$)$_2$CON(CH$_3$)$_2$ | 107<br>0.5 H$_2$O |
| 85 | (4-Cl, 3-CH$_3$-phenyl)-NH-C(=O)-(2,4-diCl-phenyl) | 126<br>0.3 H$_2$O |

TABLE 11-continued

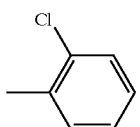
(I)

| EXAMPLES | R₀ | M.p.; °C. |
|---|---|---|
| 86 | 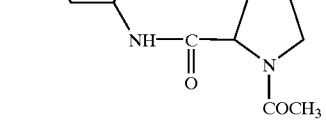 | 143 1 H₂O |

Example 87

N-{4-Chloro-3-[5-chloro-1-(2,4-dimethoxybenzyl)-3-methyl-2-oxoindolin-3-yl]phenyl}-N-methylacetamide (I):

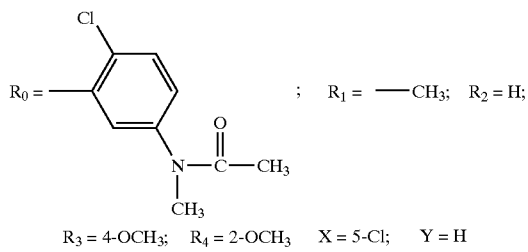 ; R₁ = —CH₃; R₂ = H;

R₃ = 4-OCH₃; R₄ = 2-OCH₃; X = 5-Cl; Y = H

Obtained from the compound of Example 68 according to the same procedure as in Example 62;

M.p.=84° C.

The compounds of the following Examples 88 to 90 are obtained in the same way:

TABLE 12

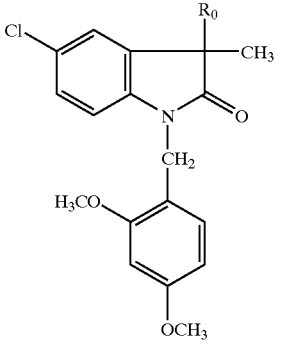
(I)

| EXAMPLES | R₀ | M.p.; °C. |
|---|---|---|
| 88 | 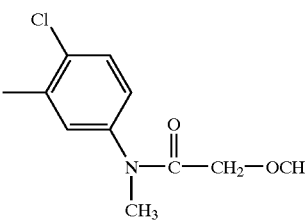 | 129 |
| 89 | 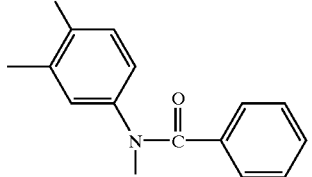 | 72 |
| 90 | 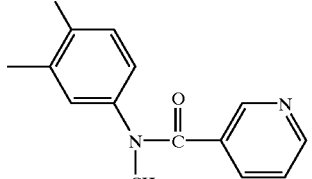 | 72 |

Example 91

N-{4-Chloro-3-[5-chloro-1-(2,4-dimethoxybenzyl)-3-methyl-2-oxoindolin-3-yl]phenyl}-2-(dimethylamino)-N-methylacetamide (I):

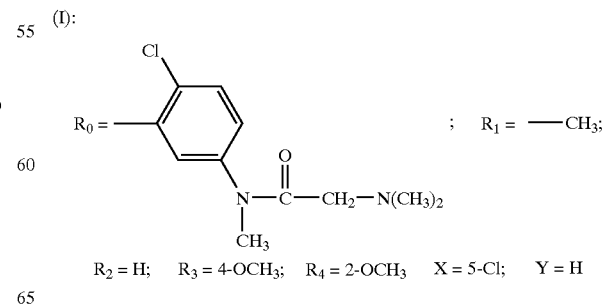 ; R₁ = —CH₃;

R₂ = H; R₃ = 4-OCH₃; R₄ = 2-OCH₃; X = 5-Cl; Y = H

According to the procedure of Synthesis 1980, 547.

0.14 g of N,N-dimethylglycine, 0.40 ml of triethylamine and 0.34 g of N,N-bis[2-oxo-3-oxo-zalidinyl] phosphorodiamide chloride are added at 0° C. to 0.32 g of [lacuna] Example 68 in 5 ml of dichloromethane. The reaction mixture is stirred for 24 hours at room temperature, 20 ml of an aqueous sodium bicarbonate solution are added and extraction is carried out with 30 ml of ethyl acetate. The organic phase is again washed with 20 ml of an aqueous sodium bicarbonate solution and then dried over anhydrous sodium sulphate. The solvents are evaporated under reduced pressure. Purification is carried out by chromatography on a column of silica gel, elution being carried out with a 97/3 (v/v) dichloromethane/methanol mixture. The expected product is isolated by crystallization from n-pentane; M.p.=104° C.

Example 92

1-Acetyl-N-{4-chloro-3-[5-chloro-1-(2,4-dimethoxybenzyl)-3-methyl-2-oxoindolin-3-yl]phenyl}-N-methyl-2-pyrrolidinecarboxamide (I):

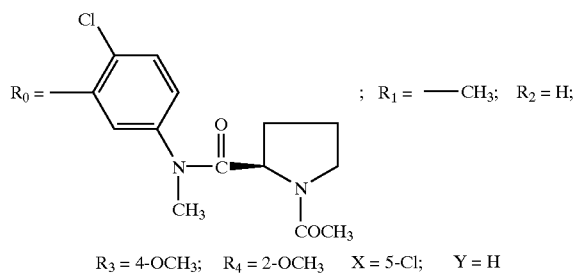

$R_3 = 4\text{-OCH}_3;\quad R_4 = 2\text{-OCH}_3\quad X = 5\text{-Cl};\quad Y = H$ Prepared according to the same procedure as in Example 91; M.p.=74° C. (2H$_2$O).

Example 93

N-{4-Chloro-3-[5-chloro-1-(2,4-dimethoxybenzyl)-3-methyl-2-oxoindolin-3-yl]phenyl}urea (I):

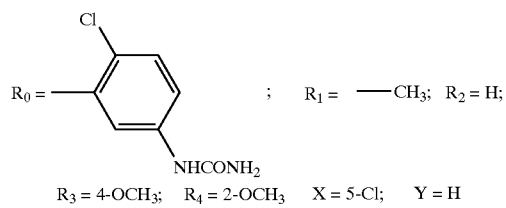

$R_3 = 4\text{-OCH}_3;\quad R_4 = 2\text{-OCH}_3\quad X = 5\text{-Cl};\quad Y = H$ a) Formation of phenyl 4-chloro-3-[5-chloro-1-(2,4-dimethoxybenzyl)-3-methyl-2-oxoindolin-3-yl]phenylcarbamate.

0.30 ml of 30% sodium hydroxide solution is added to 0.4 g of the compound of Example 43 in 20 ml of tetrahydrofuran. After cooling to −5° C., 0.33 ml of phenyl chlorocarbonate is added to the reaction mixture. After stirring for 4 hours at room temperature, 30 ml of water are added and extraction is carried out with 50 ml of ethyl acetate. The organic phase is dried over anhydrous sodium sulphate and the solvents are evaporated under reduced pressure. The oil obtained is used in the following stage.

b) Production of the compound of Example 93.

The compound obtained in a) is taken up in 30 ml of dichloromethane in the presence of 1 ml of liquid ammonia. After stirring for 48 hours at room temperature, the solvent is partially evaporated and the residue obtained is taken up in diethyl ether. The product is filtered off and washed with diethyl ether;

M.p.=254° C. (1.5H$_2$O).

Example 94

N-{4-Chloro-3-[5-chloro-1-(2,4-dimethoxybenzyl)-3-methyl-2-oxoindolin-3-yl]phenyl}-N,N-dimethylurea (I):

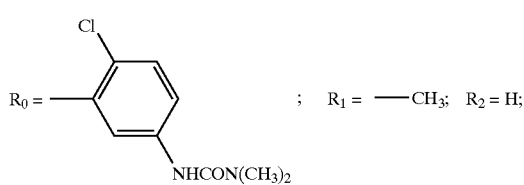

$R_3 = 4\text{-OCH}_3;\quad R_4 = 2\text{-OCH}_3\quad X = 5\text{-Cl};\quad Y = H$ Obtained according to the same procedure as for Example 93; M.p.=182 C (0.4H$_2$O).

Example 95

N-{4-Chloro-3-[5-chloro-1-(2,4-dimethoxybenzyl)-3-methyl-2oxoindolin-3-yl]phenyl}methanesulphonamide (I):

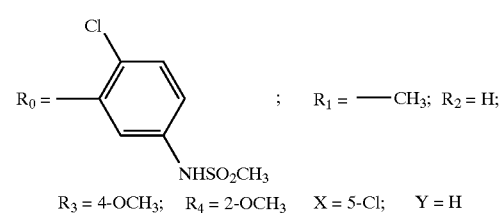

$R_3 = 4\text{-OCH}_3;\quad R_4 = 2\text{-OCH}_3\quad X = 5\text{-Cl};\quad Y = H$ 0.23 ml of triethylamine are added to 0.3 g of the compound of Example 43 in 10 ml of dichloromethane and then, after cooling to −10° C., 56 μl of methanesulphonyl chloride are added. After stirring for 24 hours at room temperature, 10 ml of an aqueous sodium hydrogen carbonate solution and 30 ml of ethyl acetate are added. The organic phase is isolated and dried over anhydrous sodium sulphate, and the solvents are evaporated under reduced pressure. The residue obtained is purified by chromatography on a column of silica gel, elution being carried out with dichloromethane. The expected product is obtained after crystallization from n-pentane; M.p.=210° C. (0.25H$_2$O).

Example 96

N-{4-Chloro-3-[5-chloro-1-(2,4-dimethoxybenzyl)-3-methyl-2-oxoindolin-3-yl]phenyl}-N-methyl-sulphonyl)methanesulphonamide (I):

$R_0 = $ 4-Cl-C$_6$H$_3$-N(SO$_2$CH$_3$)$_2$ ; $R_1 = $ —CH$_3$; $R_2 = $ H;

$R_3 = $ 4-OCH$_3$; $R_4 = $ 2-OCH$_3$; X = 5-Cl; Y = H

Obtained according to the process of Example 95 using two equivalents of methanesulphonyl chloride; M.p.=159° C.

Example 97

N-{4-Chloro-3-[5-chloro-1-(2,4-dimethoxybenzyl)-3-methyl-2-oxoindolin-3-yl]phenyl}-N-methylmethane-sulphonamide (I):

$R_0 = $ 4-Cl-C$_6$H$_3$-N(CH$_3$)SO$_2$CH$_3$ ; $R_1 = $ —CH$_3$; $R_2 = $ H;

$R_3 = $ 4-OCH$_3$; $R_4 = $ 2-OCH$_3$; X = 5-Cl; Y = H

Obtained according to the procedure of Example 95 from [lacuna] Example 68; M.p.=76° C. (0.8 H$_2$O).

Example 98

N-{4-Chloro-3-[5-chloro-1-(2,4-dimethoxybenzyl)-3-methyl-2-oxoindolin-3-yl]phenyl}-N-methylphenyl-sulphonamide (I):

$R_0 = $ 4-Cl-C$_6$H$_3$-N(CH$_3$)SO$_2$Ph ; $R_1 = $ —CH$_3$;

$R_2 = $ H; $R_3 = $ 4-OCH$_3$; $R_4 = $ 2-OCH$_3$; X = 5-Cl; Y = H

Obtained according to the same procedure as for Example 97; M.p.=73° C. (0.8H$_2$O).

Example 99

5-Chloro-3-[2-chloro-5-(4-morpholinyl)phenyl]-1-(2,4-dimethoxybenzyl)-3-methylindolin-2-one (I):

$R_0 = $ 4-Cl-3-(morpholinyl)phenyl ; $R_1 = $ —CH$_3$; $R_2 = $ H;

$R_3 = $ 4-OCH$_3$; $R_4 = $ 2-OCH$_3$; X = 5-Cl; Y = H

Obtained according to the same procedure as for Example 52 from the compound of Example 43; M.p.=168° C.

Example 100

3-Chloro-3-[2-chloro-5-(4-methyl-1-piperazinyl)phenyl]-1-(2,4-dimethoxybenzyl)-3-methylindolin-2-one (I):

$R_0 = $ 4-Cl-3-(4-methylpiperazinyl)phenyl ; $R_1 = $ —CH$_3$; $R_2 = $ H;

$R_3 = $ 4-OCH$_3$; $R_4 = $ 2-OCH$_3$; X = 5-Cl; Y = H

Obtained according to the same procedure as for Example 1 from compound II.9; M.p.=140° C. (2HCl.0.3H$_2$O).

Example 101

4-Chloro-3-[5-chloro-1-(2,4-dimethoxybenzyl)-3-methyl-2-oxoindolin-3-yl]benzoic Acid (I):

$R_0 = $ 4-Cl-C$_6$H$_3$-COOH ; $R_1 = $ —CH$_3$; $R_2 = $ H;

$R_3 = $ 4-OCH$_3$; $R_4 = $ 2-OCH$_3$; X = 5-Cl; Y = H 11 ml of a 2N aqueous sodium hydroxide solution are added to 3.46 g of the racemic compound of Example 41 in 300 ml of a solution comprising methanol/dioxane (v/v) and the reaction mixture is left stirring for 5 hours at 65° C. After cooling to room temperature, the solvents are partially evaporated under reduced pressure and extraction is carried out with ethyl acetate. The aqueous phase is acidified at 10° C. with a 1N hydrochloric acid solution and the acid is extracted with dichloromethane. The latter organic phase is dried over anhydrous sodium sulphate and the solvents are evaporated under reduced pressure. The expected product is obtained by crystallization of the oil from isopropyl ether; M.p.=186° C.

The dextrorotatory enantiomer: $[\alpha]_D^{20}$=+101.8 (c=1, $CH_3OH$), M.p.=114° C., and its antipode are isolated by chiral chromatography under the conditions of Example 1, elution being carried out with a 90/10 2-methylpentane/2-propanol mixture and 0.1% of trifluoroacetic acid.

Example 102

4-Chloro-3-[5-chloro-1-(2,4-dimethoxybenzyl)-3-methyl-2-oxoindolin-3-yl]-N,N-diethylbenzamide (I):

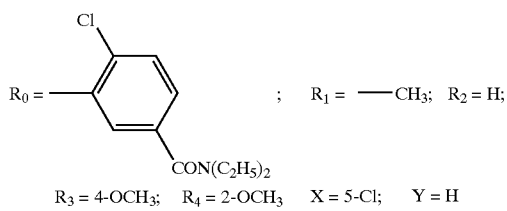

$R_3$ = 4-$OCH_3$;   $R_4$ = 2-$OCH_3$    X = 5-Cl;   Y = H 0.46 g of benzotriazolyl-N-oxytrisdimethyl-aminophosphonium hexafluorophosphate, 0.20 ml of diethylamine and 0.28 ml of triethylamine are added at 0° C. to 0.48 g of the compound of Example 101 in 10 ml of dimethylformamide. After stirring for 15 hours at 20° C., the reaction mixture is hydrolysed with 70 ml of 0.1N hydrochloric acid and extraction is carried out with ethyl acetate. The organic phase is treated with 70 ml of an aqueous sodium hydrogen carbonate solution and dried over anhydrous sodium sulphate. The solvents are evaporated under reduced pressure. The expected product is obtained by crystallization from n-pentane;

M.p.=88° C.

The compound of Example 102, in the racemic form, is purified by chromatography on a ChiralPack® AD column from Daicel, elution being carried out with a 90/10 (v/v) 2-methylpentane/2-propanol mixture. The dextrorotatory enantiomer: M.p.,=86° C.; $[\alpha]_D^{20}$=+100.30 (c=1, $CH_3CO_2C_2H_5$), and its antipode are thus isolated.

The amides of Table 13 are obtained in the same way as for the racemic mixture.

TABLE 13

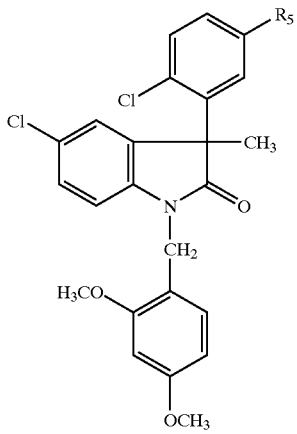

(I)

| EXAMPLES | $R^5$ | M.p.; ° C. |
|---|---|---|
| 103 | —CO—N(morpholine) | 180<br>3 $H_2O$ |
| 104 | —$CONHCH_2COOCH_3$ | 98<br>5 $H_2O$ |
| 105 | —$CONH(CH_2)_3OCH_3$ | 125<br>5 $H_2O$ |
| 106 | —CONH—phenyl | 99<br>4 $H_2O$ |
| 107 | —$CONH(CH_2)_2N(CH_3)_2$ | 111<br>1.5 $H_2O$ |
| 108 | —$CONHCH_2C(CH_3)_3$ | 199<br>2 $H_2O$ |
| 109 | —$CON(CH_3)_2$ | 184<br>1 $H_2O$ |
| 110 | —$CONHCH_3$ | 181<br>3 $H_2O$ |
| 111 | —$CONH_2$ | 133<br>1 $H_2O$ |
| 112 | —CO—N(piperidine) | 154<br>0.5 $H_2O$ |
| 113 | —CO—N(pyrrolidine) | 100<br>0.8 $H_2O$ |
| 114 | —$CONHCH_2CH_3$ | 248<br>0.5 $H_2O$ |
| 115 | —$CONH(CH_2)_2$—N(morpholine) | 128<br>0.5 $H_2O$ |
| 116 | —CO—N(proline methyl ester) | 96<br>0.2 $H_2O$ |

TABLE 13-continued
(I)
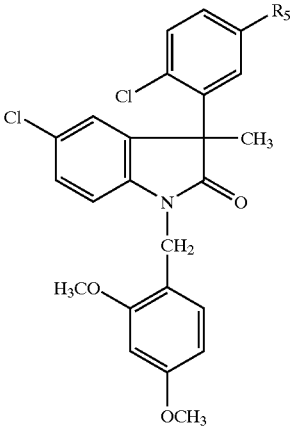
| EXAMPLES | R⁵ | M.p.; ° C. |
|---|---|---|
| 117 | 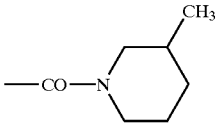 | 72 0.5 H₂O |
| 118 | 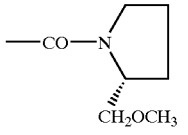 | 98 |
| 119 | 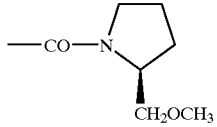 | 98 |
| 120 | 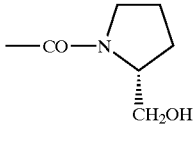 | 87 |
| 121 | 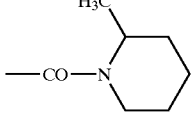 | 122 |
| 122 | 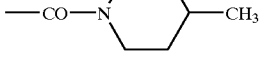 | 124 0.3 H₂O |
| 123 | 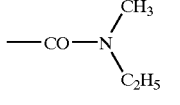 | 115 |
| 124 | 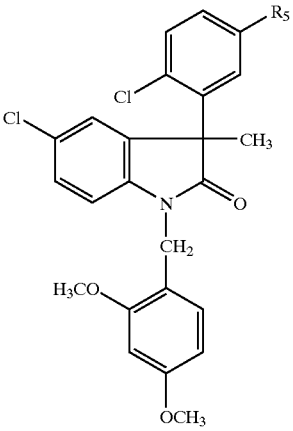 | 166 |
TABLE 13-continued
(I)
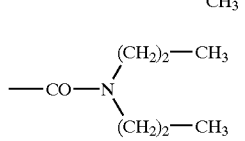
| EXAMPLES | R⁵ | M.p.; ° C. |
|---|---|---|
| 125 | 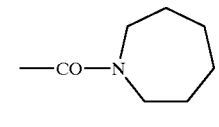 | 102 1 H₂O |
| 126 | 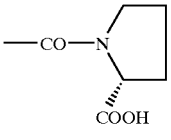 | wax |
| 127 | 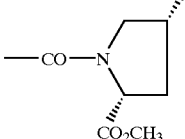 | 123 |
| 128 | 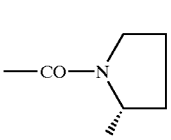 | 175 0.4 H₂O |
| 129 | 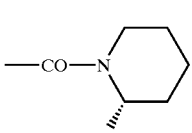 | 110 |
| 130 | | 138 0.2 H₂O |
| 131 | | 116 |

TABLE 13-continued (I)

| EXAMPLES | R⁵ | M.p.; °C. |
|---|---|---|
| 132 | —CO—N⌬—CO₂C₂H₅ | 114 |
| 133 | —CO—N⌬-CO₂C₂H₅ | 118 |
| 134 | —CO—N⌬—OH | 142 0.3 H₂O |
| 135 | —CO—N⌬—CH₂—Ph | 114 0.6 H₂O |
| 136 | —CO—N⌬—N(CH₃)₂ | 130 0.5 H₂CO₃ |
| 137 | —CO—N⌬N—CH₃ | 121 0.4 H₂O |
| 138 | —CO—N⌬N—(2-pyridyl) | 127 0.5 H₂O |
| 139 | —CO—N⌬⋯CO₂C(CH₃)₃ | 110 |

The racemic compound of Example 119 is chromatographed on a chiral column under the conditions of Example 102. The dextrorotatory enantiomer and its antipode are obtained; M.p.=86° C.; $[\alpha]_D^{20}=+129°$ (c=1, ethyl acetate).
idem from the compound of Example 134. The dextrorotatory enantiomer and its antipode are obtained; M.p.=174° C. (H₂O); $[\alpha]_D^{20}=+107°$ (c=1, ethyl acetate).

idem from the compound of Example 131. The dextrorotatory enantiomer and its antipode are obtained; M.p.=91°C.; $[\alpha]_D^{20}=+129°$ (c=1, ethyl acetate).

idem from [lacuna] Example 112. The dextrorotatory enantiomer and its antipode are obtained; M.p.=273° C.; $[\alpha]_D^{20}=+88.3°$ (c=1, ethyl acetate).

Example 140

5-Chloro-3-[2-chloro-5-(hydroxymethyl)phenyl]-1-(2,4-dimethoxybenzyl)-3-methylindolin-2-one (I):

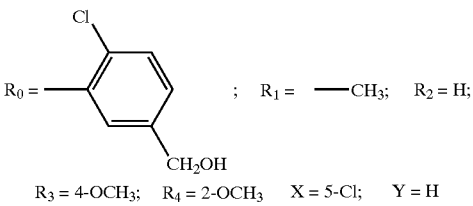

$R_3 = 4\text{-OCH}_3$; $R_4 = 2\text{-OCH}_3$  X = 5-Cl;  Y = H 16.5 ml of a diisobutylalumitnium hydride (DIBAL) solution are added to 3.3 g of the racemic compound of Example 41 in 130 ml of dichloromethane at –68° C. The reaction mixture is treated at –30° C. with 10 ml of methanol and then with an aqueous ammonium chloride solution, and extracted with dichloromethane. Filtration is carried out through celite, the organic phase is washed with water and dried over anhydrous sodium sulphate, and the solvents are evaporated under reduced pressure. The expected product is obtained after crystallization from a cyclohexane/heptane mixture; M.p.=97° C.

This product can also be obtained by deprotection of the compound of Example; 40 in an acidic medium under the conditions of Example 65.

Example 141

5-Chloro-3-[2-chloro-5-(methoxymethyl)phenyl]-1-(2,4-dimethoxybenzyl)-3-methylindolin-2-one (I):

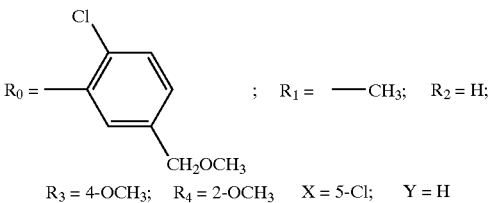

$R_3 = 4\text{-OCH}_3$; $R_4 = 2\text{-OCH}_3$  X = 5-Cl;  Y = H 0.08 ml of methyl iodide and then, at 0° C., 0.02 g of sodium hydride as a 60% suspension in oil are added to 0.2 g of the compound of Example 140 in 2 ml of tetrahydrofuran. After stirring for 16 hours at room temperature, the reaction mixture is hydrolysed with a 5% aqueous ammonium chloride solution and extraction is carried out with ethyl acetate. The organic phase is washed with water and dried over anhydrous sodium sulphate. The solvents are evaporated under reduced pressure. The product is obtained after crystallization from n-pentane; M.p.=122° C.

The compounds of the following Examples 142 to 144 are obtained in the same way:

TABLE 14

(I)

[Structure: 5-chloro-3-methyl-3-$R_0$-1-(2,4-dimethoxybenzyl)indolin-2-one core]

| EXAMPLES | $R_0$ | M.p.; °C. |
|---|---|---|
| 142 | 4-Cl, 3-methyl-phenyl-CH$_2$O(CH$_2$)$_2$OCH$_3$ | 114 |
| 143 | 4-Cl, 3-methyl-phenyl-CH$_2$O(CH$_2$)$_2$OCPh$_3$ | 71 |
| 144 | 4-Cl, 3-methyl-phenyl-CH$_2$OC$_2$H$_5$ | 119 |

Example 145

5-Chloro-3-{2-chloro-5-[(dimethylamino)methyl]phenyl}-1-(2,4-dimethoxybenzyl)-3-methylindolin-2-one (I):

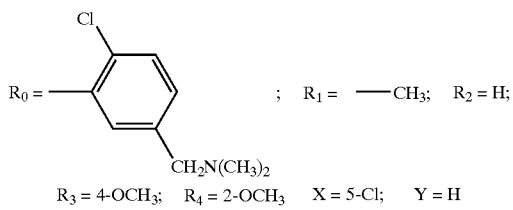

$R_0 =$ 4-Cl-3-(CH$_2$N(CH$_3$)$_2$)-phenyl; $R_1 =$ —CH$_3$; $R_2 =$ H;
$R_3 =$ 4-OCH$_3$; $R_4 =$ 2-OCH$_3$; X = 5-Cl; Y = H a) Preparation of 4-chloro-3-[5-chloro-1-(2,4-dimethoxybenzyl)-3-methyl-2-oxoindolin-3-yl]benzaldehyde. 1 g of the compound of Example 140 is added to 0.69 g of pyridinium chlorochromate in 10 ml of dichloromethane. After stirring for 1 hour at 10° C., the mixture is filtered through celite, the solvents are evaporated under reduced pressure and the residue is purified by chromatography on a column of silica gel, elution being carried out with a 90/10 (v/v) cyclohexane/ethyl acetate mixture. The expected product crystallized from pentane; M.p.=134° C.

b) The compound of Example 145 is obtained by reductive amination of the compound obtained in a) according to the procedure of Example 33; M.p.=125° C. (0.6H$_2$O).

The compounds of the following Examples 146 to 149 are obtained in the same way:

TABLE 15

(I)

[Structure: 5-chloro-3-(2-chloro-5-$R_5$-phenyl)-3-methyl-1-(2,4-dimethoxybenzyl)indolin-2-one]

| EXAMPLES | $R_5$ | M.p.; °C. salt |
|---|---|---|
| 146 | —CH$_2$NHCH$_3$ | 76 H$_2$CO$_3$ |
| 147 | —CH$_2$—N(pyrrolidine-2-carboxylic acid methyl ester, S) | 102 |
| 148 | —CH$_2$—N(morpholine) | 145 |
| 149 | —CH$_2$—N(pyrrolidine) | 106 0.5 H$_2$O |

The racemic compound of Example 148 is chromatographed on a chiral column under conditions analogous to those of Example 102. The dextrorotatory enantiomer, salified with hydrochloric acid in ethyl ether, and its antipode are obtained; M.p.=139° C.

Example 150

N-{4-Chloro-3-[5-chloro-1-(2,4-dimethoxybenzyl)-
3-methyl-2-oxoindolin-3-yl]benzyl}-N-
methylacetamide (I):

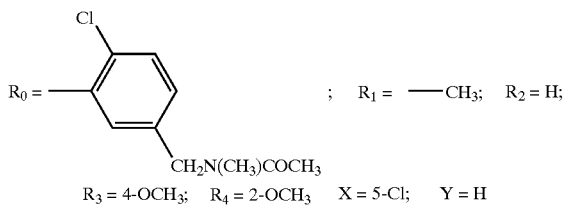

$R_3$ = 4-OCH$_3$;  $R_4$ = 2-OCH$_3$  X = 5-Cl;  Y = H

Obtained according to the same procedure as that of the compound of Example 62 from [lacuna] Example 146; M.p.=81° C. (0.6H$_2$O).

Example 151

5-Chloro-3-{2-chloro-5-[(2-hydroxyethoxy)methyl]-
phenyl}-1-(2,4-dimethoxybenzyl)-3-methylindolin-
2-one (I):

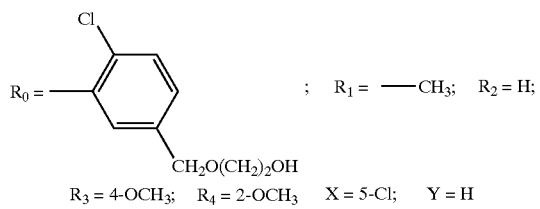

$R_3$ = 4-OCH$_3$;  $R_4$ = 2-OCH$_3$  X = 5-Cl;  Y = H a) Preparation of 5-chloro-3-[2-chloro-5-(1,3-dioxolan-2-yl) phenyl]-1(2,4-dimethoxybenzyl)-3-methylindolin-2-one.

1 ml of ethylene glycol and 16 mg of p-toluenesulphonic acid are added to 2.044 g of the compound prepared in a) of Example 145 in solution in 22 ml of toluene. The reaction mixture is heated to reflux for 16 hours in a reactor equipped with a Dean and Stark apparatus in order to remove the water originating from the reaction. After cooling to room temperature, 30 ml of water are added and extraction is carried out with ethyl acetate. The organic phase is dried over anhydrous sodium sulphate and the solvents are evaporated under reduced pressure to produce the expected product, used directly in the following stage.

b) A 0.29M solution of zinc borohydride in diethyl ether (prepared according to the method described in Chem. Pharm. Bull., 1984, 32(4), 1411–1415) and then 1.2 ml of trimethylsilyl chloride are added to 2.20 g of the compound prepared in a), in solution in 14 ml of dichloromethane, at 6° C. After stirring for 2 hours 30 minutes at room temperature, the reaction mixture is hydrolysed with 30 ml of 1N hydrochloric acid and extraction is carried out with ethyl acetate. The organic phase is washed with water and dried over anhydrous sodium sulphate, and the solvents are evaporated under reduced pressure. The residue obtained is purified by chromatography on a column of silica gel, elution being carried out with a 99/1 (v/v) dichloromethane/methanol mixture. The final product is obtained after crystallization from n-pentane;
M.p.=53° C.

This product can also be obtained by deprotection in acidic medium of the compound of Example 143 according to T.L., 1977, 3473, or any other method described in Protective Groups in O.S. by T. W. Green et al. from Wiley-Interscience (3rd Edition, 1999).

Example 152

5-Chloro-3-(2-chloro-5-{[2-(4-morpholinyl)ethoxy]-
methyl}phenyl)-1-(2,4-dimethoxybenzyl)-3-
methylindolin-2-one (I):

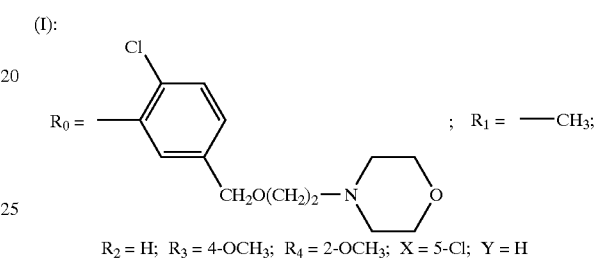

$R_2$ = H;  $R_3$ = 4-OCH$_3$;  $R_4$ = 2-OCH$_3$;  X = 5-Cl;  Y = H a) Preparation of the 5-chloro-3-(2-chloro-5-({2-[(4-methylphenyl)sulphonyl]ethoxy}methyl)phenyl]-1-(2,4-dimethoxybenzyl)-3-methylindolin-2-one derivative.

0.39 ml of triethylamine and then 0.27 g of p-toluenesulphonyl chloride are added to 0.48 g of the compound of Example 151 in 1.5 ml of tetrahydrofuran at 0° C. After stirring for 16 hours at room temperature, the reaction mixture is hydrolysed with 10 ml of water and extraction is carried out with ethyl acetate. The organic phase is washed with with an aqueous sodium hydrogen carbonate solution and then with water. The organic phase is dried over anhydrous sodium sulphate and the solvents are evaporated under reduced pressure to produce the expected product in the form of a paste, which product is used in the following stage.

b) 0.12 g of sodium carbonate and then 0.20 ml of morpholine are added to 0.75 g of the compound obtained in a) in solution in 2 ml of acetonitrile. After 2 hours at 75° C., the reaction mixture is cooled to room temperature, hydrolysis is carried out with 20 ml of water and extraction is carried out with ethyl acetate. The organic phase is washed a further time with water and dried over anhydrous sodium sulphate, the solvents are evaporated under reduced pressure. The residue is purified by chromatography on a column of silica gel, elution being carried out with a 20/80 (v/v) cyclohexane/ethyl acetate mixture. The expected product is obtained after hydrochlorination with a solution of hydrochloric acid in diethyl ether, evaporation and crystallization of the residue from n-pentane;
M.p.=81° C. (0.7H$_2$O.1HCl).

The enantiomers of the compound of Example 152 are obtained in the same way as for Example 102, which enantiomers are salified with fumaric acid in acetone. The fumarates are isolated after evaporation of the acetone and crystallization in dethyl ether: the dextrorotatory enantiomer: M.p.=+112° C.; $[\alpha]_D^{20}$=+76.7 (c=1, $CH_3OH$) and its antipode.

The racemic compounds of the following Examples 153 to 157 are obtained in the same way:

TABLE 16

(I)

[Structure: 5-chloro-3-(2-chloro-5-$R_5$-phenyl)-3-methyl-1-(2-methoxy-4-methoxybenzyl)-indolin-2-one]

| EXAMPLES | $R_5$ | M.p.; ° C. salt |
|---|---|---|
| 153 | —$CH_2O(CH_2)_2$—N(piperazine)N—$CH_3$ | 98<br>4 $H_2O$; 1 HCl |
| 154 | —$CH_2O(CH_2)_2$—N(piperidine) | 61<br>1 $H_2O$; 1 HCl |
| 155 | —$CH_2O(CH_2)_2$—N(pyrrolidine) | 83<br>0.5 $H_2O$; 1 HCl |
| 156 | —$CH_2O(CH_2)_2NH$—$CH_2$—(tetrahydrofuran) | 95<br>1 $H_2O$; 1 HCl |
| 157 | —$CH_2O(CH_2)_2N(CH_3)_2$ | 111<br>1 HCl; 1.5 $H_2O$ |

The compounds of Examples 158 to 162 below are prepared according to the procedure described for Example 18:

TABLE 17

(I)

[Structure: 5-chloro-3-$R_0$-3-hydroxy-1-(2-methoxy-4-methoxybenzyl)-indolin-2-one]

| EXAMPLES | $R_0$ | M.p.; ° C. salt |
|---|---|---|
| 158 | 4-chloro-3-methyl-phenyl with $CF_3$ | 154 |
| 159 | 2,4-dimethoxy-phenyl with methyl ($OCH_3$, $H_3CO$) | 187 |
| 160 | 2-methoxyphenyl with methyl | 153 |
| 161 | 2,4-dimethoxy-phenyl with methyl (different arrangement) | 184 |
| 162 | 2,6-dimethyl-phenyl with methyl | 206 |
| 163 | 2-bromo-phenyl with methyl | 172 |

Example 164

5-Chloro-3-(2-chlorophenyl)-1-(4-hydroxy-2-methoxybenzyl)-3-methylindolin-2-one (I):

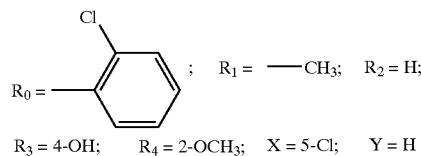

$R_0 = $ ; $R_1 = $ —$CH_3$; $R_2 = H$;

$R_3 = $ 4-OH; $R_4 = $ 2-OCH$_3$; $X = $ 5-Cl; $Y = H$

This compound is already described in a) of Example 63. M.p.=200° C.

Example 165

4-Chloro-3-[5-chloro-1-(2,4-dimethoxybenzyl)-3-hydroxy-2-oxoindolin-3-yl]-N,N-diethylbenzamide (I):

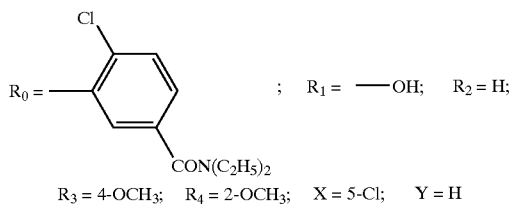

$R_0 = $ ; $R_1 = $ —OH; $R_2 = H$;

$R_3 = $ 4-OCH$_3$; $R_4 = $ 2-OCH$_3$; $X = $ 5-Cl; $Y = H$ a) 4-Chloro-3-[5-chloro-1-(2,4-dimethoxybenzyl)-3-hydroxy-2-oxoindolin-3-yl]benzoic acid From the compound of Example 20 and under the conditions described in Example 101, a solid is isolated which is used in the following stage; M.p.=200° C.

b) By treating the preceding acid under the conditions of Example 102, the expected compound is obtained; M.p.=244° C.

Example 166

1-[4-Chloro-3-[5-chloro-1-(2,4-dimethoxybenzyl)-3-methyl-2-oxoindolin-3-yl]benzoyl]-4-methoxypiperidine

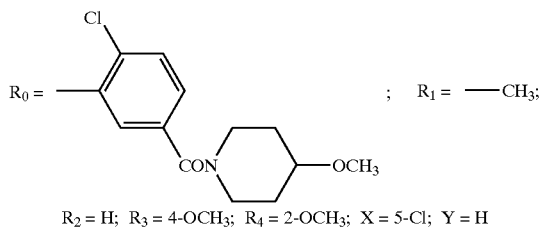

$R_0 = $ ; $R_1 = $ —CH$_3$;

$R_2 = H$; $R_3 = $ 4-OCH$_3$; $R_4 = $ 2-OCH$_3$; $X = $ 5-Cl; $Y = H$ a) 4-Methoxypiperidine:

21.8 ml of methyl trifluoromethanesulphonate are slowly added, at approximately −20° C., to 11 g of 1-tert-butoxycarbonyl-4-hydroxypiperidine, prepared according to J. Med. Chem., 1998, 41, 25, 4983–4994, diluted in 400 ml of dichloromethane and 22.2 ml of 2,6-di(tert-butyl) pyridine. After 16 hours at 20° C., hydrolysis is carried out with 0.5N hydrochloric acid and extraction is carried out with dichloromethane. The organic phase is isolated [lacuna] over sodium sulphate, the solvent is evaporated under reduced pressure and the residue is purified on a column of silica, elution being carried out with a 60/40 dichloromethane/cyclohexane mixture. The oil obtained is used in the following deprotection stage in the presence of 50 ml of a 2M solution of hydrogen chloride in ethyl acetate. After two hours at 20° C., evaporation is carried out under reduced pressure, the residue is triturated with ethyl ether, and the white solid is filtered off and dried under reduced pressure at approximately 50° C. for three hours. The hydrochloride of the expected compound is obtained; M.p.=135° C.

b) By treating the dextrorotatory enantiomer of the compound of Example 101 with the amine described in a) under conditions analogous to those of Example 102, the expected product, crystallized from isopropyl ether, is isolated; M.p.=92° C. (1H$_2$O); $[\alpha]_D^{20}$=+93.3° (c=1, ethyl acetate).

Example 167

1-[4-Chloro-3-[5-chloro-1-(2,4-dimethoxybenzyl)-3-methyl-2-oxoindolin-3-yl]benzoyl]-4-ethoxypiperidine

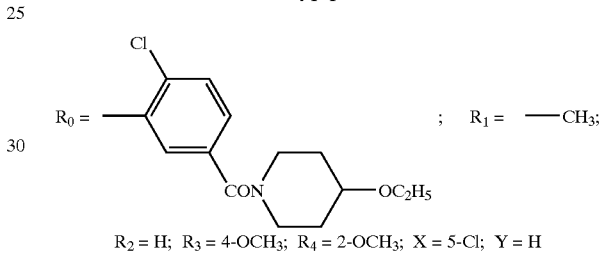

$R_0 = $ ; $R_1 = $ —CH$_3$;

$R_2 = H$; $R_3 = $ 4-OCH$_3$; $R_4 = $ 2-OCH$_3$; $X = $ 5-Cl; $Y = H$ a) 4-Ethoxypiperidine:

Under the conditions of Example 166 a), using ethyl trifluoromethanesulphonate, the hydrochloride of the expected amine is isolated; M.p.=148° C.

b) Example 167 is obtained as for Example 166 b) by using the above amine; M.p.=108° C. (1H$_2$O); $[\alpha]_D^{20}$=+100.10 (c=1, ethyl acetate).

Example 168

1-[4-Chloro-3-[5-chloro-1-(2,4-dimethoxybenzyl)-3-methyl-2-oxoindolin-3-yl]benzoyl]-(R)-2-pyrrolidinocarbonylpiperidine

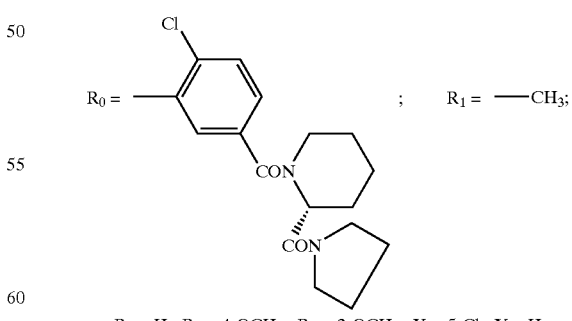

$R_0 = $ ; $R_1 = $ —CH$_3$;

$R_2 = H$; $R_3 = $ 4-OCH$_3$; $R_4 = $ 2-OCH$_3$; $X = $ 5-Cl; $Y = H$ a) (R)-2-(Pyrrolidinocarbonyl)-1-(tert-butoxycarbonyl) piperidine.

From 1-tert-butoxycarbonyl-(R)-2-piperidinecarboxylic acid and pyrrolidine, under conditions analogous to those of Example 102, the expected product is obtained after purification on a column of silica, elution being carried out with a 98/2 dichloromethane/methanol mixture; M.p.=105° C.

b) (R)-2-(Pyrrolidinocarbonyl)piperidine hydrochloride.

Deprotection of the preceding compound under the conditions described in Example 166, a);
M.p.=258° C.

c) Example 168 is obtained with the preceding amine and as for Example 166 b); the expected product, crystallized from isopropyl ether, is obtained;
M.p.=114° C. (0.5H$_2$O).

Example 169

1-[4-Chloro-3-[5-chloro-1-(2,4-dimethoxybenzyl)-3-methyl-2-oxoindolin-3-yl]benzoyl]-(R)-2-N,N-dimethylaminocarbonylpiperidine

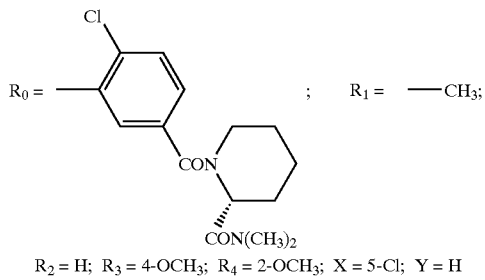

R$_2$ = H; R$_3$ = 4-OCH$_3$; R$_4$ = 2-OCH$_3$; X = 5-Cl; Y = H a) N,N-Dimethyl-1-tert-butoxycarbonyl-(R)-2-piperidinecarboxamide:
Obtained as for Example 168 a); M.p.=76° C.

b) N,N-Dimethyl-(R)-2-piperidinecarboxamide hydrochloride:
Obtained as for Example 168 b);
M.p.=194.4° C.

c) Example 169 is obtained with the preceding amine and as for Example 166 b); the expected product, which crystallizes from isopropyl ether, is obtained;
M.p.=123° C. (1H$_2$O).

Example 170

1-[4-Chloro-3-[5-chloro-1-(2,4-dimethoxybenzyl)-3-methyl-2-oxoindolin-3-yl]benzoyl]-(R)-2-(N-methyl-N-2,2,2-trifluoroethylaminocarbonyl) piperidine

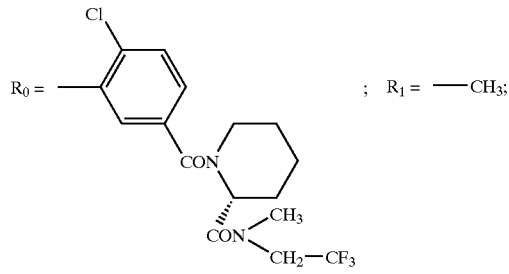

R$_2$ = H; R$_3$ = 4-OCH$_3$; R$_4$ = 2-OCH$_3$; X = 5-Cl; Y = H a) N-Methyl-N-2,2,2-trifluoroethyl-1-tert-butoxycarbonyl-(R)-2-piperidinecarboxamide:
Obtained as for Example 169 a) with the hydrochloride of N-methyl-2,2,2-trifluoroethylamine (M.p.=185° C.) prepared according to J.O.C., 1959, 24, 1256; M.p.=93° C.

b) Example 170 is obtained by deprotecting the amine as for Example 169 b) and the hygroscopic hydrochloride obtained is used with the dextrorotatory enantiomer of the compound of Example 101 under conditions analogous to those of Example 102. The expected product, crystallized from pentane, is isolated; M.p.=99° C.; $[\alpha]_D^{20}$=+103.6° (c=1, ethyl acetate).

Example 171

4-Chloro-3-[5-chloro-1-(2,4-dimethoxybenzyl)-3-methyl-2-oxoindolin-3-yl]-N-methyl-N-(2,2,2-trifluoroethyl)benzamide

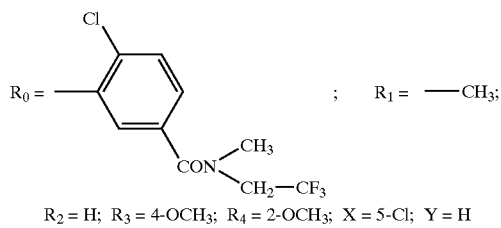

R$_2$ = H; R$_3$ = 4-OCH$_3$; R$_4$ = 2-OCH$_3$; X = 5-Cl; Y = H

Obtained according to Example 166 b) with the hydrochloride of N-methyl-2,2,2-trifluoroethylamine mentioned in a) of Example 170; M.p.=89° C.; $[\alpha]_D^{20}$=+83.4° (c=1, ethyl acetate).

Example 172

1-[4-Chloro-3-[5-chloro-1-(2,4-dimethoxybenzyl)-3-methyl-2-oxoindolin-3-yl]benzoyl]-4-difluoromethylidenepiperidine

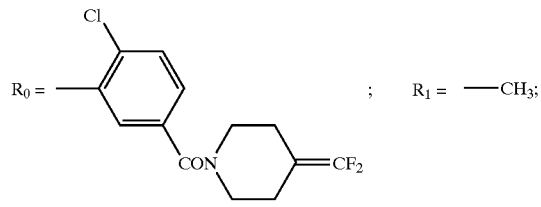

R$_2$ = H; R$_3$ = 4-OCH$_3$; R$_4$ = 2-OCH$_3$; X = 5-Cl; Y = H a) 4-(Difluoromethylidene)piperidine hydrochloride:
Obtained by demethylation of the corresponding N-methyl compound, described in Tetrahedron, 1980, 36, 3241, by the action of α-chloroethyl chloroformate according to J.O.C. 1984, 49, 2081–2082; M.p.=211.5° C.

b) Example 172 is prepared according to Example 166 b) with the amine prepared in a). The expected product is isolated by crystallization from pentane;
M.p.=119° C.

Example 173

1-[4-Chloro-3-[5-chloro-1-(2,4-dimethoxybenzyl)-3-methyl-2-oxoindolin-3-yl]benzoyl]-(R)-2-ethoxycarbonyl-(R)-4-methylpiperidine

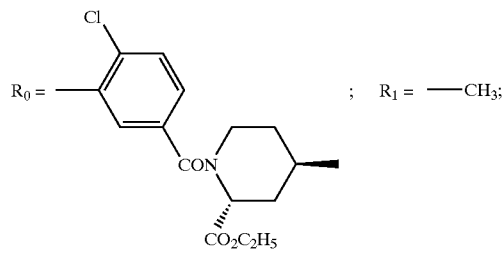

$R_2 = H$; $R_3 = 4\text{-}OCH_3$; $R_4 = 2\text{-}OCH_3$; $X = 5\text{-}Cl$; $Y = H$ Obtained according to b) of Example 166 with ethyl (R)-4-methyl-(R)-2-piperidinecarboxylate, described in J. Med. Chem., 37, 1994, 23, 3889–3901. The expected product, crystallized from pentane, is isolated; M.p.=106° C.

Example 174

1-[4-Chloro-3-[5-chloro-1-(2,4-dimethoxybenzyl)-3-methyl-2-oxoindolin-3-yl]benzoyl]-(S)-2-methylpiperidine

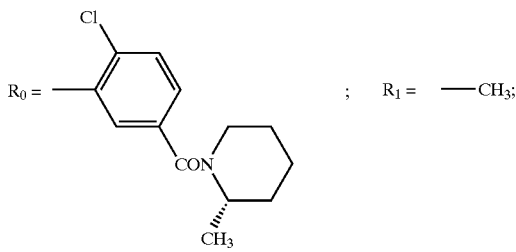

$R_2 = H$; $R_3 = 4\text{-}OCH_3$; $R_4 = 2\text{-}OCH_3$; $X = 5\text{-}Cl$; $Y = H$ Obtained according to b) of Example 166 with (S)-2-methylpiperidine, described in Tetrahedron Asymmetry, 8, 1997, 8, 1275–1278; M.p.=102° C. (0.5H$_2$O).

Example 175

1-[4-Chloro-3-[5-chloro-1-(2,4-dimethoxybenzyl)-3-methyl-2-oxoindolin-3-yl]benzoyl]-(R)-2-ethoxycarbonylpiperidine

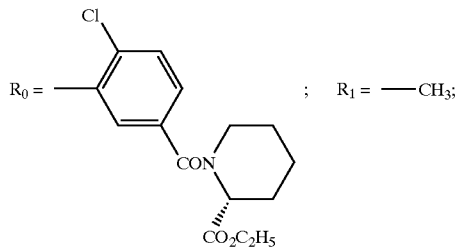

$R_2 = H$; $R_3 = 4\text{-}OCH_3$; $R_4 = 2\text{-}OCH_3$; $X = 5\text{-}Cl$; $Y = H$ Obtained according to b) of Example 166 with ethyl (R)-2-piperidinecarboxylate, described in J. Med. Chem., 42, 1999, 22, 4584–4603; M.p.=113° C.

Example 176

1-[4-Chloro-3-[5-chloro-1-(2,4-dimethoxybenzyl)-3-methyl-2-oxoindolin-3-yl]benzoyl]-(R)-2-tert-butyloxycarbonylpiperidine

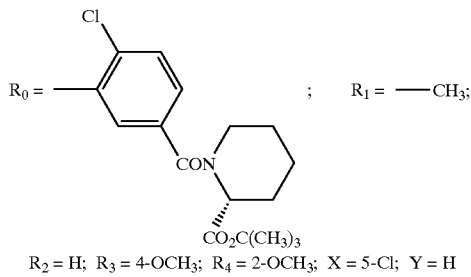

$R_2 = H$; $R_3 = 4\text{-}OCH_3$; $R_4 = 2\text{-}OCH_3$; $X = 5\text{-}Cl$; $Y = H$ a) tert-Butyl (R)-2-piperidinecarboxylate.

A mixture of 0.5 g of (R)-homoproline, 22 ml of dioxane, 2.2 ml of concentrated sulphuric acid and then approximately 20 ml of isobutylene, condensed at low temperature, is placed in an autoclave. After stirring at room temperature for twenty four hours, the medium, cooled to approximately −10° C., is poured onto 150 ml of an aqueous potassium carbonate solution and then extraction is carried out with ethyl acetate. The combined organic phases are washed with water, dried over NO$_2$SO$_4$ and evaporated to dryness. The residue is distilled under reduced pressure; B.p.=46° C. under 30 Pa.

b) Example 176 is obtained according to b) of Example 166 with the amine prepared in a). The expected product is crystallized from pentane; M.p.=202.2° C.

Example 177

4-Chloro-3-[5-chloro-1-(2,4-dimethoxybenzyl)-3-methyl-2-oxoindolin-3-yl]-N-ethyl-N-(2-dimethylaminoethyl)benzamide Hydrochloride

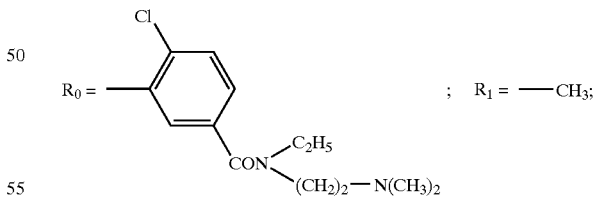

$R_2 = H$; $R_3 = 4\text{-}OCH_3$; $R_4 = 2\text{-}OCH_3$; $X = 5\text{-}Cl$; $Y = H$ Obtained according to b) of Example 166 with N-ethyl-2-dimethylaminoethylamine, described in J.A.C.S., 1963, 2256–2266. The hydrochloride of the expected compound is isolated from ethyl ether;

M.p.=171.5° C. (1H$_2$O); $[\alpha]_D^{20}$=+99 (c=1, methanol).

Example 178

4-Chloro-3-[5-chloro-1-(2,4-dimethoxybenzyl)-3-methyl-2-oxoindolin-3-yl]-N-ethyl-N-(2-morpholinoethyl)benzamide

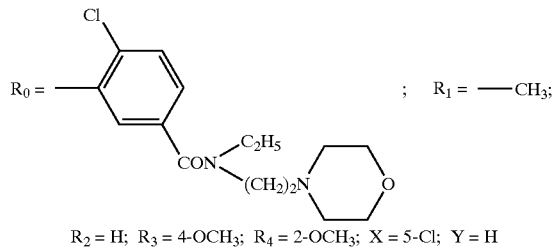

$R_2 = H$; $R_3 = 4\text{-}OCH_3$; $R_4 = 2\text{-}OCH_3$; $X = 5\text{-}Cl$; $Y = H$ Obtained according to b) of Example 166 with N-ethyl-2-morpholinoethylamine, described in Chem. Pharm. Bull., 45, 1997, 6, 996–1007; M.p.=143° C. (0.5H$_2$O).

Example 179

4-Chloro-3-[5-chloro-1-(2,4-dimethoxybenzyl)-3-methyl-2-oxoindolin-3-yl]-N-ethyl-N-[2-(pyrid-4-yl)ethyl]benzamide

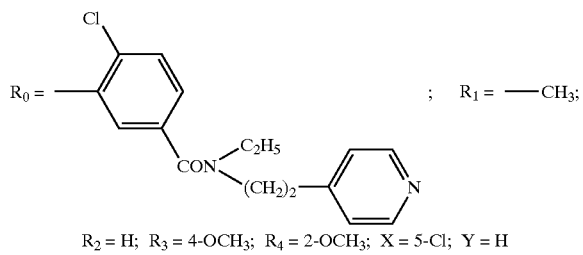

$R_2 = H$; $R_3 = 4\text{-}OCH_3$; $R_4 = 2\text{-}OCH_3$; $X = 5\text{-}Cl$; $Y = H$ Obtained according to b) of Example 166 with N-ethyl-2-(pyrid-4-yl)ethylamine, described in J.A.C.S., 1956, 78, 4441. The hydrochloride of the expected product is isolated from ethyl ether;
M.p.=185° C. (1.5H$_2$O).

Example 180

4-Chloro-3-[5-chloro-1-(2,4-dimethoxybenzyl)-3-methyl-2-oxoindolin-3-yl]-N-ethyl-N-(2,2,2-trifluoroethyl)benzamide

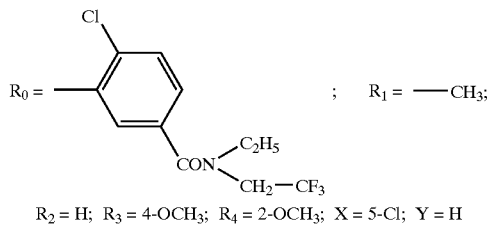

$R_2 = H$; $R_3 = 4\text{-}OCH_3$; $R_4 = 2\text{-}OCH_3$; $X = 5\text{-}Cl$; $Y = H$ Obtained according to b) of Example 166 with N-ethyl-2,2,2-trifluoroethylamine, described in J.A.C.S., 113, 1991, 4, 1288–1294; M.p.=80° C. (0.5H$_2$O).

Example 181

4-Chloro-3-[5-chloro-1-(2,4-dimethoxybenzyl)-3-methyl-2-oxoindolin-3-yl]-N-ethyl-N-[2-(pyrid-2-yl)ethyl]benzamide Hydrochloride

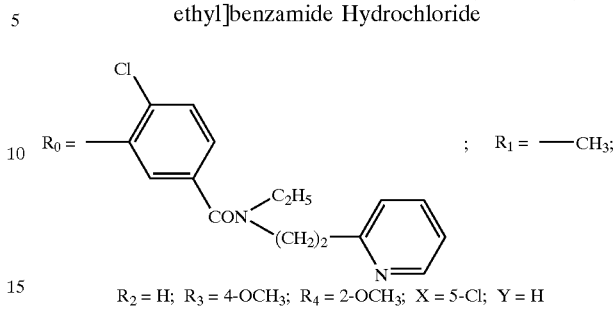

$R_2 = H$; $R_3 = 4\text{-}OCH_3$; $R_4 = 2\text{-}OCH_3$; $X = 5\text{-}Cl$; $Y = H$ Obtained according to b) of Example 166 with N-ethyl-2-(pyrid-2-yl)ethylamine, described in J.A.C.S., 1955, 5434.
The hydrochloride of the expected product is isolated from ethyl ether; M.p.=202° C. (1H$_2$O).

Example 182

4-Chloro-3-[5-chloro-1-(2,4-dimethoxybenzyl)-3-methyl-2-oxoindolin-3-yl]-N-ethyl-N-(2-pyrrolidinoethyl)benzamide Hydrochloride

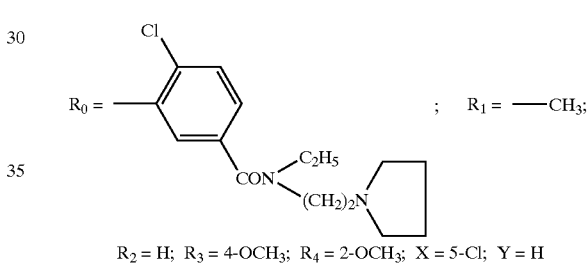

$R_2 = H$; $R_3 = 4\text{-}OCH_3$; $R_4 = 2\text{-}OCH_3$; $X = 5\text{-}Cl$; $Y = H$ Obtained according to b) of Example 166 with N-ethyl-2-pyrrolidinoethylamine, described in J. Med. Chem., 35, 1992, 1, 38–47. The hydrochloride of the product obtained is isolated from ethyl ether;
M.p.=109° C. (1.5H$_2$O).

Example 183

4-Chloro-3-[5-chloro-1-(2,4-dimethoxybenzyl)-3-methyl-2-oxoindolin-3-yl]-N-ethyl-N-(2-piperidinoethyl)benzamide Hydrochloride

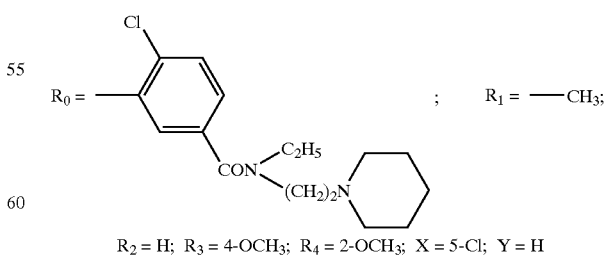

$R_2 = H$; $R_3 = 4\text{-}OCH_3$; $R_4 = 2\text{-}OCH_3$; $X = 5\text{-}Cl$; $Y = H$ Obtained according to b) of Example 166 with N-ethyl-2-piperidinoethylamine, described in Chem. Pharm. Bull., 1997, 45, 6, 996–1007.

Examples 184 to 198

The [lacuna] following Examples 184 to 198 are obtained under the conditions b) of Example 166 and with commercially available amines:

TABLE 18

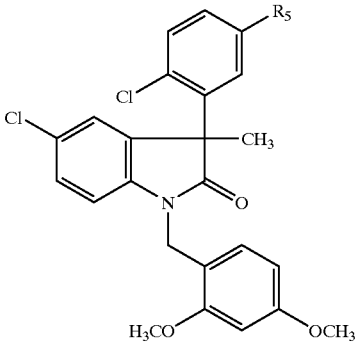

| EXAMPLES | R₅ | M.p.; °C. [α]²⁰_D |
|---|---|---|
| 184 | —CON(Et)CH₂CH₂OCH₃ | 86.3 |
| 185 | —CON(Et)CH₂-phenyl | 111.7 |
| 186 | —CON(Me)CH₂CH₂-(2-pyridyl) | 80.5 0.5 H₂O |
| 187 | —CON(Et)CH(CH₃)₂ | 102.8 |
| 188 | —CON(Et)CH₂-(4-pyridyl) | 193.7 +96.8 0.5 (c = 1, H₂O methanol) 1 HCl |
| 189 | 2,6-dimethylpiperidin-1-yl-CO— | 119.5 H₂O |
| 190 | 4-acetylpiperazin-1-yl-CO— | 112 0.5 H₂O |

TABLE 18-continued

| EXAMPLES | R₅ | M.p.; °C. [α]²⁰_D |
|---|---|---|
| 191 | —CON(piperidin-4-yl)-NHCO—O—tBu | 130 1.5 H₂O |
| 192 | —CONH-cyclohexyl | 129.8 +114° (c = 1, ethyl acetate) |
| 193 | —CON(Et)-cyclohexyl | 131 |
| 194 | 3-hydroxypiperidin-1-yl-CO— | 124 2 H₂O |
| 195 | (3R)-3-hydroxypiperidin-1-yl-CO— | 199.4 1.5 H₂O |
| 196 | —CON(Me)CH₂CH₂CH₂N(Me)₂ | 109 0.5 H₂O |
| 197 | —CON(Et)-phenyl | 104 0.5 H₂O |
| 198 | —CON(Et)CH₂CH₂OH | 101 0.5 H₂O |

TABLE 18-continued

[structure image]

| EXAMPLES | R₅ | M.p.; °C. | $[\alpha]^{20}_D$ |
|---|---|---|---|
| 199 | —CON(piperidine)NH₂ | 188 | 1 HCl |

The compound of Example 199 is obtained by treating the compound of Example 191 with a solution of hydrochloric acid in ethyl acetate; the hydrochloride is isolated after evaporating the solvent and taking out the residue in pentane.

Example 200

4-Chloro-3-[5-chloro-1-(2,4-dimethoxybenzyl)-3-methyl-2-oxoindolin-3-yl]-N-ethyl-N-(2-pyridylmethyl)benzamide

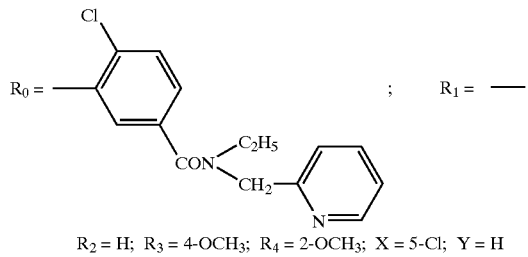

$R_2 = H$; $R_3 = 4\text{-}OCH_3$; $R_4 = 2\text{-}OCH_3$; $X = 5\text{-}Cl$; $Y = H$ a) N-Ethyl-2-pyridylmethylamine:

5 g of 2-pyridylcarboxaldehyde are added to the mixture of 3.8 g of ethylamine hydrochloride, 60 ml of toluene, 110 ml of ethanol and 13.2 ml of triethylamine. After stirring at 20° C. for 30 seconds, 25 g of 4 Å molecular sieve are added and stirring is maintained at 20° C. The insoluble material is filtered off, copious washing with dichloromethane is carried out, evaporation to dryness is carried out and the residue is taken up in 50 ml of methanol. 1.8 g of sodium borohydride are added to this solution at approximately 0° C. After sixteen hours at approximately 20° C., the solvent is evaporated under reduced pressure and the residue is taken up in dichloromethane. The organic phase is washed with 1N sodium hydroxide solution and then with an aqueous sodium chloride solution and dried over sodium sulphate, the solvent is evaporated under reduced pressure and then the residue is distilled; B.p.=64° C. under 180 Pa.

b) Example 200 is obtained according to b) of Example 166 with the amine prepared in a); M.p.=89° C. (0.5H₂O).

Example 201

4-Chloro-3-[5-chloro-1-(2,4-dimethoxybenzyl)-3-methyl-2-oxoindolin-3-yl]-N-ethyl-N-(3-pyridylmethyl)benzamide

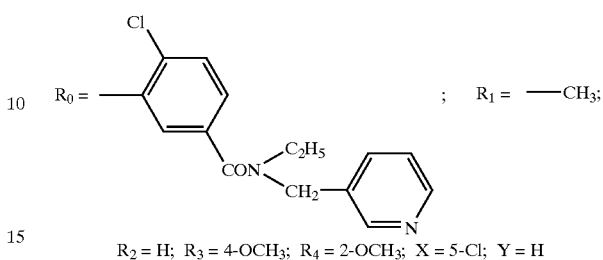

$R_2 = H$; $R_3 = 4\text{-}OCH_3$; $R_4 = 2\text{-}OCH_3$; $X = 5\text{-}Cl$; $Y = H$ a) N-Ethyl-3-pyridylmethylamine:

Obtained in the same way as in Example 200 a) from 3-pyridinecarboxaldehyde; B.p.=77° C. under 530 Pa.

b) Example 201 is obtained according to b) of Example 166 with the amine prepared in a); M.p.=95.5° C. (0.5H₂O).

Example 202

4-Chloro-3-[5-chloro-1-(2,4-dimethoxybenzyl)-3-methyl-2-oxoindolin-3-yl] -N-(2-dimethylaminoethyl)-N-(2,2,2-trifluoroethyl)benzamide Hydrochloride

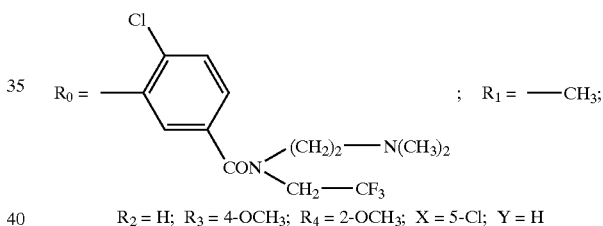

$R_2 = H$; $R_3 = 4\text{-}OCH_3$; $R_4 = 2\text{-}OCH_3$; $X = 5\text{-}Cl$; $Y = H$ a) N-(2-Dimethylaminoethyl)trifluoroacetamide:

11.5 ml of trifluoroacetic anhydride are added at approximately 0° C. to a solution of 6 g of 2-dimethylaminoethylamine in 150 ml of dichloromethane and 23.9 ml of triethylamine. 50 ml of a dilute sodium bicarbonate solution are added at 20° C., separation is carried out by settling, the organic phase is dried over sodium sulphate, the solvent is evaporated and the residue is distilled under reduced pressure;

B.p.=94° C. under 1975 Pa.

b) N-2,2,2-Trifluoroethyl-2-dimethylaminoethylamine:

A solution of 5 g of amide prepared in a) in 250 ml of ether is added to 2.78 g of lithium aluminium hydride in 50 ml of ethyl ether at approximately 0° C. After stirring overnight at 22° C., 20 ml of a saturated aqueous sodium sulphate solution are added, filtration is carried out through celite, the celite is washed with 3 times 100 ml of ether, the combined filtrates are partially evaporated and then treatment is carried out with a solution of hydrochloric acid in ethyl acetate. The hydrochloride of the expected product is filtered off; M.p.=232.6° C.

c) Example 202 is obtained according to b) of Example 166 with the amine prepared in b) and then salification with a solution of hydrochloric acid in ethyl ether; M.p.=201.5° C. (2H₂O).

Example 203

4-Chloro-3-[5-chloro-1-(2,4-dimethoxybenzyl)-3-methyl-2-oxoindolin-3-yl]-N-(3-dimethylaminopropyl)-N-ethylbenzamide Hydrochloride

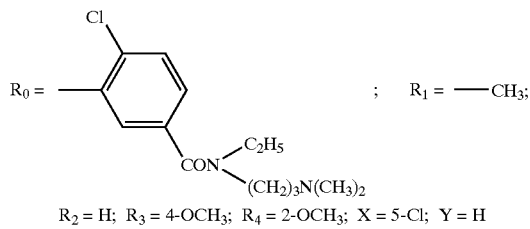

$R_2 = H$; $R_3 = 4\text{-}OCH_3$; $R_4 = 2\text{-}OCH_3$; $X = 5\text{-}Cl$; $Y = H$ a) N-(3-Dimethylaminopropyl)acetamide:

Obtained in the same way as in a) of Example 202 with acetic anhydride and 3-dimethylaminopropylamine; B.p.=91° C. under 84 Pa.

b) N-Ethyl-3-dimethylaminopropylamine:

Obtained under conditions analogous to those of b) of Example 202 in tetrahydrofuran at reflux;
B.p.=75° C. under 45 Pa.

c) Example 203 is obtained according to b) of Example 166 with the amine prepared in b). The hydrochloride is isolated by treatment with hydrochloric acid in ethyl ether; M.p.=222° C.

Example 204

4-Chloro-3-[5-chloro-1-(2,4-dimethoxybenzyl)-3-methyl-2-oxoindolin-3-yl]-N-ethyl-N-[3-(pyrid-4-yl)propyl]benzamide Hydrochloride

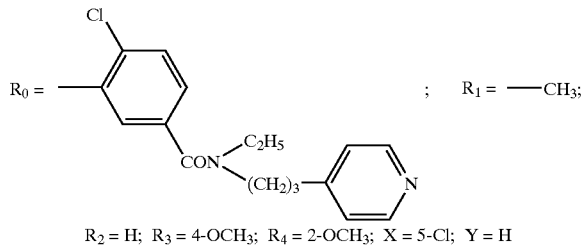

$R_2 = H$; $R_3 = 4\text{-}OCH_3$; $R_4 = 2\text{-}OCH_3$; $X = 5\text{-}Cl$; $Y = H$ a) N-Ethyl-3-(pyrid-4-yl)propylamine:

From 3-(pyrid-4-yl)propionaldehyde, described in J. Organometallic Chem., 599, 2, 2000, 298–303, and ethylamine hydrochloride, an oil is obtained analogously to a) of Example 200 and after purification on a column of silica, elution being carried out with a 90/10 dichloromethane/methanol mixture, which oil is used in the following stage.

b) Example 204 is obtained according to b) of Example 166 with the amine prepared in a). The expected product is isolated after purification on a column of silica, elution being carried out with a 97/3 dichloromethane/methanol mixture, and hydrochlorination with a solution of hydrochloric acid in ether;
M.p.=207° C.

Example 205

5-Chloro-3-[2-chloro-5-(2-oxopiperidinomethyl)phenyl]-1-(2,4-dimethoxybenzyl)-3-methylindolin-2-one

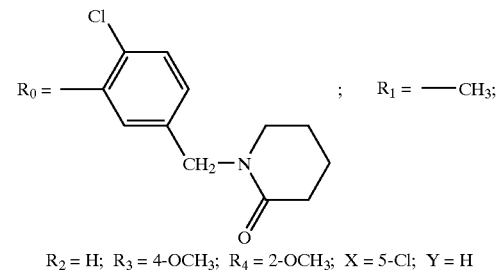

$R_2 = H$; $R_3 = 4\text{-}OCH_3$; $R_4 = 2\text{-}OCH_3$; $X = 5\text{-}Cl$; $Y = H$ 250 mg of the aldehyde prepared in a) of Example 145 are added to a solution of 90 mg of methyl 5-aminopentanoate hydrochloride in 3 ml of toluene, 2 ml of ethanol and 150 ml of triethylamine at approximately 0° C. Fifteen minutes later, 1.9 g of 4 Å molecular sieve are added. After 3 hours at approximately 20° C., the insoluble material is filtered off and is washed copiously with dichloromethane, and the solvents of the filtrate are evaporated under reduced pressure. The oil obtained is taken up in 4.1 ml of methanol and 20.1 mg of sodium borohydride are added at 0° C. After stirring for 16 hours at approximately 20° C., the solvent is evaporated under reduced pressure, the residue is taken up in dichloromethane and washing is carried out with a 0.5N aqueous sodium hydroxide solution and then with a dilute aqueous sodium chloride solution. The organic phase is dried over sodium sulphate, the solvent is evaporated under reduced pressure and the residue is chromatographed on a column of silica, elution being carried out with a 98/2 dichloromethane/methanol mixture. The expected product is crystallized from pentane; M.p.=72° C.

Example 206

1-[4-Chloro-3-[5-chloro-1-(4-chloro-2-methoxybenzyl)-3-methyl-2-oxoindolin-3-yl]benzoyl]piperidine

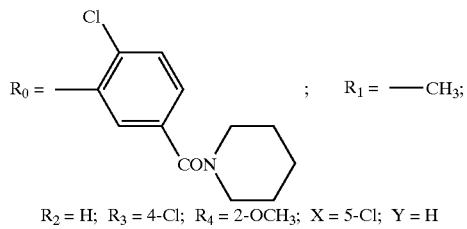

$R_2 = H$; $R_3 = 4\text{-}Cl$; $R_4 = 2\text{-}OCH_3$; $X = 5\text{-}Cl$; $Y = H$ a) Methyl 4-chloro-3-[5-chloro-1-(4-chloro-2-methoxybenzyl)-3-hydroxy-2-oxoindolin-3-yl]benzoate:

From compound IV.2 and according to the procedure described in Example 20, the expected product is obtained after chromatography on a column of silica, elution being carried out with a 50/50 cyclohexane/dichloromethane mixture; M.p.=205° C.

b) Methyl 4-chloro-3-[3,5-dichloro-1-(4-chloro-2-methoxybenzyl)-2-oxoindolin-3-yl]benzoate:

Obtained according to a) of Preparation 13 from the compound described in a).

c). Methyl 4-chloro-3-[5-chloro-1-(4-chloro-1-(4-chloro-2-methoxybenzyl)-3H-2-oxoindolin-3-yl]benzoate; compound III.9:

Obtained according to b) of Preparation 13 from the compound described in b); M.p.=126° C.

d) Methyl 4-chloro-3-[5-chloro-1-(4-chloro-2-methoxybenzyl)-3-methyl-2-oxoindolin-3-yl]benzoate:

Obtained according to the procedure described in Example 37 from compound III.9; M.p.=158° C.

e) 4-Chloro -3-[5-chloro-1-(4-chloro-2-methoxybenzyl)-3-methyl-2-oxoindolin-3-yl]benzoic acid:

Obtained according to the operational mixture described in Example 101 from the compound obtained in d); M.p.= 199° C.

f) Example 206 is obtained in the same way as for Example 112 from the acid obtained in e); M.p.=86° C.

Example 207

1-[4-Chloro-3-[5-chloro-1-(4-chloro-2-methoxybenzyl)-3-methyl-2-oxoindolin-3-yl] benzoyl]-4-hydroxypiperidine

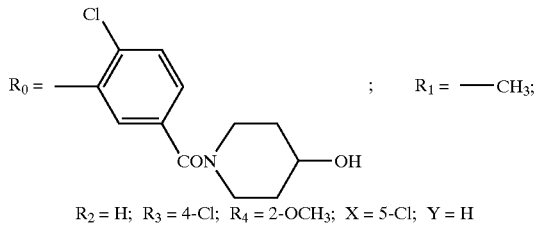

$R_2 = H$; $R_3 = 4\text{-Cl}$; $R_4 = 2\text{-OCH}_3$; $X = 5\text{-Cl}$; $Y = H$ Obtained in the same way as for Example 134 from the acid prepared in e) of Example 206;

M.p.=129° C. (1H$_2$O).

Example 208

1-[4-Chloro-3-[5-chloro-1-(4-chloro-2-methoxybenzyl)-3-methyl-2-oxoindolin-3-yl] benzoyl]-(R)-2-methoxycarbonylpiperidine

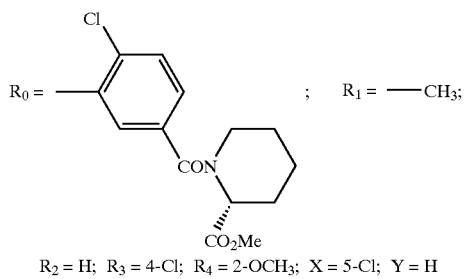

$R_2 = H$; $R_3 = 4\text{-Cl}$; $R_4 = 2\text{-OCH}_3$; $X = 5\text{-Cl}$; $Y = H$ Obtained in the same way as for Example 131 from the acid prepared in e) of Example 206;

M.p.=101° C.

Example 209

Methyl 4-Chloro-3-[5,7-dichloro-1-(2,4-dimethoxybenzyl)-3-methyl-2-oxoindolin-3-yl] benzoate

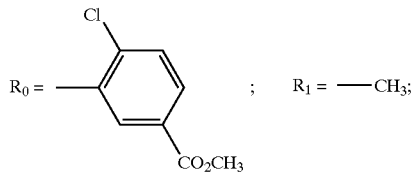

$R_2 = H$; $R_3 = 4\text{-OCH}_3$; $R_4 = 2\text{-OCH}_3$; $X = 5\text{-Cl}$; $Y = 7\text{-Cl}$ a) Methyl 4-chloro-3-[5,7-dichloro-1-(2,4-dimethoxybenzyl)-3-hydroxy-2-oxoindolin-3-yl]benzoate:

From compound IV.3 and according to the procedure described in Example 20, the product obtained is isolated; M.p.=225° C.

b) Methyl 4-chloro-3-[1-(2,4-dimethoxybenzyl)-3,5,7-trichloro-2-oxoindolin-3-yl]benzoate:

Obtained according to a) of Preparation 13 from the product described in a).

c) Methyl 4-chloro-3-[5,7-dichloro-1-(2,4-dimethoxybenzyl)-3H-2-oxoindolin-3-yl]benzoate; compound III.10:

Obtained according to b) of Preparation 13 from the product described in b); M.p.=173° C.

d) Example 209 is obtained according to the procedure described in Example 37 from the product compound III.10; M.p.=166° C.

Example 210

3-(5-Amino-2-chlorophenyl)-5,7-dichloro-1-(2,4-dimethoxybenzyl)-3-methylindolin-2-one

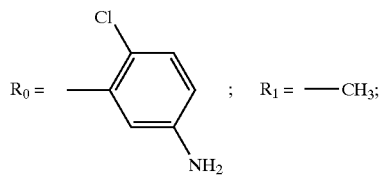

$R_2 = H$; $R_3 = 4\text{-OCH}_3$; $R_4 = 2\text{-OCH}_3$; $X = 5\text{-Cl}$; $Y = 7\text{-Cl}$ a) 3-(2-Chloro-5-aminophenyl)-5,7-dichloro-1-(2,4-dimethoxybenzyl)-3-hydroxyindolin-2-one:

Obtained from compound IV.3 and according to the procedure described in Example 21; M.p.=124° C.

b) 3-(2-Chloro-5-aminophenyl)-1-(2,4-dimethoxybenzyl)-3,5,7-trichloroindolin-2-one:

Obtained according to a) of Preparation 13 from the product described in a).

c) 3-(2-Chloro-5-aminophenyl)-1-(2,4-dimethoxybenzyl)-2,7-dichloro-3H-indolin-2-one; compound III.11:

Obtained according to b) of Preparation 13 from the product described in b); M.p.=118° C.

d) Example 210 is obtained according to the procedure described in Example 37 from the product compound III.11; M.p.=112° C.

Example 211

1-[4-Chloro-3-[5-chloro-1-(2,4-dimethoxybenzyl)-3-methyl-2-oxoindolin-3-yl]benzoyl]-4,4-difluoropiperidine

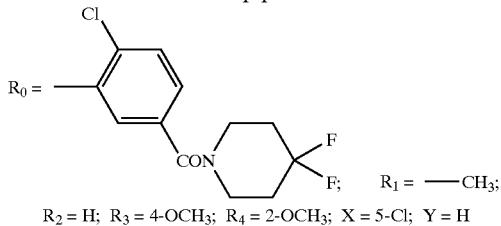

$R_2 = H$; $R_3 = 4\text{-}OCH_3$; $R_4 = 2\text{-}OCH_3$; $X = 5\text{-}Cl$; $Y = H$ Obtained according to b) of Example 166 with 4,4-difluoropiperidine, described in Chem. Pharm. Bull., 1993, 41, 11, 1971–1986; M.p.=98.5° C. (0.5H$_2$O).

Example 212

5-Chloro-3-(2-chlorophenyl)-1-[4-(2-butylamino)-2-methoxybenzyl]-3-methylindolin-2-one

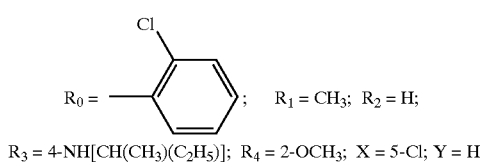

$R_1 = CH_3$; $R_2 = H$;
$R_3 = 4\text{-}NH[CH(CH_3)(C_2H_5)]$; $R_4 = 2\text{-}OCH_3$; $X = 5\text{-}Cl$; $Y = H$ Obtained under conditions analogous to those of Example 56; M.p.=158° C.

Example 213

5-Chloro-3-(2-chlorophenyl)-1-(4-isobutylamino-2-methoxybenzyl)-3-methylindolin-2-one

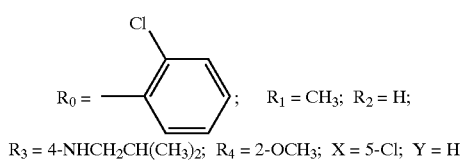

$R_1 = CH_3$; $R_2 = H$;
$R_3 = 4\text{-}NHCH_2CH(CH_3)_2$; $R_4 = 2\text{-}OCH_3$; $X = 5\text{-}Cl$; $Y = H$ Obtained under conditions analogous to those of Example 55; M.p.=136° C.

Example 214

4-Chloro-3-[5-fluoro-1-(2,4-dimethoxybenzyl)-3-methyl-2-oxoindolin-3-yl]-N,N-diethylbenzamide

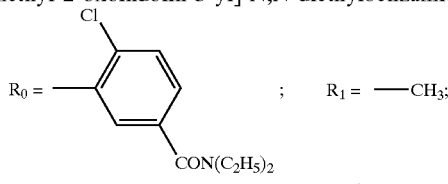

$R_2 = H$; $R_3 = 4\text{-}OCH_3$; $R_4 = 2\text{-}OCH_3$; $X = 5\text{-}F$; $Y = H$ a) Methyl 4-chloro-3-[1-(2,4-dimethoxybenzyl)-5-fluoro-3-hydroxy-2-oxoindolin-3-yl]benzoate:

From compound IV.4 and according to the procedure described in Example 20, the expected product is isolated; M.p.=188° C.

b) Methyl 4-chloro-3-[3-chloro-1-(2,4-dimethoxybenzyl)-5-fluoro-2-oxoindolin-3-yl]benzoate:

Obtained according to a) of Preparation 13 from the product described in a).

c) Methyl 4-chloro-3-[1-(2,4-dimethoxybenzyl)-5-fluoro-3H-2-oxoindolin-3-yl]benzoate; compound III.12:

Obtained according to b) of Preparation 13 from compound III.12; M.p.=138° C.

d) 4-Chloro-3-[1-(2,4-dimethoxybenzyl)-3-methyl-5-fluoro-2-oxoindolin-3-yl]benzoic acid:

From the product described in c) and according to the procedure of Example 37, the methyl ester of the expected compound is obtained, which ester is used directly in the saponification reaction under the conditions of Example 101; M.p.=89° C.

e) The racemic compound of Example 214 is obtained under the conditions of Example 102; M.p.=79° C.

Example 215

4-Chloro-3-[1-(2,4-dimethoxybenzyl)-3-methyl-2-oxoindolin-3-yl]-N,N-diethylbenzamide

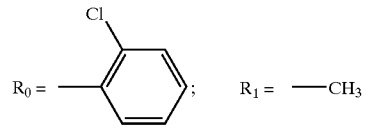

$R_2 = H$; $R_3 = 4\text{-}OCH_3$; $R_4 = 2\text{-}OCH_3$; $X = H$; $Y = H$ a) Methyl 4-chloro-3-[1-(2,4-dimethoxybenzyl)-3-hydroxy-2-oxoindolin-3-yl]benzoate:

From compound IV.5 and according to the procedure described in Example 20, the expected product is isolated; M.p.=172° C.

b) Methyl 4-chloro-3-[3-chloro-1-(2,4-dimethoxybenzyl)-2-oxoindolin-3-yl]benzoate:

Obtained according to a) of Preparation 13 from the product described in a).

c) Methyl 4-chloro-3-[1-(2,4-dimethbxybenzyl)-3H-2-oxoindolin-3-yl]benzoate; compound III.13:

Obtained according to b) of Preparation 13 from compound III.13; M.p.=122° C.

d) 4-Chloro-3-[1-(2,4-dimethoxybenzyl)-3-methyl-2-oxoindolin-3-yl]benzoic acid:

From the product described in c) and according to the procedure of Example 37, the methyl ester of the expected compound is obtained, which ester is used directly in the saponification reaction under the conditions of Example 101; M.p.=103° C.

e) The racemic compound of Example 215 is obtained under the conditions of Example 102; M.p.=85° C.

What is claimed is:

1. A compound in the form of a pure enantiomer or of a mixture of enantiomers of formula:

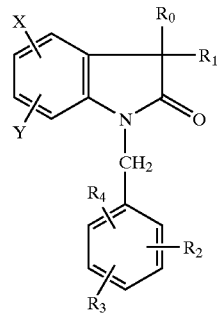

(I)

in which:

$R_0$ represents a group chosen from:

(i):

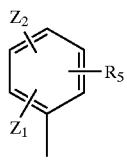

in which:

$Z_1$ represents a chlorine, bromine, iodine or fluorine atom or a $(C_1-C_4)$alkyl, $(C_1-C_4)$alkoxy or trifluoromethyl group;

$Z_2$ represents a hydrogen, chlorine, bromine, iodine or fluorine atom or a $(C_1-C_4)$alkyl, $(C_3-C_5)$cycloalkyl, $(C_1-C_4)$alkoxy, $(C_3-C_5)$cycloalkoxy or polyfluoro$(C_1-C_4)$alkyl group;

$R_5$ represents $T_1W$ in which $T_1$ represents —$(CH_2)_m$—, it being possible for m to be equal to 0 or 1, and W represents a hydrogen atom or a hydroxycarbonyl (or carboxyl), $(C_1-C_4)$alkoxycarbonyl, 1,3-dioxolan-2-yl or 1,3-dioxan-2-yl group, or else W represents an —$NR_6R_7$ group in which $R_6$ and $R_7$ represent, independently of one another, a hydrogen atom, a $(C_1-C_4)$alkyl group, a $(C_1-C_4)$alkylsulphonyl group or a phenylsulphonyl group in which the phenyl group can be mono-, di- or trisubstituted by $Z_5$; or else $R_6$ and $R_7$ form, with the nitrogen atom to which they are bonded, a morpholinyl group optionally substituted by a $(C_1-C_4)$alkyl group or an oxo; or else $R_6$ and $R_7$ form, with the nitrogen atom to which they are bonded, a piperazinyl group optionally substituted in the 4-position by a $Z_3$ substituent; or else $R_6$ and $R_7$ form, with the nitrogen atom to which they are bonded, a pyrrolidinyl or piperidyl group, the said pyrrolidinyl and piperidyl groups optionally being substituted by $Z_4$;

or else W represents an —$NR_8COR_9$ group in which $R_8$ represents a hydrogen atom or a $(C_1-C_4)$alkyl group and $R_9$ represents a hydrogen atom or a $(C_1-C_4)$alkyl, benzyl, pyridyl or phenyl group, it being possible for the said phenyl group to be mono-, di- or trisubstituted by $Z_5$; or else $R_9$ represents an —$NR_{10}R_{11}$ group in which $R_{10}$ and $R_{11}$ represent, independently of one another, a hydrogen atom or a $(C_1-C_4)$alkyl group or else $R_{10}$ and $R_{11}$ form, with the nitrogen atom to which they are bonded, a pyrrolidinyl, piperidyl or morpholinyl group optionally substituted by a $(C_1-C_4)$alkyl group; or else $R_9$ represents a pyrrolidin-2-yl or -3-yl or piperid-2-yl, -3-yl or 4-yl group, the said pyrrolidinyl and piperidyl groups optionally being substituted by $Z_7$; or else $R_9$ represents a —$T_2$—$R_{12}$ or —$T_2$—$COR_{12}$ group in which $T_2$ represents —$(CH_2)_n$—, it being possible for n to be equal to 1, 2, 3 and 4, and $R_{12}$ represents a $(C_1-C_4)$alkoxy or —$NR_{10}R_{11}$ group, $R_{10}$ and $R_{11}$ being as defined above;

or else W represents a —$CONR_{13}R_{14}$ group in which $R_{13}$ represents a hydrogen atom or a $(C_1-C_4)$alkyl, $(C_3-C_7)$cycloalkyl, monofluoro$(C_1-C_4)$alkyl or polyfluoro$(C_1-C_4)$alkyl group and $R_{14}$ represents a hydrogen atom, a $(C_1-C_4)$alkyl group, a phenyl group optionally substituted by $Z_5$, a —$T_4$—$R_{15}$ group in which $T_4$ represents —$(CH_2)_q$—, with q equal to 1, 2, 3 or 4, and $R_{15}$ represents a hydroxyl group, a $(C_1-C_4)$alkoxy group, a $(C_1-C_4)$alkoxycarbonyl group, a $(C_1-C_4)$alkoxycarbonylamino group, a phenyl group optionally mono- or disubstituted by $Z_5$, a pyrid-2-yl, -3-yl or -4-yl, or an —$NR_{16}R_{17}$ group in which $R_{16}$ and $R_{17}$ represent, independently of one another, a hydrogen atom or a $(C_1-C_4)$alkyl group or else $R_{16}$ and $R_{17}$ form, with the nitrogen atom to which they are bonded, a morpholinyl group optionally mono- or disubstituted by a $(C_1-C_4)$alkyl group or else $R_{16}$ and $R_{17}$ form, with the nitrogen atom to which they are bonded, a piperazinyl group optionally substituted in the 4-position by a $Z_3$ substituent or else $R_{16}$ and $R_{17}$ form, with the nitrogen atom to which they are bonded, a pyrrolidinyl or piperidyl group, the said pyrrolidinyl and piperidyl groups optionally being substituted by Z5, it being understood that, when q=1, $R_{15}$ is other than hydroxyl, $(C_1-C_4)$alkoxy, $(C_1-C_4)$alkoxycarbonylamino or —$NR_{16}R_{17}$; or else $R_{13}$ and $R_{14}$ form, with the nitrogen atom to which they are bonded, a morpholinyl group optionally mono- or disubstituted by a $(C_1-C_4)$alkyl group or a piperazinyl group optionally substituted in the 4-position by a $Z_3$ substituent; or else $R_{13}$ and $R_{14}$ form, with the nitrogen atom to which they are bonded, an azetidinyl, pyrrolidinyl, piperidyl or hexahydroazepinyl group, the said pyrrolidinyl, piperidyl and hexahydroazepinyl groups optionally being mono- or disubstituted by $Z_8$;

or else W represents an $OR_{18}$ group in which $R_{18}$ represents a hydrogen atom or a $(C_1-C_4)$alkyl, $(C_1-C_4)$alkoxy$(C_1-C_4)$alkyl or —$T_3$—$R_{19}$ group in which $T_3$ represents —$(CH_2)_p$—, it being possible for p to be equal to 2 or 3, and $R_{19}$ is chosen from the hydroxyl, triphenylmethoxy or —$NR_{20}R_{21}$ groups in which $R_{20}$ represents a hydrogen atom or a $(C_1-C_4)$alkyl group and $R_{21}$ represents a hydrogen atom or a $(C_1$–$C_4)$alkyl, tetrahydrofuranylmethyl or tetrahydropyranylmethyl group, or else $R_{20}$ and $R_{21}$ form, with the nitrogen atom to which they are bonded, a morpholinyl group optionally mono- or disubstituted by a $(C_1$–$C_4)$alkyl group or a piperazinyl group optionally substituted in the 4-position by a $Z_3$ substituent, or else $R_{20}$ and $R_{21}$ form, with the nitrogen atom to which they are bonded, a pyrrolidinyl or piperidyl group, the said pyrrolidinyl and piperidyl groups optionally being substituted by $Z_5$;

$Z_3$ represents a $(C_1$–$C_4)$alkyl, pyridyl, phenyl, $(C_1$–$C_4)$alkylcarbonyl or $(C_1$–$C_4)$alkoxycarbonyl group;

$Z_4$ represents an oxo, a fluorine atom, a hydroxyl, a $(C_1$–$C_4)$alkyl, a benzyl, an amino, a $(C_1$–$C_4)$alkylamino, a di$(C_1$–$C_4)$alkylamino, a $(C_1$–$C_4)$alkoxy, a $(C_1$–$C_4)$alkoxycarbonyl or a $(C_1$–$C_4)$alkoxycarbonylamino;

$Z_5$ represents a chlorine, bromine, iodine or fluorine atom, a hydroxyl group, a $(C_1$–$C_4)$alkyl group or a $(C_1$–$C_4)$alkoxy group;

$Z_7$ represents a fluorine atom, a hydroxyl group, a hydroxy$(C_1$–$C_4)$alkyl group, a $(C_1$–$C_4)$alkyl group, a $(C_1$–$C_4)$alkoxy group or a $(C_1$–$C_4)$alkylcarbonyl group;

$Z_8$ represents a fluorine atom or a hydroxyl, $(C_1$–$C_4)$alkyl, $(C_3$–$C_6)$cycloalkyl, benzyl, amino, $(C_1$–$C_4)$alkylamino, di$(C_1$–$C_4)$alkylamino, $(C_1$–$C_4)$alkoxycarbonyl, $(C_1$–$C_4)$alkoxycarbonylamino, $(C_3$–$C_6)$cycloalkoxy, hydroxycarbonyl, hydroxy$(C_1$–$C_4)$alkyl, $(C_1$–$C_4)$alkoxy$(C_1$–$C_4)$alkyl, $(C_1$–$C_4)$alkoxy or —CONR$_{23}$R$_{24}$ group in which $R_{23}$ and $R_{24}$ represent, independently of one another, a hydrogen atom, a $(C_1$–$C_4)$alkyl, a monofluoro$(C_1$–$C_4)$alkyl or a polyfluoro$(C_1$–$C_4)$alkyl, or else $R_{23}$ and $R_{24}$ form, with the nitrogen atom to which they are bonded, a pyrrolidinyl or piperidyl group, the said pyrrolidinyl or piperidyl groups optionally being substituted by $Z_3$ or a difluoromethylidene;

(ii)

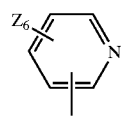

$Z_6$ represents a chlorine atom or a $(C_1$–$C_4)$alkyl or $(C_1$–$C_4)$alkoxy group;

$R_1$ represents a $(C_1$–$C_4)$alkyl group optionally comprising a double or a triple bond, a $(C_1$–$C_4)$alkoxycarbonyl group, a phenyloxycarbonyl group or a $T_1$—$R_{22}$ group in which $T_1$ is as defined above and $R_{22}$ represents a hydroxyl or $(C_1$–$C_4)$alkoxy group;

$R_2$ and $R_4$ represent, independently of one another, a hydrogen, chlorine or fluorine atom or a $(C_1$–$C_4)$alkyl or $(C_1$–$C_4)$alkoxy group;

$R_3$ represents a chlorine or fluorine atom or a $(C_1$–$C_4)$alkyl, $(C_1$–$C_4)$alkoxy, $(C_1$–$C_4)$carbamoyl, $(C_1$–$C_4)$alkylcarbonylamino, nitro, cyano, trifluoromethyl, amino, $(C_3$–$C_6)$cycloalkylamino, $(C_1$–$C_4)$alkylamino, di$(C_1$–$C_4)$alkylamino, tri$(C_1$–C4$)$alkylammonium A$^-$, A$^-$ being an anion, pyrrolidin-1-yl, piperid-1-yl, piperazin-1-yl, morpholin-4-yl or hexahydroazepin-1-yl group;

X and Y represent, independently of one another, a hydrogen, chlorine, bromine, iodine or fluorine atom or a $(C_1$–$C_4)$alkoxy or trifluoromethoxy group;

or a pharmaceutically acceptable salt, solvate and/or hydrate thereof.

2. A compound according to claim 1 in the form of a pure enantiomer or of a mixture of enantiomers of formula:

(I)

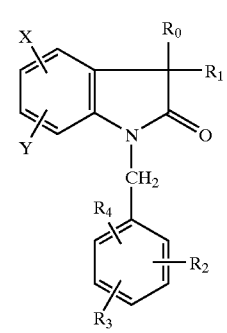

in which:

$R_0$ represents (i):

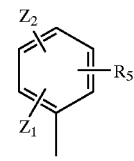

$Z_1$, $Z_2$, $R_1$, $R_2$, $R_3$, $R_4$, $R_5$, Y and X being as defined for (I), or a pharmaceutically acceptable salt, solvate and/or hydrate thereof.

3. A compound according to claim 2 of formula:

(Ia)

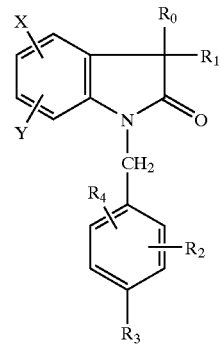

in which $R_1$ represents a methyl or hydroxyl group and $R_0$, $R_2$, $R_3$, $R_4$, X and Y are as defined for (I), in the form of a pure enantiomer or of a mixture of enantiomers, or a pharmaceutically acceptable salt, solvate and/or hydrate thereof.

4. A compound according to claim 3 of formula:

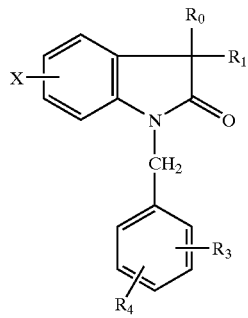
(Ib)

in which $R_1$ represents a methyl or hydroxyl group and $R_0$, $R_3$, $R_4$ and X are as defined for (I), in the form of a pure enantiomer or of a mixture of enantiomers, or a pharmaceutically acceptable salt, solvate and/or hydrate thereof.

5. A compound according to claim 4 of formula:

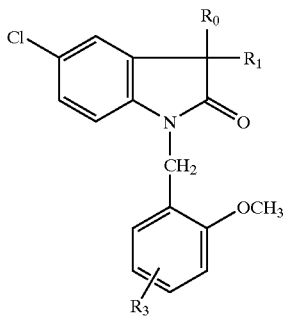
(Ic)

in which $R_1$ represents a methyl or hydroxyl group and $R_0$ and $R_3$ are as defined for (I), in the form of a pure enantiomer or of a mixture of enantiomers, or a pharmaceutically acceptable salt, solvate and/or hydrate thereof.

6. A compound according to claim 5 of formula:

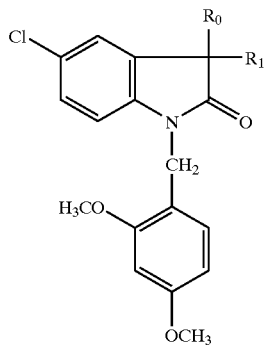
(Id)

in which $R_1$ represents a methyl or hydroxyl group and $R_0$ is as defined for (I), in the form of (a pure enantiomer or of a mixture of enantiomers, or a pharmaceutically acceptable salt, solvate and/or hydrate thereof.

7. A compound according to claim 6 in which $R_0$ represents the group:

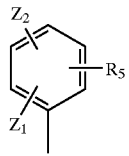

$Z_1$, $Z_2$ and $R_5$ being as defined for (I).

8. A compound according to claim 7 in which $R_0$ represents the group:

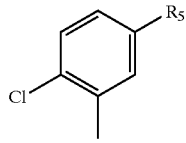

$R_5$ being as defined for (I).

9. A compound according to claim 8 in which $R_1$ represents a methyl group.

10. A compound according to claim 1 chosen from:
   5-Chloro-3-(2-chlorophenyl)-1-(2,4-dimethoxybenzyl)-3-methylindolin-2-one;
   5-Chloro-3-(2-chlorophenyl)-1-[4-(isopropylamino)-2-methoxybenzyl]-3-methylindolin-2-one;
   N-{4-Chloro-3-[5-chloro-1-(2,4-dimethoxybenzyl)-3-methyl-2-oxoindolin-3-yl]phenyl}acetamide;
   N-{4-Chloro-3-[5-chloro-1-(2,4-dimethoxybenzyl)-3-methyl-2-oxoindolin-3-yl]phenyl}-3-methylbutanamide;
   N-{4-Chloro-3-[5-chloro-1-(2,4-dimethoxybenzyl)-3-methyl-2-oxoindolin-3-yl]phenyl}benzamide;
   N-{4-Chloro-3-[5-chloro-1-(2,4-dimethoxybenzyl)-3-methyl-2-oxoindolin-3-yl]phenyl}nicotinamide;
   N-{4-Chloro-3-[5-chloro-1-(2,4-dimethoxybenzyl)-3-methyl-2-oxoindolin-3-yl]phenyl}-2-methoxyacetamide;
   Methyl 3-{4-chloro-3-[5-chloro-1-(2,4-dimethoxybenzyl)-3-methyl-2-oxoindolin-3-yl]anilino}-3-oxopropanoate;
   N-{4-Chloro-3-[5-chloro-1-(2,4-dimethoxybenzyl)-3-methyl-2-oxoindolin-3-yl]phenyl}-3-methoxypropanamide;
   N-{4-Chloro-3-[5-chloro-1-(2,4-dimethoxybenzyl)-3-methyl-2-oxoindolin-3-yl]phenyl}-N-methylacetamide;
   N-{4-Chloro-3-[5-chloro-1-(2,4-dimethoxybenzyl)-3-methyl-2-oxoindolin-3-yl]phenyl}-N-methylmethanesulphonamide;
   4-Chloro-3-[5-chloro-1-(2,4-dimethoxybenzyl)-3-methyl-2-oxoindolin-3-yl]-N,N-diethylbenzamide;
   4-Chloro-3-[5-chloro-1-(2,4-dimethoxybenzyl)-3-methyl-2-oxoindolin-3-yl]-N,N-dimethylbenzamide;
   5-Chloro-3-[2-chloro-5-(1-piperidylcarbonyl)phenyl]-1-(2,4-dimethoxybenzyl)-3-methylindolin-2-one;
   4-Chloro-3-[5-chloro-1-(2,4-dimethoxybenzyl)-3-methyl-2-oxoindolin-3-yl]-N-ethylbenzamide;
   5-Chloro-3-(2-chloro-5-{[2-(methoxymethyl)-1-pyrrolidinyl]carbonyl}phenyl)-1-(2,4-dimethoxybenzyl)-3-methylindolin-2-one;
   5-Chloro-3-{2-chloro-5-[(2-methyl-1-piperidyl)carbonyl]phenyl}-1-(2,4-dimethoxybenzyl)-3-methylindolin-2-one;

4-Chloro-3-[5-chloro-1-(2,4-dimethoxybenzyl)-3-methyl-2-oxoindolin-3-yl]-N-ethyl-N-methylbenzamide;

Methyl 1-{4-chloro-3-[5-chloro-1-(2,4-dimethoxybenzyl)-3-methyl-2-oxoindolin-3-yl]benzoyl}-2-piperidinecarboxylate;

5-Chloro-3-{2-chloro-5-[(4-hydroxy-1-piperidyl)carbonyl]phenyl}-1-(2,4-dimethoxybenzyl)-3-methylindolin-2-one;

5-Chloro-3-{2-chloro-5-[(2-methoxyethoxy)methyl]phenyl}-1-(2,4-dimethoxybenzyl)-3-methylindolin-2-one;

5-Chloro-3-[2-chloro-5-(4-morpholinylmethyl)phenyl]-1-(2,4-dimethoxybenzyl)-3-methylindolin-2-one;

5-Chloro-3-(2-chloro-5-{[2-(4-morpholinyl)ethoxy]methyl}phenyl)-1-(2,4-dimethoxybenzyl)-3-methylindolin-2-one;

1-[4-Chloro-3-[5-chloro-1-(2,4-dimethoxybenzyl)-3-methyl-2-oxoindolin-3-yl]benzoyl]-3-hydroxypiperidine;

1-[4-Chloro-3-[5-chloro-1-(2,4-dimethoxybenzyl)-3-methyl-2-oxoindolin-3-yl]benzoyl]-(R)-3-hydroxypiperidine;

1-[4-Chloro-3-[5-chloro-1-(2,4-dimethoxybenzyl)-3-methyl-2-oxoindolin-3-yl]benzoyl]-4-methoxypiperidine;

1-[4-Chloro-3-[5-chloro-1-(2,4-dimethoxybenzyl)-3-methyl-2-oxoindolin-3-yl]benzoyl-4-ethoxypiperidine;

1-[4-Chloro-3-[5-chloro-1-(2,4-dimethoxybenzyl)-3-methyl-2-oxoindolin-3-yl]benzoyl]-(R,S)-2,6-dimethylpiperidine;

1-[4-Chloro-3-[5-chloro-1-(2,4-dimethoxybenzyl)-3-methyl-2-oxoindolin-3-yl]benzoyl]-(R)-2-ethoxycarbonylpiperidine;

1-[4-Chloro-3-[5-chloro-1-(2,4-dimethoxybenzyl)-3-methyl-2-oxoindolin-3-yl]benzoyl]-(R)-2-N,N-dimethylaminocarbonylpiperidine;

1-[4-Chloro-3-[5-chloro-1-(2,4-dimethoxybenzyl)-3-methyl-2-oxoindolin-3-yl]benzoyl]-(R)-2-(N-methyl-N-2,2,2-trifluoroethylaminocarbonyl)piperidine;

1-[4-Chloro-3-[5-chloro-1-(2,4-dimethoxybenzyl)-3-methyl-2-oxoindolin-3-yl]benzoyl]-(R)-2-pyrrolidinocarbonylpiperidine;

1-[4-Chloro-3-[5-chloro-1-(2,4-dimethoxybenzyl)-3-methyl-2-oxoindolin-3-yl]benzoyl]-(S)-2-methylpiperidine;

4-Chloro-3-[5-chloro-1-(2,4-dimethoxybenzyl)-3-methyl-2-oxoindolin-3-yl]-N-ethyl-N-(2-phenylethyl)benzamide;

4-Chloro-3-[5-chloro-1-(2,4-dimethoxybenzyl)-3-methyl-2-oxoindolin-3-yl]-N-ethyl-N-(4-pyridylmethyl)-benzamide hydrochloride;

4-Chloro-3-[5-chloro-1-(2,4-dimethoxybenzyl)-3-methyl-2-oxoindolin-3-yl]-N-ethyl-N-(3-pyridylmethyl)benzamide;

4-Chloro-3-[5-chloro-1-(2,4-dimethoxybenzyl)-3-methyl-2-oxoindolin-3-yl]-N-ethyl-N-(2-pyridylmethyl)benzamide;

4-Chloro-3-[5-chloro-1-(2,4-dimethoxybenzyl)-3-methyl-2-oxoindolin-3-yl]-N-ethyl-N-(2-methoxyethyl)benzamide;

4-Chloro-3-[5-chloro-1-(2,4-dimethoxybenzyl)-3-methyl-2-oxoindolin-3-yl]-N-ethyl-N-(2-dimethylaminoethyl)benzamide hydrochloride;

4-Chloro-3-[5-chloro-1-(2,4-dimethoxybenzyl)-3-methyl-2-oxoindolin-3-yl]-N-ethyl-N-(2-morpholinoethyl)benzamide;

4-Chloro-3-[5-chloro-1-(2,4-dimethoxybenzyl)-3-methyl-2-oxoindolin-3-yl]-N-ethyl-N-(2-pyrrolidinoethyl)benzamide hydrochloride;

4-Chloro-3-[5-chloro-1-(2,4-dimethoxybenzyl)-3-methyl-2-oxoindolin-3-yl]-N-ethyl-N-(2-piperidinoethyl)benzamide hydrochloride;

4-Chloro-3-[5-chloro-1-(2,4-dimethoxybenzyl)-3-methyl-2-oxoindolin-3-yl]-N-ethyl-N-(2-hydroxyethyl)benzamide;

4-Chloro-3-[5-chloro-1-(2,4-dimethoxybenzyl)-3-methyl-2-oxoindolin-3-yl]-N-ethyl-N-[2-(pyrid-4-yl)ethyl]benzamide hydrochloride;

4-Chloro-3-[5-chloro-1-(2,4-dimethoxybenzyl)-3-methyl-2-oxoindolin-3-yl]-N-ethyl-N-(2,2,2-trifluoroethyl)benzamide;

4-Chloro-3-[5-chloro-1-(2,4-dimethoxybenzyl)-3-methyl-2-oxoindolin-3-yl]-N-methyl-N-(2,2,2-trifluoroethyl)benzamide;

4-Chloro-3-[5-chloro-1-(2,4-dimethoxybenzyl)-3-methyl-2-oxoindolin-3-yl]-N-ethyl-N-isopropylbenzamide;

4-Chloro-3-[5-chloro-1-(2,4-dimethoxybenzyl)-3-methyl-2-oxoindolin-3-yl]-N-(2-dimethylaminoethyl)-N-(2,2,2-trifluoroethyl)benzamide hydrochloride;

4-Chloro-3-[5-chloro-1-(2,4-dimethoxybenzyl)-3-methyl-2-oxoindolin-3-yl]-N-cyclohexylbenzamide; and 4-Chloro-3-[5-chloro-1-(2,4-dimethoxybenzyl)-3-methyl-2-oxoindolin-3-yl]-N-ethyl-N-[3-(pyrid-4-yl)propyl]benzamide;

in the form of a pure enantiomer or of a mixture of enantiomers, or a pharmaceutically acceptable salt, solvate and/or hydrate thereof.

11. A process for the preparation of the compounds of formula (I) according to claim 1 wherein:

a) a compound of formula:

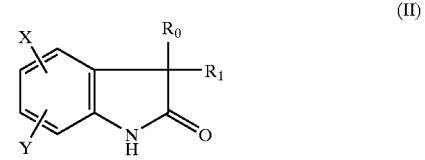

(II)

in which X, Y, $R_0$ and $R_1$ are as defined for (I), is reacted in the presence of a base with a halide of formula:

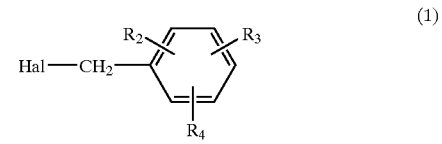

(1)

in which Hal represents a halogen atom and $R_2$, $R_3$ and $R_4$ are as defined for (I);

b) or else, when $R_1$ represents an electrophilic group, the compound of formula:

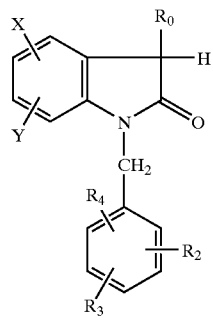

(III)

in which $R_0$, $R_2$, $R_3$, $R_4$, X and Y are as defined for (I), is converted by the action of a derivative $R_1$—Z, in which Z represents a leaving group, in the presence of a base;

c) or else, when $R_1$=OH, an isatin derivative of formula:

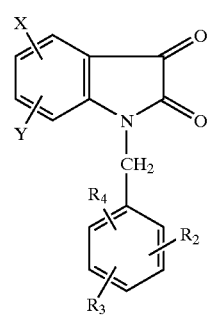

(IV)

in which $R_2$, $R_3$, $R_4$, X and Y are as defined for (I), is reacted with an organometallic derivative $R_0$—M or $R_0$MgHal, $R_0$ being as defined for (I), M being a metal atom and Hal being a bromine or iodine atom;

d) or else the compound of formula:

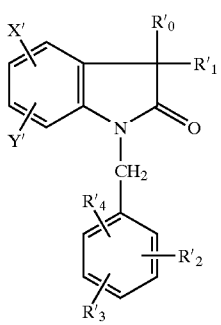

(Ip)

in which $R'_0$, $R'_1$, $R'_2$, $R'_3$, $R'_4$, X' and Y' respectively represent either $R_0$, $R_1$, $R_2$, $R_3$, $R_4$, X and Y as defined for (I) or a precursor group for $R_0$, $R_1$, $R_2$, $R_3$, $R_4$, X and Y, is subjected to a subsequent treatment to convert any one of the $R'_0$, $R'_1$, $R'_2$, $R'_3$, $R'_4$, X' and Y' groups to respectively $R_0$, $R_1$, $R_2$, $R_3$, $R_4$, X or Y as defined for (I).

12. A pharmaceutical composition which comprises, as active principle, a compound according to any one of claims 1 to 10.

13. A pharmaceutical composition which comprises an antagonist of oxytocin receptors according to claim 1 in combination with an antagonist of vasopressin $V_{1a}$ receptors.

14. A composition according to claim 13 for simultaneous or separate use or use spread out over time in the treatment of dysmenorrhoea or endometriosis or the control of premature labour and for controlling preparatory labour for the purpose of a caesarean delivery.

15. A pharmaceutical composition which comprises an antagonist of oxytocin receptors according to claim 2 in combination with an antagonist of vasopressin $V_{1a}$ receptors.

16. A pharmaceutical composition which comprises an antagonist of oxytocin receptors according to claim 3 in combination with an antagonist of vasopressin $V_{1a}$ receptors.

17. A pharmaceutical composition which comprises an antagonist of oxytocin receptors according to claim 4 in combination with an antagonist of vasopressin $V_{1a}$ receptors.

18. A pharmaceutical composition which comprises an antagonist of oxytocin receptors according to claim 5 in combination with an antagonist of vasopressin $V_{1a}$ receptors.

19. A pharmaceutical composition which comprises an antagonist of oxytocin receptors according to claim 6 in combination with an antagonist of vasopressin $V_{1a}$ receptors.

20. A pharmaceutical composition which comprises an antagonist of oxytocin receptors according to claim 7 in combination with an antagonist of vasopressin $V_{1a}$ receptors.

21. A pharmaceutical composition which comprises an antagonist of oxytocin receptors according to claim 8 in combination with an antagonist of vasopressin $V_{1a}$ receptors.

22. A pharmaceutical composition which comprises an antagonist of oxytocin receptors according to claim 9 in combination with an antagonist of vasopressin $V_{1a}$ receptors.

23. A pharmaceutical composition which comprises an antagonist of oxytocin receptors according to claim 10 in combination with an antagonist of vasopressin $V_{1a}$ receptors.

24. A compound according to claim 10 which is 4-Chloro-3-[5-chloro-1-(2,4-dimethoxybenzyl)-3-methyl-2-oxoindolin-3-yl]-N-ethyl-N-(4-pyridylmethyl)-benzamide hydrochloride.

25. A compound according to claim 10 which is 4-Chloro-3-[5-chloro-1-(2,4-dimethoxybenzyl)-3-methyl-2-oxoindolin-3-yl]-N-ethyl-N-(3-pyridylmethyl)benzamide.

26. A compound according to claim 10 which is 4-Chloro-3-[5-chloro-1-(2,4-dimethoxybenzyl)-3-methyl-2-oxoindolin-3-yl]-N-ethyl-N-(2-dimethylaminoethyl) benzamide hydrochloride.

27. A pharmaceutical composition which comprises, as active principle, a compound according to claim 24.

28. A pharmaceutical composition which comprises, as active principle, a compound according to claim 25.

29. A pharmaceutical composition which comprises, as active principle, a compound according to claim 26.

* * * * *

UNITED STATES PATENT AND TRADEMARK OFFICE
CERTIFICATE OF CORRECTION

PATENT NO. : 6,673,790 B1
APPLICATION NO. : 10/240483
DATED : January 6, 2004
INVENTOR(S) : Foulon et al.

It is certified that error appears in the above-identified patent and that said Letters Patent is hereby corrected as shown below:

Column 3, line 57 "Z7 represents a fluorine atom" should read as -- $Z_7$ represents a fluorine atom --

Column 9, line 27 "ethyl}phenyl)-1-(2,4-dimethoxybenzyl" should read as -- methyl}phenyl)-l-(2,4-dimethoxybenzyl) --

Column 13, line 31 "another compound, (I)" should read as -- another compound (I) --

Column 29, line 25 -- $R_3$ = 4-OCH$_3$; $R_4$ = 2-OCH$_3$; X = 5-Cl; Y = H -- should be inserted Column 30, line 11 "$R_3$ = 4-OCH$_3$; $R_4$ = 2-OCH$_3$; X = 5-OCH$_3$; Y = H" should read as -- $R_3$ = 4-OC(CH$_3$)$_3$;$R_4$ = 2-OCH$_3$; X = 5-Cl; Y = H --

Column 30, line 54 "5-Chloro-3-p(2-chlorophenyl)" should read as -- 5-Chloro-3-(2-chlorophenyl) --

Column 30, line 61 "$R_3$ = 4-OCH$_3$; $R_4$ = 2-OCH$_3$; X = 5-OCH$_3$; Y = H" should read as -- $R_3$ = 4-OCH(CH$_3$ )$_2$; $R_4$ = 2-OCH$_3$; X = 5-Cl; Y = H --

Column 31, line 39 "$R_3$ = 4-OCH$_3$; $R_4$ = 2-OCH$_3$; X = 5-OCH$_3$; Y = H" should read as -- $R_3$ = 4-OCH(CH$_3$)$_2$; $R_4$ = 2-OCH$_3$; X = 5-Cl; Y = H --

Column 38, line 37 "5,5-Chloro-l-(2,4-dimethoxybenzyl)" should read as -- 5-Chloro-1-(2,4-dimethoxybenzyl) --

Column 38, lines 53-54, "1,3-l0dioxolane" should read as -- 1,3-dioxolane --

UNITED STATES PATENT AND TRADEMARK OFFICE
CERTIFICATE OF CORRECTION

PATENT NO. : 6,673,790 B1
APPLICATION NO. : 10/240483
DATED : January 6, 2004
INVENTOR(S) : Foulon et al.

It is certified that error appears in the above-identified patent and that said Letters Patent is hereby corrected as shown below:

Column 52, line 63 "A mixture of 0:307 g of the compound" should read as
-- A mixture of 0.307 g of the compound --

Signed and Sealed this

Eighth Day of August, 2006

JON W. DUDAS
*Director of the United States Patent and Trademark Office*